(12) United States Patent
Ma et al.

(10) Patent No.: US 12,702,554 B2
(45) Date of Patent: Aug. 11, 2026

(54) HEART VALVE SEALING DEVICES AND DELIVERY DEVICES THEREFOR

(71) Applicant: Edwards Lifesciences Corporation, Irvine, CA (US)

(72) Inventors: Minh T. Ma, Santa Ana, CA (US); Sergio Delgado, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1038 days.

(21) Appl. No.: 17/845,364

(22) Filed: Jun. 21, 2022

(65) Prior Publication Data

US 2022/0313433 A1 Oct. 6, 2022

Related U.S. Application Data

(63) Continuation of application No. PCT/US2020/065383, filed on Dec. 16, 2020.

(60) Provisional application No. 62/953,098, filed on Dec. 23, 2019.

(51) Int. Cl.
*A61F 2/24* (2006.01)

(52) U.S. Cl.
CPC ............ *A61F 2/246* (2013.01); *A61F 2/2454* (2013.01); *A61F 2/2463* (2013.01); *A61F 2220/0008* (2013.01)

(58) Field of Classification Search
CPC ....... A61F 2/246; A61F 2/2454; A61F 2/2463
See application file for complete search history.

(56) References Cited

U.S. PATENT DOCUMENTS

| | | | |
|---|---|---|---|
| 3,874,388 | A | 4/1975 | King et al. |
| 4,340,091 | A | 7/1982 | Skelton et al. |
| 4,506,669 | A | 3/1985 | Blake, III |
| 4,590,937 | A | 5/1986 | Deniega |
| 4,693,248 | A | 9/1987 | Failla |
| 4,803,983 | A | 2/1989 | Siegel |
| 5,125,895 | A | 6/1992 | Buchbinder et al. |
| 5,171,252 | A | 12/1992 | Friedland |
| 5,195,962 | A | 3/1993 | Martin et al. |

(Continued)

FOREIGN PATENT DOCUMENTS

| | | | |
|---|---|---|---|
| CN | 1142351 | A | 2/1997 |
| CN | 106175845 | A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Suba Ganesan
(74) *Attorney, Agent, or Firm* — Anya Adams

(57) ABSTRACT

A valve repair device includes a pair of anchors and at least one leak inhibitor. The device can also include a spacer or coaptation element. The pair of anchors can be coupled to the spacer or coaptation element. The pair of anchors are movable between an open position and a closed position and are configured to attach the valve repair device to the native valve of the patient. The at least one leak inhibitor extends between the pair of anchors and is configured to inhibit retrograde blood flow through the device, for example, between one or more openings between leaflet portions that are in the anchors.

13 Claims, 63 Drawing Sheets

(56) References Cited

U.S. PATENT DOCUMENTS 5,292,326 A 3/1994 Green et al.
5,327,905 A 7/1994 Avitall
5,363,861 A 11/1994 Edwards et al.
5,370,685 A 12/1994 Stevens
5,389,077 A 2/1995 Melinyshyn et al.
5,411,552 A 5/1995 Andersen et al.
5,450,860 A 9/1995 O'Connor
5,456,674 A 10/1995 Bos et al.
5,474,057 A 12/1995 Makower et al.
5,478,353 A 12/1995 Yoon
5,487,746 A 1/1996 Yu et al.
5,565,004 A 10/1996 Christoudias
5,607,462 A 3/1997 Imran
5,609,598 A 3/1997 Laufer et al.
5,611,794 A 3/1997 Sauer et al.
5,626,607 A 5/1997 Malecki et al.
5,695,504 A 12/1997 Gifford, III et al.
5,716,417 A 2/1998 Girard et al.
5,727,569 A 3/1998 Benetti et al.
5,741,297 A 4/1998 Simon
5,782,746 A 7/1998 Wright
5,797,960 A 8/1998 Stevens et al.
5,836,311 A 11/1998 Borst et al.
5,843,076 A 12/1998 Webster, Jr. et al.
5,855,590 A 1/1999 Malecki et al.
5,885,271 A 3/1999 Hamilton et al.
5,888,247 A 3/1999 Benetti
5,891,017 A 4/1999 Swindle et al.
5,891,112 A 4/1999 Samson
5,894,843 A 4/1999 Benetti et al.
5,921,979 A 7/1999 Kovac et al.
5,944,738 A 8/1999 Amplatz et al.
5,957,835 A 9/1999 Anderson et al.
5,972,020 A 10/1999 Carpentier et al.
5,980,534 A 11/1999 Gimpelson
6,004,329 A 12/1999 Myers et al.
6,010,531 A 1/2000 Donlon et al.
6,017,358 A 1/2000 Yoon et al.
6,086,600 A 7/2000 Kortenbach
6,120,496 A 9/2000 Whayne et al.
6,132,370 A 10/2000 Furnish et al.
6,162,239 A 12/2000 Manhes
6,165,183 A 12/2000 Kuehn et al.
6,182,664 B1 2/2001 Cosgrove
6,193,732 B1 2/2001 Frantzen et al.
6,193,734 B1 2/2001 Bolduc et al.
6,200,315 B1 3/2001 Galser et al.
6,228,032 B1 5/2001 Eaton et al.
6,241,743 B1 6/2001 Levin et al.
6,269,819 B1 8/2001 Oz et al.
6,269,829 B1 8/2001 Chen et al.
6,312,447 B1 11/2001 Grimes
6,461,366 B1 10/2002 Seguin
6,468,285 B1 10/2002 Hsu et al.
6,508,806 B1 1/2003 Hoste
6,508,825 B1 1/2003 Selmon et al.
6,530,933 B1 3/2003 Yeung et al.
6,537,290 B2 3/2003 Adams et al.
6,544,215 B1 4/2003 Bencini et al.
6,626,930 B1 9/2003 Allen et al.
6,629,534 B1 10/2003 Goar et al.
6,719,767 B1 4/2004 Kimblad
6,764,510 B2 7/2004 Vidlund et al.
6,770,083 B2 8/2004 Seguin
6,837,867 B2 1/2005 Kortelling
6,855,137 B2 2/2005 Bon
6,913,614 B2 7/2005 Marino et al.
6,939,337 B2 9/2005 Parker et al.
6,945,956 B2 9/2005 Waldhauser et al.
7,048,754 B2 5/2006 Martin et al.
7,101,395 B2 9/2006 Tremulis et al.
7,125,421 B2 10/2006 Tremulis et al.
7,288,097 B2 10/2007 Seguin
7,371,210 B2 5/2008 Brock et al.
7,464,712 B2 12/2008 Oz et al.
7,509,959 B2 3/2009 Oz et al.
7,569,062 B1 8/2009 Kuehn et al.
7,618,449 B2 11/2009 Tremulis et al.
7,682,369 B2 3/2010 Seguin
7,731,706 B2 6/2010 Potter
7,744,609 B2 6/2010 Allen et al.
7,748,389 B2 7/2010 Salahieh et al.
7,753,932 B2 7/2010 Gingrich et al.
7,758,596 B2 7/2010 Oz et al.
7,780,723 B2 8/2010 Taylor
7,803,185 B2 9/2010 Gabbay
7,824,443 B2 11/2010 Salahieh et al.
7,981,123 B2 7/2011 Seguin
7,988,724 B2 8/2011 Salahieh et al.
8,052,750 B2 11/2011 Tuval et al.
8,070,805 B2 12/2011 Vidlund et al.
8,096,985 B2 1/2012 Legaspi et al.
8,104,149 B1 1/2012 McGarity
8,133,239 B2 3/2012 Oz et al.
8,147,542 B2 4/2012 Maisano et al.
8,172,856 B2 5/2012 Eigler et al.
8,206,437 B2 6/2012 Bonhoeffer et al.
8,216,301 B2 7/2012 Bonhoeffer et al.
8,303,653 B2 11/2012 Bonhoeffer et al.
8,313,525 B2 11/2012 Tuval et al.
8,348,995 B2 1/2013 Tuval et al.
8,348,996 B2 1/2013 Tuval et al.
8,414,643 B2 4/2013 Tuval et al.
8,425,404 B2 4/2013 Wilson et al.
8,449,599 B2 5/2013 Chau et al.
8,449,606 B2 5/2013 Ellasen et al.
8,460,368 B2 6/2013 Taylor et al.
8,470,028 B2 6/2013 Thornton et al.
8,480,730 B2 7/2013 Maurer et al.
8,540,767 B2 9/2013 Zhang
8,579,965 B2 11/2013 Bonhoeffer et al.
8,585,756 B2 11/2013 Bonhoeffer et al.
8,652,202 B2 2/2014 Alon et al.
8,668,733 B2 3/2014 Haug et al.
8,721,665 B2 5/2014 Oz et al.
8,740,918 B2 6/2014 Seguin
8,771,347 B2 7/2014 DeBoer et al.
8,778,017 B2 7/2014 Ellasen et al.
8,834,564 B2 9/2014 Tuval et al.
8,840,663 B2 9/2014 Salahieh et al.
8,876,894 B2 11/2014 Tuval et al.
8,876,895 B2 11/2014 Tuval et al.
8,945,177 B2 2/2015 Dell et al.
9,034,032 B2 5/2015 McLean et al.
9,198,757 B2 12/2015 Schroeder et al.
9,220,507 B1 12/2015 Patel et al.
9,259,317 B2 2/2016 Wilson et al.
9,282,972 B1 3/2016 Patel et al.
9,301,834 B2 4/2016 Tuval et al.
9,308,360 B2 4/2016 Bishop et al.
9,387,071 B2 7/2016 Tuval et al.
9,427,327 B2 8/2016 Parrish
9,439,763 B2 9/2016 Geist et al.
9,510,837 B2 12/2016 Seguin
9,510,946 B2 12/2016 Chau et al.
9,572,660 B2 2/2017 Braido et al.
9,642,704 B2 5/2017 Tuval et al.
9,700,445 B2 7/2017 Martin et al.
9,775,963 B2 10/2017 Miller
D809,139 S 1/2018 Marsot et al.
9,889,002 B2 2/2018 Bonhoeffer et al.
9,949,824 B2 4/2018 Bonhoeffer et al.
10,076,327 B2 9/2018 Ellis et al.
10,076,415 B1 * 9/2018 Metchik .................. A61F 2/246
10,099,050 B2 10/2018 Chen et al.
10,105,221 B2 10/2018 Siegel
10,105,222 B1 10/2018 Metchik et al.
10,111,751 B1 10/2018 Metchik et al.
10,123,873 B1 11/2018 Metchik et al.
10,130,475 B1 11/2018 Metchik et al.
10,136,993 B1 11/2018 Metchik et al.
10,159,570 B1 12/2018 Metchik et al.
10,226,309 B2 3/2019 Ho et al.
10,231,837 B1 3/2019 Metchik et al.

(56) References Cited

U.S. PATENT DOCUMENTS 10,238,493 B1 3/2019 Metchik et al.
10,238,494 B2 3/2019 McNiven et al.
10,238,495 B2 3/2019 Marsot et al.
10,299,924 B2 5/2019 Kizuka
10,376,673 B2 8/2019 Van Hoven et al.
10,575,841 B1 3/2020 Paulos
2001/0005787 A1 6/2001 Oz et al.
2002/0013571 A1 1/2002 Goldfarb et al.
2002/0107531 A1 8/2002 Schreck et al.
2002/0173811 A1 11/2002 Tu et al.
2002/0183787 A1 12/2002 Wahr et al.
2003/0144573 A1 7/2003 Heilman et al.
2003/0187467 A1 10/2003 Schreck
2003/0208231 A1 11/2003 Williamson et al.
2004/0003819 A1 1/2004 St. Goar et al.
2004/0030382 A1 2/2004 St. Goar et al.
2004/0034365 A1 2/2004 Lentz et al.
2004/0044350 A1 3/2004 Martin et al.
2004/0044365 A1 3/2004 Bachman
2004/0049207 A1 3/2004 Goldfarb et al.
2004/0122448 A1 6/2004 Levine
2004/0127981 A1 7/2004 Rahdert et al.
2004/0127982 A1 7/2004 Machold et al.
2004/0147943 A1 7/2004 Kobayashi
2004/0181135 A1 9/2004 Drysen
2004/0181206 A1 9/2004 Chiu et al.
2004/0181238 A1 9/2004 Zarbatany et al.
2004/0210307 A1 10/2004 Khairkhahan
2004/0220593 A1 11/2004 Greenhalgh
2005/0010287 A1 1/2005 Macoviak et al.
2005/0049618 A1 3/2005 Masuda et al.
2005/0070926 A1 3/2005 Ortiz
2005/0137690 A1 6/2005 Salahieh et al.
2005/0143767 A1 6/2005 Kimura et al.
2005/0165429 A1 7/2005 Douglas et al.
2005/0216039 A1 9/2005 Lederman
2005/0251177 A1 11/2005 Saadat et al.
2005/0251183 A1 11/2005 Buckman et al.
2005/0288786 A1 12/2005 Chanduszko
2006/0020275 A1 1/2006 Goldfarb et al.
2006/0089671 A1 4/2006 Goldfarb et al.
2006/0100649 A1 5/2006 Hart
2006/0122647 A1 6/2006 Callaghan et al.
2006/0142694 A1 6/2006 Bednarek et al.
2006/0173251 A1 8/2006 Govari et al.
2006/0178700 A1 8/2006 Quinn
2006/0224169 A1 10/2006 Weisenburgh et al.
2007/0010800 A1 1/2007 Weitzner et al.
2007/0010877 A1 1/2007 Salahieh et al.
2007/0016286 A1 1/2007 Herrmann et al.
2007/0021779 A1 1/2007 Garvin et al.
2007/0032807 A1 2/2007 Ortiz et al.
2007/0093857 A1 4/2007 Rogers et al.
2007/0093890 A1 4/2007 Eliasen et al.
2007/0156197 A1 7/2007 Root et al.
2007/0191154 A1 8/2007 Genereux et al.
2007/0197858 A1 8/2007 Goldfarb et al.
2007/0198038 A1 8/2007 Cohen et al.
2007/0265700 A1 11/2007 Ellasen et al.
2007/0282414 A1 12/2007 Soltis et al.
2007/0293943 A1 12/2007 Quinn
2007/0299387 A1 12/2007 Williams et al.
2007/0299424 A1 12/2007 Cumming et al.
2008/0039743 A1 2/2008 Fox et al.
2008/0039953 A1 2/2008 Davis et al.
2008/0065149 A1 3/2008 Thielen et al.
2008/0077144 A1 3/2008 Crofford
2008/0091169 A1 4/2008 Heideman et al.
2008/0140089 A1 6/2008 Kogiso et al.
2008/0147093 A1 6/2008 Roskopf et al.
2008/0147112 A1 6/2008 Sheets et al.
2008/0149685 A1 6/2008 Smith et al.
2008/0167713 A1 7/2008 Bolling
2008/0177300 A1 7/2008 Mas et al.
2008/0208332 A1 8/2008 Lamphere et al.
2008/0221672 A1 9/2008 Lamphere et al.
2008/0255427 A1 10/2008 Satake et al.
2008/0281411 A1 11/2008 Berreklouw
2008/0287862 A1 11/2008 Weitzner et al.
2008/0294247 A1 11/2008 Yang et al.
2008/0312506 A1 12/2008 Spivey et al.
2008/0319455 A1 12/2008 Harris et al.
2009/0005863 A1 1/2009 Goetz et al.
2009/0024110 A1 1/2009 Heideman et al.
2009/0131880 A1 5/2009 Speziali et al.
2009/0156995 A1 6/2009 Martin et al.
2009/0163934 A1 6/2009 Raschdorf, Jr. et al.
2009/0166913 A1 7/2009 Guo et al.
2009/0177266 A1 7/2009 Powell et al.
2009/0234280 A1 9/2009 Tah et al.
2009/0275902 A1 11/2009 Heeps et al.
2009/0287304 A1 11/2009 Dahlgren et al.
2010/0022823 A1 1/2010 Goldfarb et al.
2010/0057192 A1 3/2010 Celermajer
2010/0069834 A1 3/2010 Schultz
2010/0094317 A1 4/2010 Goldfarb et al.
2010/0106141 A1 4/2010 Osypka et al.
2010/0121434 A1 5/2010 Paul et al.
2010/0249497 A1 9/2010 Peine et al.
2010/0298929 A1 11/2010 Thornton et al.
2010/0324595 A1 12/2010 Linder et al.
2011/0082538 A1 4/2011 Dahlgren et al.
2011/0137410 A1 6/2011 Hacohen
2011/0245855 A1 10/2011 Matsuoka et al.
2011/0257723 A1 10/2011 McNamara
2011/0295281 A1 12/2011 Mizumoto et al.
2012/0022633 A1 1/2012 Olson et al.
2012/0089125 A1 4/2012 Scheibe et al.
2012/0109160 A1 5/2012 Martinez et al.
2012/0116419 A1 5/2012 Sigmon, Jr.
2012/0209318 A1 8/2012 Qadeer
2012/0277853 A1 11/2012 Rothstein
2013/0035759 A1 2/2013 Gross et al.
2013/0041314 A1 2/2013 Dillon
2013/0066341 A1 3/2013 Ketai et al.
2013/0066342 A1 3/2013 Dell et al.
2013/0072945 A1 3/2013 Terada
2013/0073034 A1 3/2013 Wilson et al.
2013/0110254 A1 5/2013 Osborne
2013/0190798 A1 7/2013 Kapadia
2013/0190861 A1 7/2013 Chau et al.
2013/0268069 A1 10/2013 Zakai et al.
2013/0282059 A1 10/2013 Ketai et al.
2013/0304197 A1 11/2013 Buchbinder et al.
2013/0325110 A1 12/2013 Khalil et al.
2014/0031928 A1 1/2014 Murphy et al.
2014/0046433 A1 2/2014 Kovalsky
2014/0046434 A1 2/2014 Rolando et al.
2014/0052237 A1 2/2014 Lane et al.
2014/0058411 A1 2/2014 Soutorine et al.
2014/0067048 A1 3/2014 Chau et al.
2014/0067052 A1 3/2014 Chau et al.
2014/0094903 A1 4/2014 Miller et al.
2014/0135685 A1 5/2014 Kabe et al.
2014/0194975 A1 7/2014 Quill et al.
2014/0200662 A1 7/2014 Eftel et al.
2014/0207231 A1 7/2014 Hacohen et al.
2014/0222136 A1* 8/2014 Geist .................... A61F 2/2436
623/2.37
2014/0236198 A1 8/2014 Goldfarb et al.
2014/0243968 A1 8/2014 Padala
2014/0251042 A1 9/2014 Asselin et al.
2014/0277404 A1 9/2014 Wilson et al.
2014/0277411 A1 9/2014 Bortlein et al.
2014/0277427 A1 9/2014 Ratz et al.
2014/0316428 A1 10/2014 Golan
2014/0324164 A1 10/2014 Gross et al.
2014/0330368 A1 11/2014 Gloss et al.
2014/0336751 A1 11/2014 Kramer
2014/0371843 A1 12/2014 Wilson et al.
2015/0039084 A1 2/2015 Levi et al.
2015/0057704 A1 2/2015 Takahashi
2015/0094802 A1 4/2015 Buchbinder et al.
2015/0100116 A1 4/2015 Mohl et al.

(56) References Cited

U.S. PATENT DOCUMENTS

2015/0105808 A1 4/2015 Gordon et al.
2015/0148896 A1 5/2015 Karapetian et al.
2015/0157268 A1 6/2015 Winshtein et al.
2015/0196390 A1 7/2015 Ma et al.
2015/0223793 A1 8/2015 Goldfarb et al.
2015/0230919 A1 8/2015 Chau et al.
2015/0238313 A1 8/2015 Spence et al.
2015/0257757 A1 9/2015 Powers et al.
2015/0257877 A1 9/2015 Hernandez
2015/0257883 A1 9/2015 Basude et al.
2015/0313592 A1 11/2015 Coillard-Lavirotte et al.
2015/0351904 A1 12/2015 Cooper et al.
2015/0366666 A1 12/2015 Khairkhahan et al.
2016/0008129 A1 1/2016 Siegel
2016/0008131 A1 1/2016 Christianson et al.
2016/0022970 A1 1/2016 Forcucci et al.
2016/0051796 A1 2/2016 Kanemasa et al.
2016/0074164 A1 3/2016 Naor
2016/0074165 A1 3/2016 Spence et al.
2016/0106539 A1 4/2016 Buchbinder et al.
2016/0113762 A1 4/2016 Clague et al.
2016/0113764 A1 4/2016 Sheahan et al.
2016/0113766 A1 4/2016 Ganesan et al.
2016/0155987 A1 6/2016 Yoo et al.
2016/0174979 A1 6/2016 Wei
2016/0174981 A1 6/2016 Fago et al.
2016/0242906 A1 8/2016 Morriss et al.
2016/0287387 A1 10/2016 Wei
2016/0302811 A1 10/2016 Rodriguez-Navarro et al.
2016/0317290 A1 11/2016 Chau et al.
2016/0331523 A1 11/2016 Chau et al.
2016/0354082 A1 12/2016 Oz et al.
2017/0020521 A1 1/2017 Krone et al.
2017/0035561 A1 2/2017 Rowe et al.
2017/0035566 A1 2/2017 Krone et al.
2017/0042456 A1 2/2017 Budiman
2017/0042678 A1 2/2017 Ganesan et al.
2017/0049455 A1 2/2017 Seguin
2017/0100119 A1 4/2017 Baird et al.
2017/0100236 A1 4/2017 Robertson et al.
2017/0224955 A1 8/2017 Douglas et al.
2017/0239048 A1 8/2017 Goldfarb et al.
2017/0252154 A1 9/2017 Tubishevitz et al.
2017/0266413 A1 9/2017 Khuu et al.
2017/0281330 A1 10/2017 Liljegren et al.
2017/0348102 A1 12/2017 Cousins et al.
2018/0008311 A1 1/2018 Shiroff et al.
2018/0021044 A1 1/2018 Miller et al.
2018/0021129 A1 1/2018 Peterson et al.
2018/0021134 A1 1/2018 McNiven et al.
2018/0071487 A1 3/2018 Khuu et al.
2018/0078271 A1 3/2018 Thrasher, III
2018/0078361 A1 3/2018 Naor et al.
2018/0092661 A1 4/2018 Prabhu
2018/0126124 A1 5/2018 Winston et al.
2018/0133008 A1 5/2018 Kizuka et al.
2018/0146964 A1 5/2018 Garcia et al.
2018/0146966 A1 5/2018 Hernandez et al.
2018/0153552 A1 6/2018 King et al.
2018/0161159 A1 6/2018 Lee et al.
2018/0168803 A1 6/2018 Pesce et al.
2018/0185154 A1 7/2018 Cao
2018/0221147 A1 8/2018 Ganesan et al.
2018/0235657 A1 8/2018 Abunassar
2018/0243086 A1 8/2018 Barbarino et al.
2018/0258665 A1 9/2018 Reddy et al.
2018/0263767 A1 9/2018 Chau et al.
2018/0296326 A1 10/2018 Dixon et al.
2018/0296327 A1 10/2018 Dixon et al.
2018/0296328 A1 10/2018 Dixon et al.
2018/0296329 A1 10/2018 Dixon et al.
2018/0296330 A1 10/2018 Dixon et al.
2018/0296331 A1 10/2018 Dixon et al.
2018/0296332 A1 10/2018 Dixon et al.
2018/0296333 A1 10/2018 Dixon et al.
2018/0296334 A1 10/2018 Dixon et al.
2018/0325661 A1 11/2018 Delgado et al.
2018/0325671 A1 11/2018 Abunassar et al.
2018/0333259 A1 11/2018 Dibie
2018/0344457 A1 12/2018 Gross et al.
2018/0353181 A1 12/2018 Wei
2019/0000613 A1 1/2019 Delgado et al.
2019/0000623 A1 1/2019 Pan et al.
2019/0008642 A1 1/2019 Delgado et al.
2019/0008643 A1 1/2019 Delgado et al.
2019/0015199 A1 1/2019 Delgado et al.
2019/0015200 A1 1/2019 Delgado et al.
2019/0015207 A1 1/2019 Delgado et al.
2019/0015208 A1 1/2019 Delgado et al.
2019/0021851 A1 1/2019 Delgado et al.
2019/0021852 A1 1/2019 Delgado et al.
2019/0029498 A1 1/2019 Mankowski et al.
2019/0029810 A1 1/2019 Delgado et al.
2019/0029813 A1 1/2019 Delgado et al.
2019/0030285 A1 1/2019 Prabhu et al.
2019/0053810 A1 2/2019 Griffin
2019/0060058 A1 2/2019 Delgado et al.
2019/0060059 A1 2/2019 Delgado et al.
2019/0060072 A1 2/2019 Zeng
2019/0060073 A1 2/2019 Delgado et al.
2019/0060074 A1 2/2019 Delgado et al.
2019/0060075 A1 2/2019 Delgado et al.
2019/0069991 A1 3/2019 Metchik et al.
2019/0069992 A1 3/2019 Delgado et al.
2019/0069993 A1 3/2019 Delgado et al.
2019/0105156 A1 4/2019 He et al.
2019/0111239 A1 4/2019 Bolduc et al.
2019/0117113 A1 4/2019 Curran
2019/0142589 A1 5/2019 Basude
2019/0159782 A1 5/2019 Kamaraj et al.
2019/0167197 A1 6/2019 Abunassar et al.
2019/0183644 A1 6/2019 Hacohen
2019/0192296 A1 6/2019 Schwartz et al.
2019/0209299 A1 7/2019 Metchik et al.
2019/0209323 A1 7/2019 Metchik et al.
2019/0261995 A1 8/2019 Goldfarb et al.
2019/0261996 A1 8/2019 Goldfarb et al.
2019/0261997 A1 8/2019 Goldfarb et al.
2019/0314155 A1 10/2019 Franklin et al.
2019/0321166 A1 10/2019 Freschauf et al.
2020/0113683 A1 4/2020 Dale et al.
2020/0138569 A1 5/2020 Basude et al.
2020/0205979 A1 7/2020 O'Carroll et al.
2020/0237512 A1 7/2020 McCann et al.
2020/0337842 A1 10/2020 Metchik et al.
2020/0352717 A1 11/2020 Kheradvar et al.
2020/0360054 A1 11/2020 Walsh et al.
2020/0360132 A1 11/2020 Spence
2020/0368016 A1 11/2020 Pesce et al.
2021/0022850 A1 1/2021 Basude et al.
2021/0059680 A1 3/2021 Lin et al.
2021/0169650 A1 6/2021 Dai et al.
2021/0186698 A1 6/2021 Abunassar et al.
2021/0307900 A1 10/2021 Hacohen
2021/0330456 A1 10/2021 Hacohen et al.
2021/0338418 A1 11/2021 Feld
2021/0361238 A1 11/2021 Bak-Boychuk et al.
2021/0361422 A1 11/2021 Gross et al.
2021/0378818 A1 12/2021 Manash et al.
2021/0401434 A1 12/2021 Tien et al.
2022/0039954 A1 2/2022 Nia et al.
2022/0071767 A1 3/2022 Dixon et al.
2022/0133327 A1 5/2022 Zhang et al.
2022/0142780 A1 5/2022 Zhang et al.
2022/0142781 A1 5/2022 Zhang et al.
2022/0226108 A1 7/2022 Freschauf et al.
2022/0233312 A1 7/2022 Delgado et al.
2022/0257196 A1 8/2022 Massmann
2022/0287841 A1 9/2022 Freschauf et al.
2022/0296248 A1 9/2022 Abunassar et al.
2023/0014540 A1 1/2023 Metchik et al.
2023/0149170 A1 5/2023 Giese et al.

(56) References Cited

U.S. PATENT DOCUMENTS

| | | | |
|---|---|---|---|
| 2023/0218291 | A1 | 7/2023 | Zarbatany et al. |
| 2023/0270549 | A1 | 8/2023 | Guidotti et al. |
| 2024/0148505 | A1 | 5/2024 | Datta et al. |

FOREIGN PATENT DOCUMENTS

| | | | |
|---|---|---|---|
| CN | 106491245 | A | 3/2017 |
| CN | 107789017 | A | 3/2018 |
| CN | 109953779 | A | 7/2019 |
| CN | 110338857 | A | 10/2019 |
| CN | 110495972 | A | 11/2019 |
| CN | 110537946 | A | 12/2019 |
| CN | 110664515 | A | 1/2020 |
| CN | 209996540 | U | 1/2020 |
| CN | 211243911 | U | 8/2020 |
| CN | 211723546 | U | 10/2020 |
| CN | 111870398 | A | 11/2020 |
| CN | 111904660 | A | 11/2020 |
| CN | 112120831 | A | 12/2020 |
| CN | 112168427 | A | 1/2021 |
| CN | 112190367 | A | 1/2021 |
| CN | 212346813 | U | 1/2021 |
| CN | 212415988 | U | 1/2021 |
| CN | 212490263 | U | 2/2021 |
| CN | 113476182 | A | 10/2021 |
| CN | 113855328 | A | 12/2021 |
| CN | 215019733 | U | 12/2021 |
| EP | 0098100 | A2 | 1/1984 |
| FR | 2146050 | A5 | 2/1973 |
| FR | 9711600 | | 3/1997 |
| JP | 2019536576 | A | 12/2019 |
| WO | WO-2014064694 | A2 | 5/2014 |
| WO | 2017015632 | A1 | 1/2017 |
| WO | 2018013856 | A1 | 1/2018 |
| WO | 2018050200 | A1 | 3/2018 |
| WO | 2018050203 | A1 | 3/2018 |
| WO | 2018195015 | A1 | 10/2018 |
| WO | 2018195201 | A1 | 10/2018 |
| WO | 2018195215 | A2 | 10/2018 |
| WO | 2019139904 | A1 | 7/2019 |
| WO | 2020106705 | A1 | 5/2020 |
| WO | 2020106827 | A1 | 5/2020 |
| WO | 2020112622 | A1 | 6/2020 |
| WO | 2020167677 | A1 | 8/2020 |
| WO | 2020168081 | A1 | 8/2020 |
| WO | 2020172224 | A1 | 8/2020 |
| WO | 2020176410 | A1 | 9/2020 |
| WO | 2021196580 | A1 | 10/2021 |
| WO | 2021227412 | A1 | 11/2021 |
| WO | WO-2022006087 | A2 | 1/2022 |
| WO | WO-2022036209 | A1 | 2/2022 |
| WO | 2022052506 | A1 | 3/2022 |
| WO | WO-2022051241 | A1 | 3/2022 |
| WO | 2022068188 | A1 | 4/2022 |
| WO | WO-2022101817 | A2 | 5/2022 |
| WO | WO-2022140175 | A1 | 6/2022 |
| WO | WO-2022153131 | A1 | 7/2022 |
| WO | WO-2022155298 | A2 | 7/2022 |
| WO | WO-2022157592 | A1 | 7/2022 |
| WO | WO-2022212172 | A1 | 10/2022 |
| WO | WO-2023003755 | A1 | 1/2023 |
| WO | WO-2023004098 | A1 | 1/2023 |
| WO | WO-2023278663 | A2 | 1/2023 |
| WO | WO-2023288003 | A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Batista RJ et al., "Partial left ventriculectomy to treat end-stage heart disease", Ann Thorac Surg., vol. 64, Issue-3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, January- Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Falling Grade in a New Study", The New York Times, Janurary 3,1991, pp. 1-2 [online], [retrieved on Jul. 29, 2009]. Retrieved from the Internet <URL:http://www.nytimes. com/1991/01/03/health/device-that-opens-clogged-arteries-gets-a-faill . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue-3, pp. 240-245, Mar. 1998.

Pavcnik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.

Reul RM et al., "Mitral valve reconstruction for mitral insufficiency", Prog Cardiovasc Dis., vol. 39, Issue-6, May-Jun. 1997.

Rösch et al., "The Birth, Early Years and Future of Interventional Radiology," Journal of Vascular and Interventional Radiology, vol. 14, No. 7, pp. 841-853, Jul. 1, 2003, Elsevier, United States.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Serruys et al., "Stenting of coronary arteries. Are we the sorcerer's apprentice?", European Heart Journal, vol. 10 No. 9 pp. 774-782, Sep. 1, 1989, The European Society of Cardiology, Oxford University Press, United Kingdom.

(56) References Cited

OTHER PUBLICATIONS

Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Umaña JP et al., Bow-tie' mitral valve repair: an adjuvant technique for ischemic mitral regurgitation, Ann Thorac Surg., vol. 66, Issue-6, pp. 1640-1646, Nov. 1998.

Urban, Philip Md, "Coronary Artery Stenting", pp. 5-47, © 1991, ISBN: 2-88049-054-5, Editions Medecine et Hygiene, Geneva, Switzerland.

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.

Grasso C., et al., "The Pascal Transcatheter Mitral Valve Repair System for the Treatment of Mitral Regurgitation: Another Piece to the Puzzle of Edge-to-edge Technique," Journal of Thoracic Disease, AME Publishing Company, Hong Kong, China, Dec. 2017, vol. 9, No. 12, pp. 4856-4859, DOI: 10.21037/jtd.2017.10.156.

* cited by examiner 100
115
110
130
126
120
138
114
124
128

MV
120
24
130
22
114
2800
110
2800 2400
2400
100
20
120 130

MV
24
22
20
120
130
2800
2800
2400
2400
4801
4801
100
130
120

HEART VALVE SEALING DEVICES AND DELIVERY DEVICES THEREFOR

RELATED APPLICATIONS

The present application is a continuation of Patent Cooperation Treaty Application No. PCT/US/2020/065383, filed on Dec. 16, 2020, which claims the benefit of U.S. provisional application No. 62/953,098 filed on Dec. 23, 2019, which are both incorporated herein by reference in their entireties for all purposes.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, for example, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive, and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

A native valve of a patient can be repaired by attaching a spacer between leaflets of the native valve of the patient. Retrograde blood flow through gaps between the spacer and the leaflets is blocked or inhibited.

An example valve repair device includes a spacer, a pair of paddles, and at least one leak control extension. The pair of anchors (e.g., paddles, latches, clamps, grippers, fasteners, etc.) can be coupled to the spacer. The pair of anchors (e.g., a pair of paddles) are movable between an open position and a closed position and are configured to attach the valve repair device to the native valve of the patient. The at least one leak control extension extends from the spacer and is configured to block retrograde blood flow along sides of the spacer.

An example valve repair system includes a delivery sheath and a valve repair device. The valve repair device is deployable to the native valve of the patient by the delivery sheath. The valve repair device includes a spacer, a pair of paddles, and at least one leak control extension. The pair of paddles are coupled to the spacer. The pair of paddles are movable between an open position and a closed position and are configured to attach the valve repair device to the native valve of the patient. The at least one leak control extension extends from the spacer and is configured to block retrograde blood flow along sides of the spacer.

In some implementations, a valve repair device for repairing a native valve of a patient comprises a spacer, a pair of anchors (e.g., paddles, latches, clamps, grippers, fasteners, etc.) configured to attach the valve repair device to the native valve of the patient, and at least one leak control extension extending from the spacer.

In some implementations, the pair of anchors are a pair of paddles coupled to the spacer. In some implementations, the pair of paddles are movable between an open position and a closed position.

In some implementations, the at least one leak control extension extends from the spacer. The leak control extension is configured to block retrograde blood flow along sides of the spacer.

In some implementations, the valve repair device further comprises a cap that is connected to the spacer. In some implementations, the at least one leak control extension is connected to the cap that is connected to the spacer. In some implementations, the at least one leak control extension is pivotally attached to the cap. In some implementations, the at least one leak control extension is connected directly to the spacer.

In some implementations, the valve repair device further comprises a pair of clasps, wherein the pair of anchors (e.g., a pair of paddles) and the pair of clasps are configured to attach the valve repair device to the native valve of the patient.

In some implementations, the spacer is configured to close a gap in the native valve of the patient when the valve repair device is attached to the native valve.

In some implementations, the at least one leak control extension comprises a deflector paddle having a flexible wire frame covered by a cloth barrier material. The deflector paddle can be connected to the spacer by one or more arms.

In some implementations, the flexible wire frame is configured to deform when positioned against a wall within the heart of the patient.

In some implementations, the at least one leak control extension comprises a pocket that includes a flexible wire frame that defines an opening of the pocket and a cloth barrier material that defines at least a portion of the interior of the pocket. In some implementations, the opening of the at least one leak control extension is configured to be positioned below one or more leaflets of the native valve when the valve repair device is attached to the native valve. In some implementations, the opening of the at least one leak control extension is configured to be positioned above a ventricular end of the one or more leaflets of the native valve when the valve repair device is attached to the native valve.

In some implementations, at least a portion of the leak control extension is configured to be positioned below a ventricular end of one or more leaflets of the native valve when the valve repair device is attached to the native valve.

In some implementations, the entire leak control extension is configured to be positioned above a ventricular end of one or more leaflets of the native valve when the valve repair device is attached to the native valve. In some implementations, the entire leak control extension is configured to be positioned below a ventricular end of one or more leaflets of the native valve when the valve repair device is attached to the native valve.

In some implementations, the at least one leak control extension comprises one or more deflector paddles and a barrier element. In some implementations, each of the one or more deflector paddles has a flexible wire frame covered by a cloth barrier material. In some implementations, the barrier element comprises at least one of a cloth material, a biocompatible material, bovine or porcine heart tissue, and a plastic membrane.

In some implementations, a valve repair device for repairing a native valve comprises at least one anchor (e.g., a paddle, latch, clamp, gripper, fastener, etc.) configured to attach the valve repair device to the native valve of the patient and at least one leak control extension extending from a portion of the valve repair device.

In some implementations, the at least one anchor is movable between an open position and a closed position.

In some implementations, the at least one leak control extension is configured to block retrograde blood flow adjacent or near the device.

In some implementations, the valve repair device further comprises a coaption element (e.g., coaptation element, spacer, etc.). The coaption element is configured to close a gap in the native valve of the patient when the valve repair device is attached to the native valve. In some implementations, the at least one leak control extension extends from the coaption element and is configured to block retrograde blood flow along sides of the coaption element.

In some implementations, the valve repair device further comprises a cap that is connected to the coaption element. In some implementations, the at least one leak control extension is connected directly to the coaption element. In some implementations, the at least one leak control extension is connected to the cap that is connected to the coaption element. In some implementations, the at least one leak control extension is pivotally attached to the cap.

In some implementations, the at least one anchor is coupled to the coaption element. In some implementations, the at least one anchor comprises a pair of paddles coupled to the coaption element.

In some implementations, the at least one anchor comprises a pair of paddles.

In some implementations, the valve repair device further comprises at least one clasp, wherein the at least one anchor and the at least one clasp are configured to attach the valve repair device to the native valve of the patient.

In some implementations, the at least one clasp is coupled to a cap of the device.

In some implementations, the at least one leak control extension comprises a deflector paddle having a flexible wire frame covered by a cloth barrier material. In some implementations, the deflector paddle is connected to the spacer by one or more arms. In some implementations, the flexible wire frame is configured to deform when positioned against a wall within the native valve of the patient.

In some implementations, the at least one leak control extension comprises a pocket that includes a flexible wire frame that defines an opening of the pocket and a cloth barrier material that defines at least a portion of the interior of the pocket. In some implementations, the opening of the at least one leak control extension is configured to be positioned below one or more leaflets of the native valve when the valve repair device is attached to the native valve. In some implementations, the opening of the at least one leak control extension is configured to be positioned above a ventricular end of the one or more leaflets of the native valve when the valve repair device is attached to the native valve.

In some implementations, at least a portion of the leak control extension is configured to be positioned below a ventricular end of one or more leaflets of the native valve when the valve repair device is attached to the native valve. In some implementations, the entire leak control extension is configured to be positioned above a ventricular end of one or more leaflets of the native valve when the valve repair device is attached to the native valve. In some implementations, the entire leak control extension is configured to be positioned below a ventricular end of one or more leaflets of the native valve when the valve repair device is attached to the native valve.

In some implementations, the at least one leak control extension comprises one or more deflector paddles and a barrier element. In some implementations, the one or more deflector paddles has a flexible wire frame covered by a cloth barrier material. In some implementations, the barrier element comprises at least one of a cloth material, a biocompatible material, bovine or porcine heart tissue, and a plastic membrane.

In some implementations, a valve repair system for repairing a native valve of a patient comprises a delivery sheath and a valve repair device that is deployable to a native valve of the patient by the delivery sheath.

In some implementations, the valve repair device comprises a coaption element or spacer, a pair of paddles (or other anchors) coupled to the spacer/coaption element, and at least one leak control extension extending from the spacer/coaption element, wherein the leak control extension is configured to block retrograde blood flow along sides of the spacer/coaption element.

In some implementations, the pair of paddles (or other anchors) are movable between an open position and a closed position, wherein the pair of paddles (or other anchors) are configured to attach the valve repair device to the native valve of the patient.

In some implementations, the system (e.g., the valve repair device of the system) further comprises a cap that is connected to the spacer/coaption element. In some implementations, the at least one leak control extension is connected to the cap that is connected to the spacer/coaption element. In some implementations, the at least one leak control extension is pivotally attached to the cap.

In some implementations, the at least one leak control extension is connected directly to the spacer/coaption element.

In some implementations, the system (e.g., the valve repair device of the system) further comprises pair of clasps, wherein the pair of paddles (or other anchors) and the pair of clasps are configured to attach the valve repair device to the native valve of the patient.

In some implementations, the spacer/coaption element is configured to close a gap in the native valve of the patient when the valve repair device is attached to the native valve.

In some implementations, the at least one leak control extension comprises a deflector paddle having a flexible wire frame covered by a cloth barrier material. In some implementations, the deflector paddle is connected to the spacer by one or more arms. In some implementations, the flexible wire frame is configured to deform when positioned against a wall within the heart of the patient.

In some implementations, the at least one leak control extension comprises a pocket that includes a flexible wire frame that defines an opening of the pocket and a cloth barrier material that defines at least a portion of the interior of the pocket. In some implementations, the opening of the at least one leak control extension is configured to be positioned below one or more leaflets of the native valve when the valve repair device is attached to the native valve. In some implementations, the opening of the at least one leak control extension is configured to be positioned above a ventricular end of the one or more leaflets of the native valve when the valve repair device is attached to the native valve.

In some implementations, at least a portion of the leak control extension is configured to be positioned below a ventricular end of one or more leaflets of the native valve when the valve repair device is attached to the native valve.

In some implementations, the entire leak control extension is configured to be positioned above a ventricular end of one or more leaflets of the native valve when the valve repair device is attached to the native valve. In some implementations, the entire leak control extension is configured to be positioned below a ventricular end of one or more leaflets of the native valve when the valve repair device is attached to the native valve.

In some implementations, the at least one leak control extension comprises one or more deflector paddles and a barrier element. In some implementations, each of the one or more deflector paddles has a flexible wire frame covered by a cloth barrier material. In some implementations, the barrier element comprises at least one of a cloth material, a biocompatible material, bovine or porcine heart tissue, and a plastic membrane.

In some implementations, a valve repair system for repairing a native valve of a patient comprises a delivery sheath and a valve repair device that is deployable to a native valve of the patient by the delivery sheath;

In some implementations, the valve repair device comprises at least one anchor (e.g., a paddle, latch, clamp, gripper, fastener, etc.) and at least one leak control extension extending from a portion of the device, wherein the leak control extension is configured to block retrograde blood flow adjacent or near the device.

In some implementations, the at least one anchor is movable between an open position and a closed position, wherein the pair of paddles are configured to attach the valve repair device to the native valve of the patient;

In some implementations, the system (e.g., the valve repair device of the system) further comprises a coaption element (e.g., spacer, coaptation element, etc.).

In some implementations, the at least one leak control extension extends from the coaption element and is configured to block retrograde blood flow along sides of the coaption element.

In some implementations, the system (e.g., the valve repair device of the system) further comprises a cap that is connected to the coaption element.

In some implementations, the at least one leak control extension is connected directly to the coaption element.

In some implementations, the at least one leak control extension is connected to the cap that is connected to the coaption element.

In some implementations, the at least one leak control extension is pivotally attached to the cap.

In some implementations, the at least one anchor is coupled to the coaption element. In some implementations, the at least one anchor comprises a pair of paddles coupled to the coaption element.

In some implementations, the at least one anchor comprises a pair of paddles.

In some implementations, the coaption element is configured to close a gap in the native valve of the patient when the valve repair device is attached to the native valve.

In some implementations, the system further comprises at least one pair clasp, wherein the at least one anchor and the at least one clasp are configured to attach the valve repair device to the native valve of the patient. In some implementations, the at least one clasp is coupled to a cap of the device.

In some implementations, the at least one leak control extension comprises a deflector paddle having a flexible wire frame covered by a cloth barrier material. In some implementations, the deflector paddle is connected to the coaption element by one or more arms. In some implementations, the flexible wire frame is configured to deform when positioned against a wall within the native valve of the patient.

In some implementations, the at least one leak control extension comprises a pocket that includes a flexible wire frame that defines an opening of the pocket and a cloth barrier material that defines at least a portion of the interior of the pocket.

In some implementations, the opening of the at least one leak control extension is configured to be positioned below one or more leaflets of the native valve when the valve repair device is attached to the native valve.

In some implementations, the opening of the at least one leak control extension is configured to be positioned above a ventricular end of the one or more leaflets of the native valve when the valve repair device is attached to the native valve.

In some implementations, at least a portion of the leak control extension is configured to be positioned below a ventricular end of one or more leaflets of the native valve when the valve repair device is attached to the native valve.

In some implementations, the entire leak control extension is configured to be positioned above a ventricular end of one or more leaflets of the native valve when the valve repair device is attached to the native valve. In some implementations, the entire leak control extension is configured to be positioned below a ventricular end of one or more leaflets of the native valve when the valve repair device is attached to the native valve.

In some implementations, the at least one leak control extension comprises one or more deflector paddles and a barrier element. In some implementations, each of the one or more deflector paddles has a flexible wire frame covered by a cloth barrier material. In some implementations, the barrier element comprises at least one of a cloth material, a biocompatible material, bovine or porcine heart tissue, and a plastic membrane.

In some implementations, a method of repairing a native valve of a patient comprises attaching a spacer or coaption element between leaflets of the native valve of the patient and blocking retrograde blood flow through gaps between the spacer and the leaflets.

In some implementations, the retrograde blood flow through the gaps is blocked without filling the gaps.

In some implementations, the retrograde blood flow through the gaps is blocked without filling any portion of the gaps.

In some implementations, the retrograde blood flow is blocked by extensions that are at least partially disposed on a ventricular side of the leaflets.

In some implementations, the retrograde blood flow is blocked by extensions that are completely disposed on a ventricular side of the leaflets.

In some implementations, the method further comprises positioning the spacer to deform one or more of the extensions against a wall within the heart of the patient.

The above method(s) can be performed on a living animal or on a simulation, such as on a cadaver, cadaver heart, simulator (e.g. with the body parts, heart, tissue, etc. being simulated), etc.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of example embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which.

DETAILED DESCRIPTION

The following description refers to the accompanying drawings, which illustrate specific embodiments of the present disclosure. Other embodiments having different structures and operation do not depart from the scope of the present disclosure.

Example implementations of the present disclosure are directed to systems, devices, methods, etc. for repairing a defective heart valve. It should be noted that various embodiments of native valve repair devices, systems for delivery of native valve repair devices, and systems for removal of implanted native valve repair devices are disclosed herein, and any combination of these options can be made unless specifically excluded. In other words, individual components of the disclosed devices and systems can be combined unless mutually exclusive or otherwise physically impossible. Further, the techniques and methods can be performed on a living animal or on a simulation, such as on a cadaver, cadaver heart, simulator (e.g. with the body parts, heart, tissue, etc. being simulated), etc.

As described herein, when one or more components are described as being connected, joined, affixed, coupled, attached, or otherwise interconnected, such interconnection may be direct as between the components or may be indirect such as through the use of one or more intermediary components. Also, as described herein, reference to a “member,” “component,” or “portion” shall not be limited to a single structural member, component, or element but can include an assembly of components, members, or elements. Also, as described herein, the terms “substantially” and “about” are defined as at least close to (and includes) a given value or state (preferably within 10% of, more preferably within 1% of, and most preferably within 0.1% of).

Figure 1:
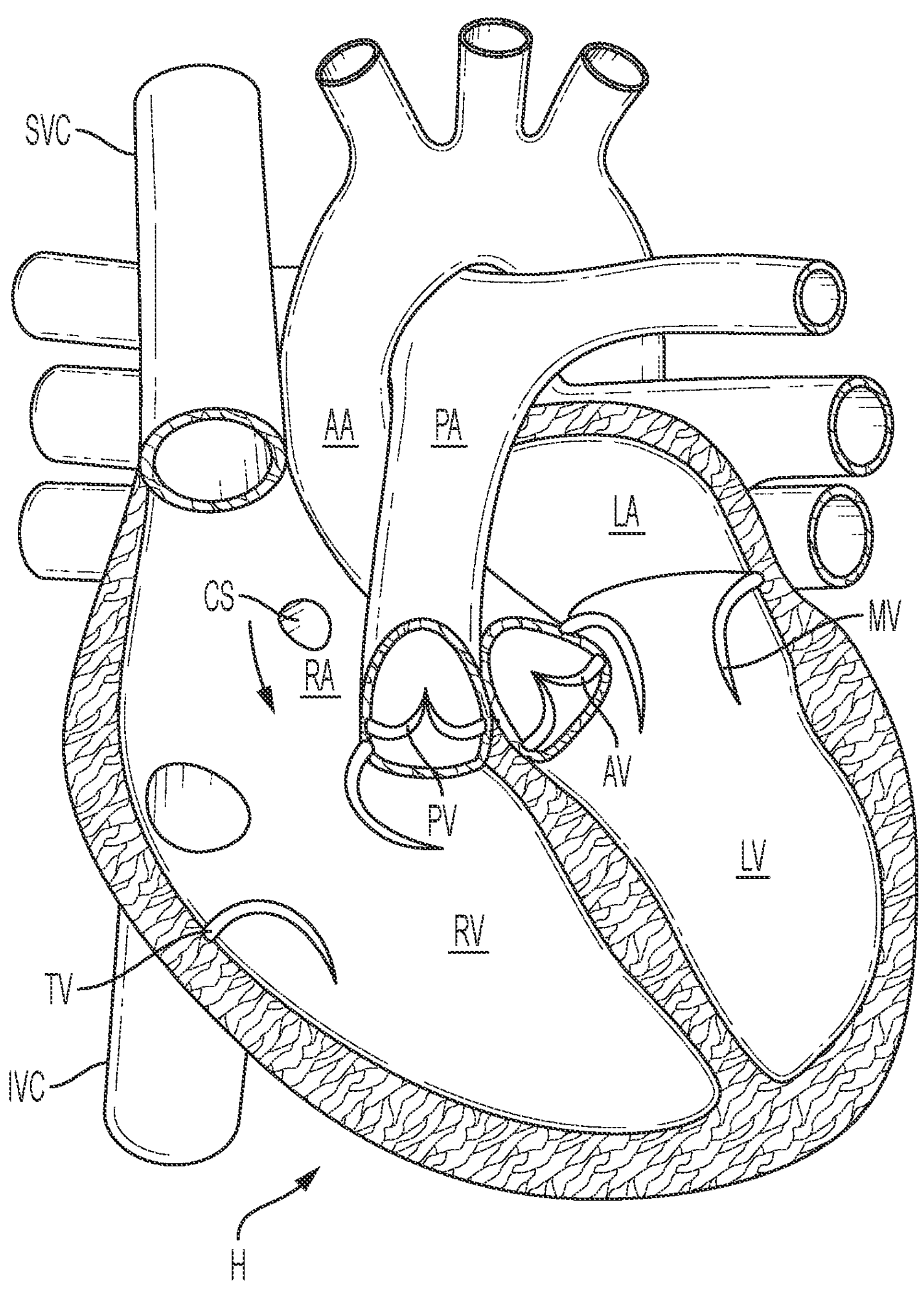
FIG. 1 illustrates a cutaway view of the human heart in a diastolic phase.
Figure 2:
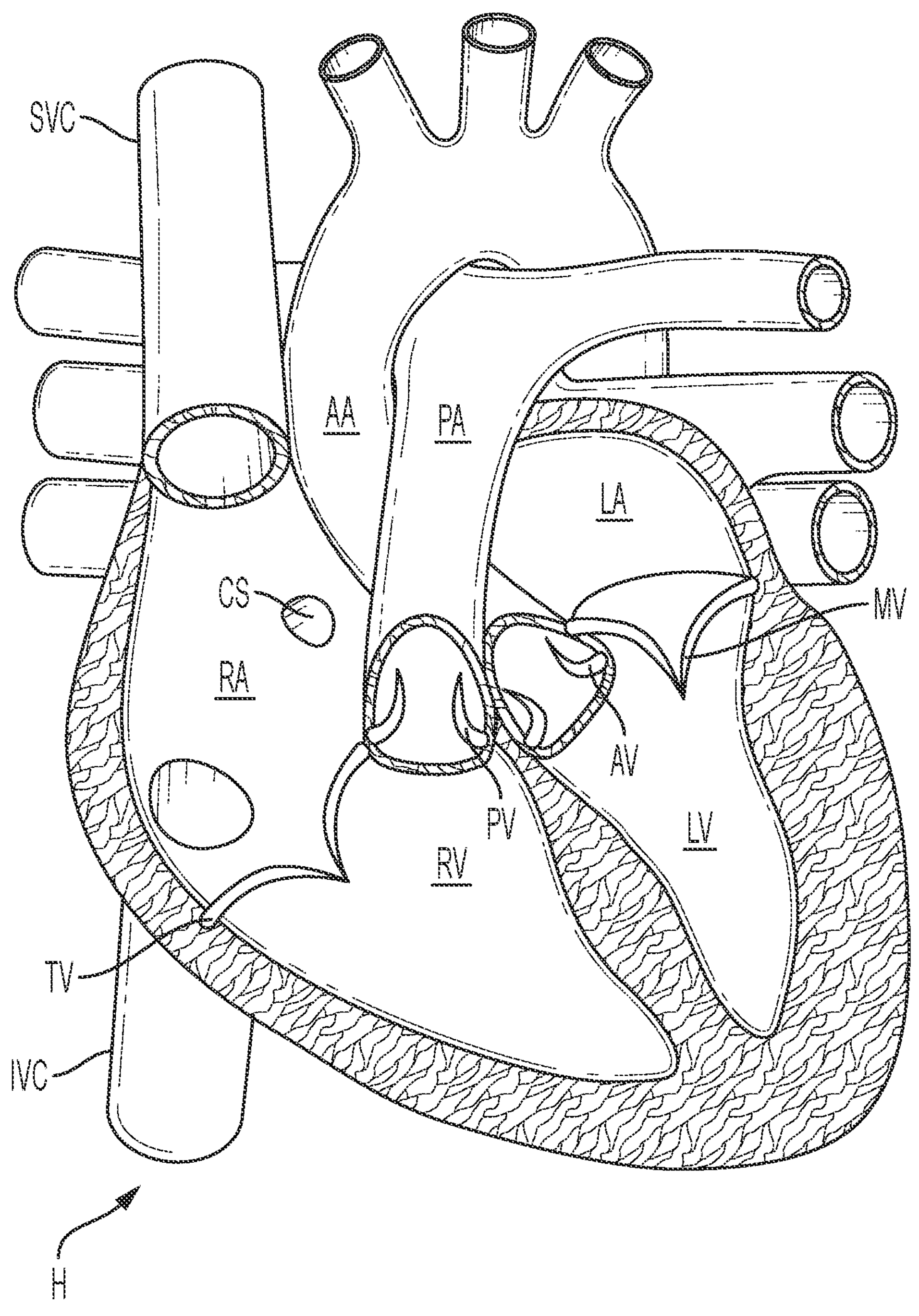
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or “coapt” in the flow stream to form the one-way, fluid-occluding surfaces. The native valve repair systems of the present application are described primarily with respect to the mitral valve MV. Therefore, anatomical structures of the left atrium LA and left ventricle LV will be explained in greater detail. However, the devices described herein can also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one example implementation, the devices described by the present application are used to repair the function of a defective mitral valve MV. That is, the devices are configured to help close the leaflets of the mitral valve to prevent blood from regurgitating from the left ventricle LV and back into the left atrium LA.

Figure 3:
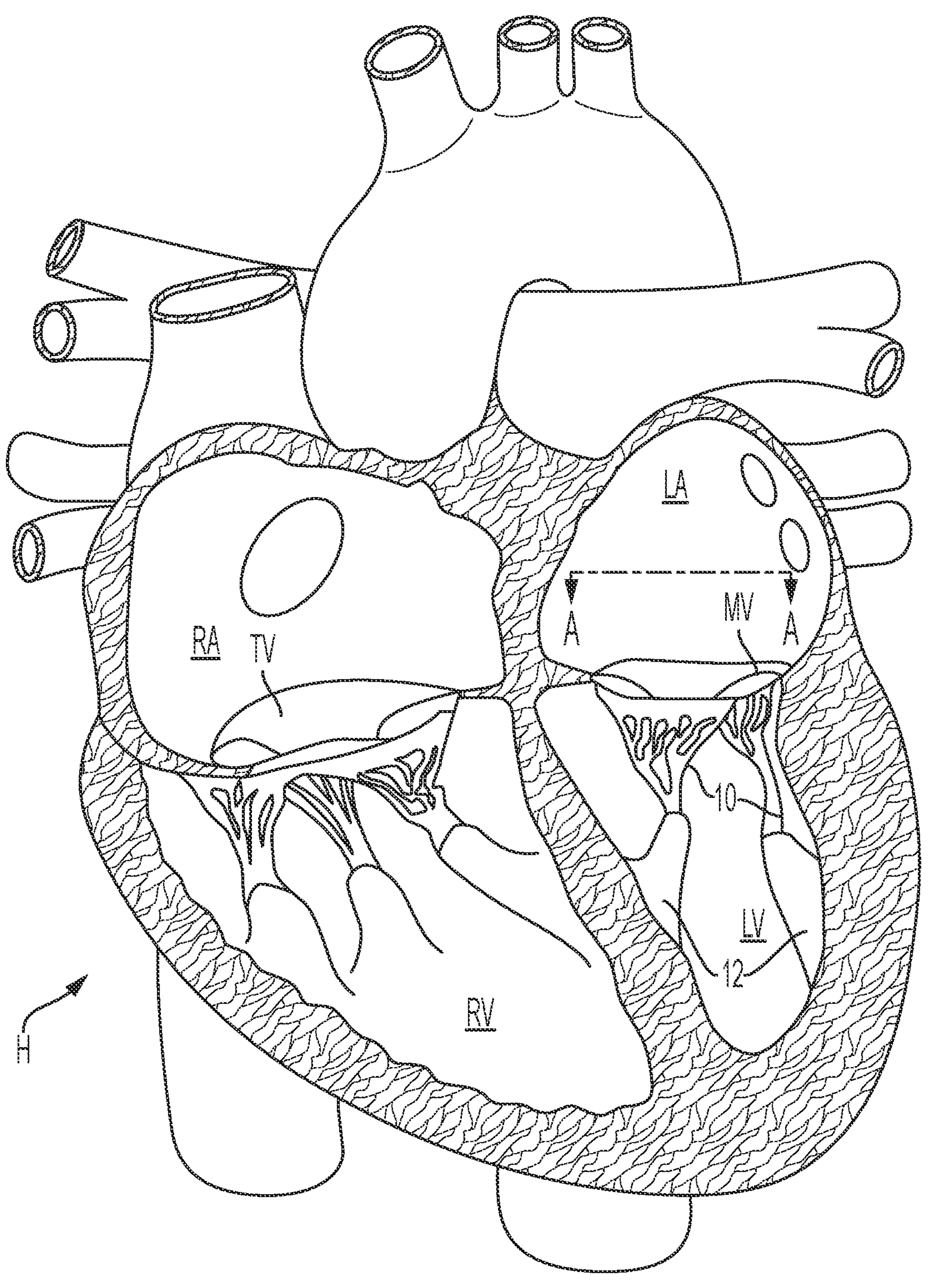
FIG. 3 illustrates a cutaway view of the human heart in a diastolic phase, in which the chordae tendineae are shown attaching the leaflets of the mitral and tricuspid valves to ventricle walls.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordae tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow’s Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve’s geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaptation. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (IIIb).

Figure 4:
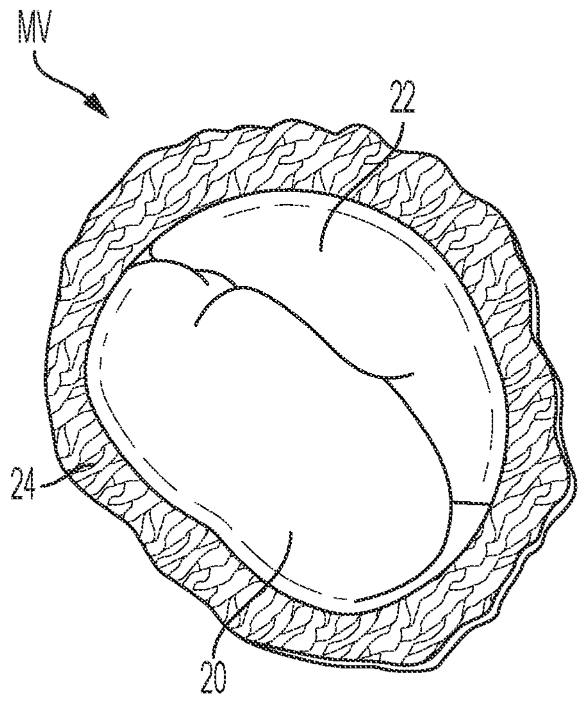
FIG. 4 illustrates a healthy mitral valve with the leaflets closed as viewed from an atrial side of the mitral valve.
Figure 5:
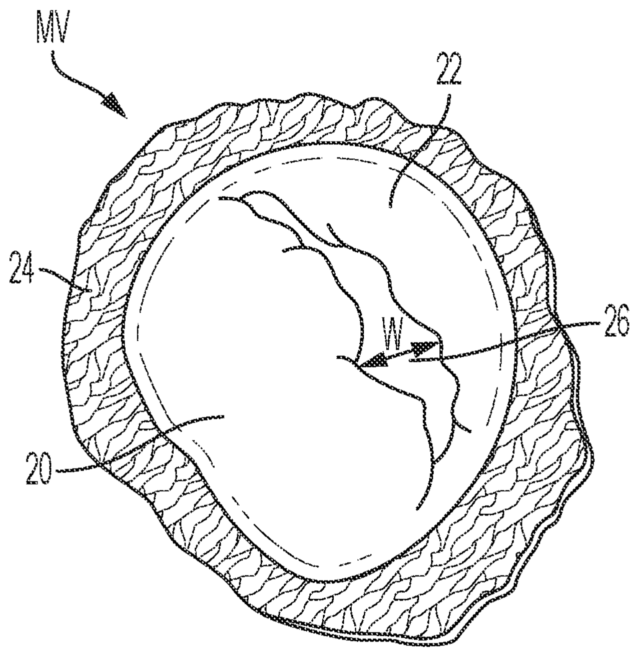
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 and/or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Figure 6:
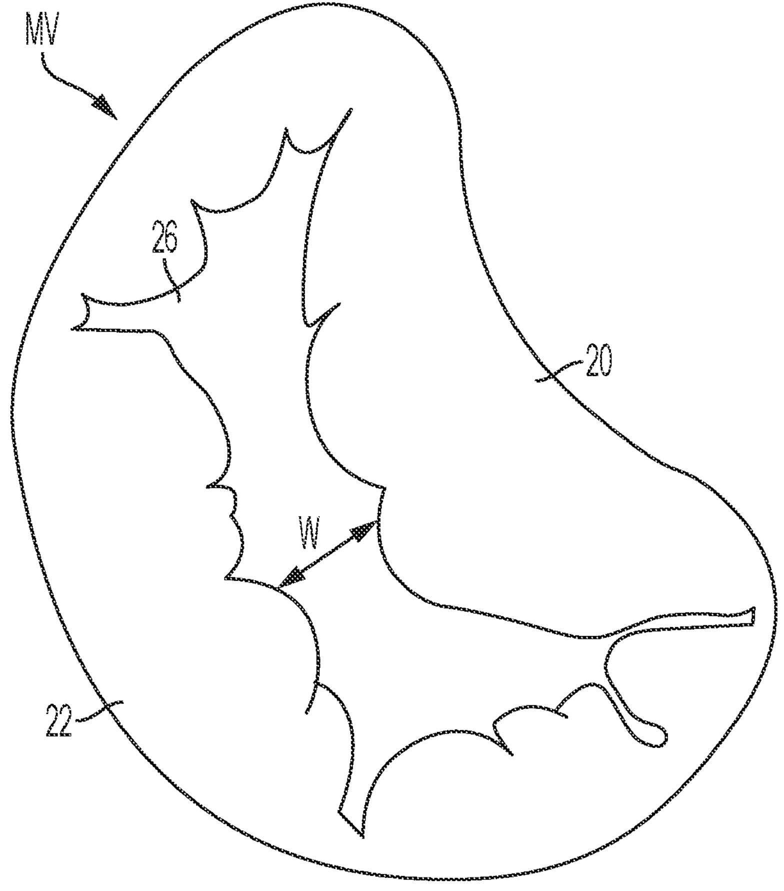
FIG. 6 illustrates a mitral valve having a wide gap between the posterior leaflet and the anterior leaflet.

Referring to FIG. 6, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 26 can have a width W greater than 15 mm. In any of the above-mentioned situations, a valve repair device is desired that is capable of engaging the anterior leaflet 20 and the posterior leaflet 22 to close the gap 26 and prevent regurgitation of blood through the mitral valve MV.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV can be repairable. In addition, regurgitation can occur due to the chordae tendineae 10 becoming dysfunctional (e.g., the chordae tendineae may stretch or rupture), which allows the anterior leaflet 20 and the posterior leaflet 22 to be reverted such that blood is regurgitated into the left atrium LA. The problems occurring due to dysfunctional chordae tendineae can be repaired by repairing the chordae tendineae or the structure of the mitral valve (e.g., by securing the leaflets 20, 22 at the affected portion of the mitral valve).

Figure 7:
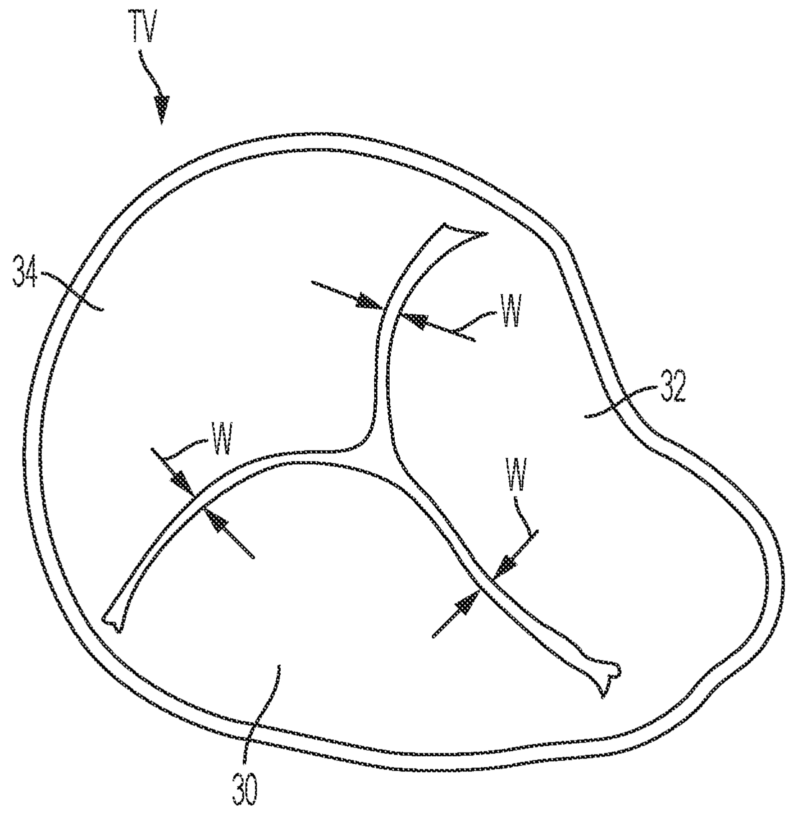
FIG. 7 illustrates a tricuspid valve viewed from an atrial side of the tricuspid valve.

The devices and procedures disclosed herein make reference to repairing the structure of a mitral valve or removing an implanted repair device from the mitral valve. However, it should be understood that the devices and concepts provided herein can be used to repair any native valve or any component of a native valve. Referring now to FIG. 7, any of the devices and concepts provided herein can be used to repair the tricuspid valve TV. For example, the devices and concepts provided herein can be used between any two of the anterior leaflet 30, septal leaflet 32, and posterior leaflet 34 to prevent regurgitation of blood from the right ventricle into the right atrium. In addition, any of the devices and concepts provided herein can be used on all three of the leaflets 30, 32, 34 together to prevent regurgitation of blood from the right ventricle to the right atrium. That is, the valve repair devices provided herein can be centrally located between the three leaflets 30, 32, 34.

The concepts disclosed in the present patent application can be applied to a variety of different valve repair devices. Some examples of valve repair devices that the concepts disclosed herein can be applied to are disclosed in U.S. Provisional Patent Application Ser. No. 62/744,031, filed on Oct. 10, 2018, Patent Cooperation Treaty Application No. PCT/US2019/012707, filed on Jan. 8, 2019, and Patent Cooperation Treaty No. PCT/US2018/028189 which are incorporated herein by reference in their entireties.

FIGS. 8-14 illustrate an example of a valve repair device. An example implantable prosthetic device can have a coaptation or coaption element (e.g., a spacer, etc.) and at least one anchor. The coaption element is configured to be positioned within the native heart valve orifice to help fill the space and form a more effective seal, thereby reducing or preventing regurgitation described above. The coaption element can have a structure that is impervious to blood and that allows the native leaflets to close around the coaption element during ventricular systole to block blood from flowing from the left or right ventricle back into the left or right atrium, respectively. The prosthetic device can be configured to seal against two or three native valve leaflets; that is, the device may be used in the native mitral (bicuspid) and tricuspid valves. The coaption element is sometimes referred to herein as a spacer because the coaption element can fill a space between improperly functioning native mitral or tricuspid leaflets that do not close completely.

The coaption element (e.g., spacer, etc.) can have various shapes. In some embodiments, the coaption element can have an elongated cylindrical shape having a round cross-sectional shape. In some embodiments, the coaption element can have an oval cross-sectional shape, a crescent cross-sectional shape, or various other non-cylindrical shapes. The coaption element can have an atrial portion positioned in or adjacent to the left atrium, a ventricular or lower portion positioned in or adjacent to the left ventricle, and a side surface that extends between the native mitral leaflets. In embodiments configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

The anchor can be configured to secure the device to one or both of the native mitral leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. In some embodiments, the anchor can attach to the coaption element at a location adjacent the ventricular portion of the coaption element. In some embodiments, the anchor can attach to a shaft or actuation wire or other actuation element, to which the coaption element is also attached. In some embodiments, the anchor and the coaption element can be positioned independently. In some embodiments, the anchor and the coaption element can be positioned simultaneously. The anchor can be configured to grasp the leaflets.

The prosthetic device can be configured to be implanted via a delivery sheath. Additional information regarding examples of delivery methods can be found in U.S. Pat. No. 8,449,599 and U.S. Patent Application Publication Nos. 2014/0222136, 2014/0067052, and 2016/0331523, each of which is incorporated herein by reference in its entirety. Further, these methods can be performed on a living animal or on a simulation, such as on a cadaver, cadaver heart, simulator (e.g. with the body parts, heart, tissue, etc. being simulated), etc. mutatis mutandis.

Referring now to FIGS. 8-14, an example of an implantable prosthetic device 100 schematically illustrated is shown in various stages of deployment. However, the implantable prosthetic device can take a wide variety of different forms as mentioned above. For example, the features of the present application can be included with any of the implantable prosthetic devices disclosed in U.S. Provisional Patent Application Ser. No. 62/744,031, Patent Cooperation Treaty Application No. PCT/US2019/012707, and/or Patent Cooperation Treaty No. PCT/US2018/028189. The device 100 can include any other features for an implantable prosthetic device discussed in the present application, and the device 100 can be positioned to engage valve tissue (e.g., leaflets 20, 22) as part of any suitable valve repair system (e.g., any valve repair system disclosed in the present application).

The device 100 can be deployed from a delivery sheath 102 and can include a coaption portion 104 and/or an anchor portion 106. The coaption portion 104 of the device 100 includes a coaption element or spacer 110 that is adapted to be implanted between the leaflets of the native valve (e.g., native mitral valve, native tricuspid valve, etc.) and is slidably attached to an actuation member or actuation element 112 (e.g., a wire, shaft, rod, line, suture, tether, etc.). The anchor portion 106 is actuatable between open and closed conditions and can take a wide variety of forms, such as, for example, paddles, latches, clasps, fasteners, gripping elements, or the like. Actuation of the actuation element 112 (e.g., actuation of an actuation wire, etc.) opens and closes the anchor portion 106 of the device 100 to grasp the mitral valve leaflets during implantation. The actuation element 112 can take a wide variety of different forms. For example, the actuation element can be threaded such that rotation of the actuation element moves the anchor portion 106 relative to the coaption portion 104. Or, the actuation element may be unthreaded, such that pushing or pulling the actuation element 112 moves the anchor portion 106 relative to the coaption portion 104.

In some implementations, the anchor portion 106 of the device 100 includes outer paddles 120 and inner paddles 122 that are connected between a cap 114 and the coaption element 110 by portions 124, 126, 128. The portions 124, 126, 128 can be jointed, hinged, and/or flexible to move between all of the positions described below. The interconnection of the outer paddles 120, the inner paddles 122, the coaption element 110, and the cap 114 by the portions 124, 126, and 128 can constrain the device to the positions and movements illustrated herein. In some implementations, the device includes only one outer paddle 120 and one inner paddle 122, and these can be configured in different ways.

The actuation member or actuation element 112 extends through the delivery sheath and/or a pusher tube/rod and/or the coaption element or spacer 110 to the cap 114 at the distal connection of the anchor portion 106. Extending and retracting the actuation element 112 increases and decreases the spacing between the coaption element 110 and the cap 114, respectively. An optional attaching means or collar (not shown) removably attaches the coaption element 110 to a pusher tube or rod and/or delivery sheath 102 so that the actuation element 112 slides along the actuation element 112 during actuation to open and close the paddles 120, 122 of the anchor portion 106. After the device 100 is connected to valve tissue, if the device 100 needs to be removed from the valve tissue, a retrieval device can be used to connect to the collar 115 such that the actuation element can extend through the collar 115 and the coaption element 110 to engage the anchor portion 106 to open the paddles 120, 122 and remove the device 100 from the valve tissue. Examples of retrieval devices that could be used are shown in PCT Application No. PCT/US2019/062391 filed Nov. 20, 2019, which is incorporated herein by reference in its entirety.

Figure 11:
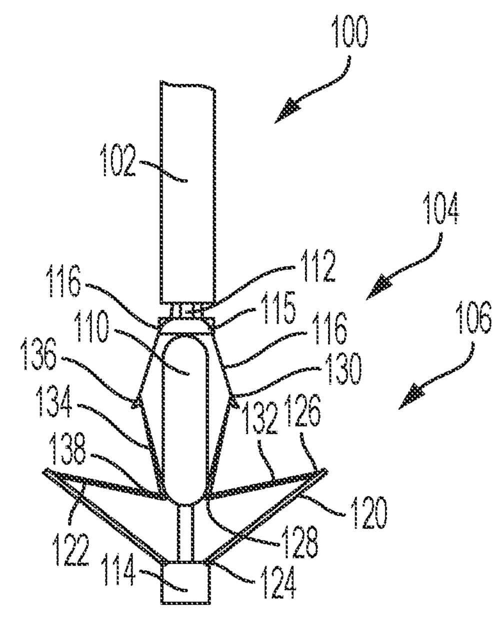

Referring now to FIG. 11, the anchor portion 106 includes attachment portions or gripping members. The illustrated gripping members are shown as barbed clasps 130 that include a base or fixed arm 132, a moveable arm 134, barbs 136, and a flex, hinge, or joint portion 138. Although, other friction-enhancing elements can be substituted for the barbs. The fixed arms 132 are attached to the inner paddles 122, with the flex, hinge, or joint portion 138 disposed proximate the coaption element 110. The barbed clasps have flat surfaces and do not fit in a recess of the paddle. Rather, the flat portions of the barbed clasps 130 are disposed against the surface of the inner paddle 122. The flex, hinge, or joint portion 138 provides a spring force between the fixed and moveable arms 132, 134 of the barbed clasp 130. The joint portion 138 can be any suitable flexible portion, hinge, or joint, such as a flexible joint or hinge, a spring joint or hinge, a pivot joint or hinge, or the like. In some embodiments, the flex, hinge, or joint portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the barbed clasps 130 and expose the barbs 136. The barbed clasps 130 are opened by applying tension to actuation lines 116 attached to the moveable arms 134, thereby causing the moveable arms 134 to move, flex, and/or pivot on the flex, hinge, or joint portions 138.

During implantation, the paddles 120, 122 are opened and closed to capture or grasp the native mitral valve leaflets between the paddles 120, 122 and the coaption element 110. The barbed clasps 130 further secure the native leaflets by engaging the leaflets with barbs 136 and pinching the leaflets between the moveable and fixed arms 134, 132. The barbs 136 of the barbed clasps 130 increase friction with the leaflets or may partially or completely puncture the leaflets. The actuation lines 116 can be actuated independently or separately so that each barbed clasp 130 can be opened and closed independently or separately. Separate/independent operation allows one leaflet to be grasped at a time, or for the repositioning of a clasp 130 on a leaflet that was insufficiently grasped, without altering a successful grasp on the other leaflet. The barbed clasps 130 not only open and close independent from each other but can fully be opened and closed independent from the position of the inner paddle 122, thereby allowing leaflets to be captured in a variety of positions as the particular situation requires.

The barbed clasps 130 can be opened independently or separately by pulling on an attached actuation line 116 (or other actuation means) that extends through the delivery sheath 102 to the barbed clasp 130. The actuation line 116 can take a wide variety of forms, such as, for example, a line, a suture, a wire, a rod, a catheter, or the like. The barbed clasps 130 can be spring loaded or otherwise biased so that in the closed position the barbed clasps 130 continue to provide a pinching force on the captured or grasped native leaflet. This pinching force can remain constant or positive regardless of the position of the inner paddles 122. Barbs 136 of the barbed clasps 130 can pierce the native leaflets to further secure the native leaflets.

Figures 8, 9, 10:
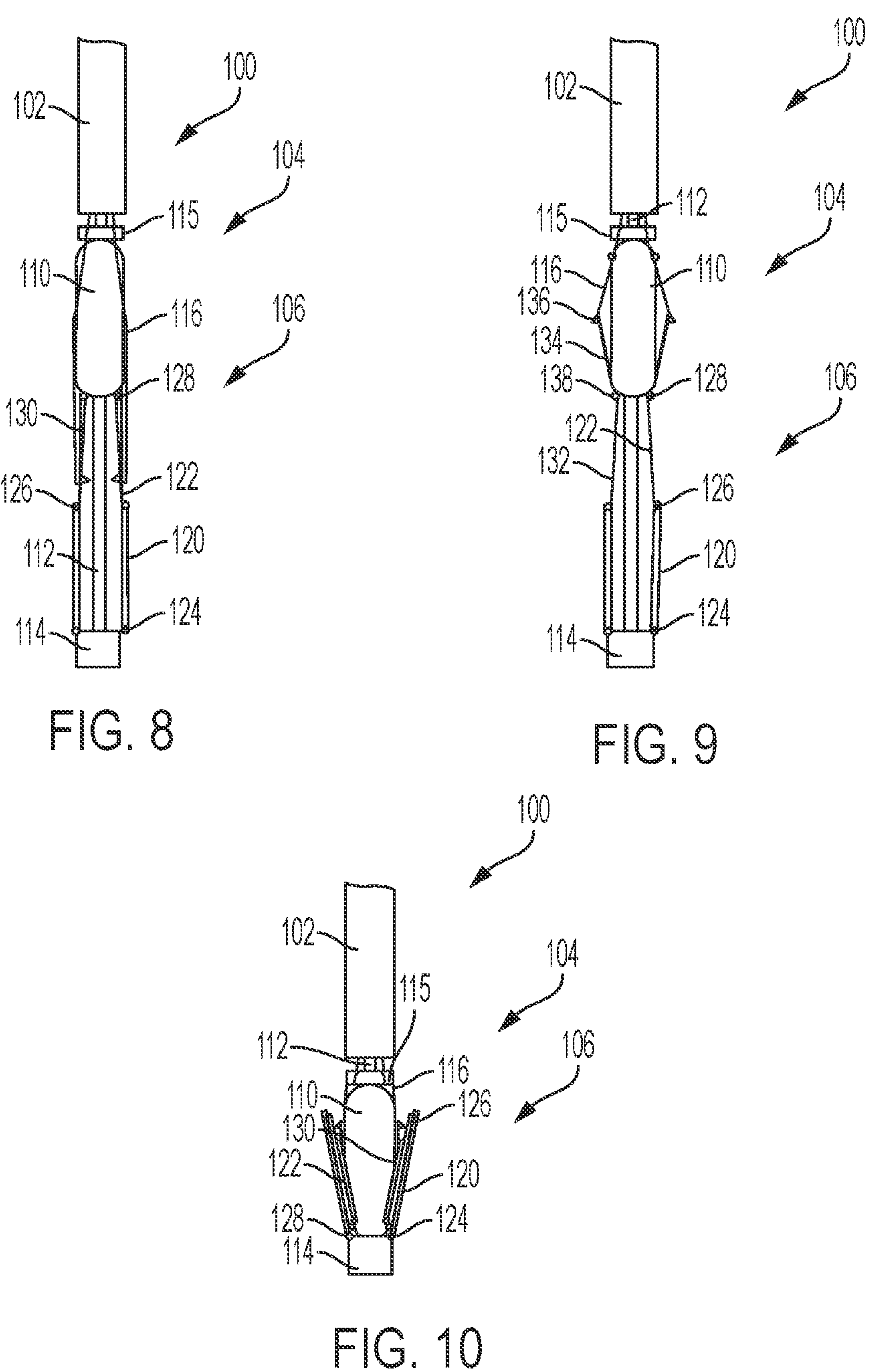
FIGS. 8-14 show an example of an implantable prosthetic device, in various stages of deployment.

Referring now to FIG. 8, the device 100 is shown in an elongated or fully open condition for deployment from the delivery sheath 102. The device 100 is loaded in the delivery sheath 102 in the fully open position, because the fully open position takes up the least space and allows the smallest catheter to be used (or the largest implantable device 100 to be used for a given catheter size). In the elongated condition the cap 114 is spaced apart from the coaption element 110 such that the paddles 120, 122 of the anchor portion 106 are fully open or fully extended. In some embodiments, an angle formed between the interior of the outer and inner paddles 120, 122 is approximately 180 degrees. The barbed clasps 130 are kept in a closed condition during deployment through the delivery sheath 102 so that the barbs 136 (FIG. 11) do not catch or damage the sheath or tissue in the patient's heart.

Referring now to FIG. 9, the device 100 is shown in an elongated detangling condition, similar to FIG. 8, but with the barbed clasps 130 in a fully open position, ranging from about 140 degrees to about 200 degrees, about 170 degrees to about 190 degrees, or about 180 degrees between fixed and moveable portions of the barbed clasps 130. Fully opening the paddles 120, 122 and the clasps 130 has been found to improve ease of detanglement from anatomy of the patient during implantation of the device 100.

Referring now to FIG. 10, the device 100 is shown in a shortened or fully closed condition. The compact size of the device 100 in the shortened condition allows for easier maneuvering and placement within the heart. To move the device 100 from the elongated condition to the shortened condition, the actuation element 112 is retracted to pull the cap 114 towards the coaption element 110. The joints, hinges, or flexible connections 126 between the outer paddle 120 and inner paddle 122 are limited or constrained in movement such that compression forces acting on the outer paddle 120 from the cap 114 being retracted towards the coaption element 110 cause the paddles 120, 122 or gripping elements to move radially outward. During movement from the open to closed position, the outer paddles 120 maintain an acute angle with the actuation element 112. The outer paddles 120 can optionally be biased toward a closed position. The inner paddles 122 during the same motion move through a considerably larger angle as they are oriented away from the coaption element 110 in the open condition and collapse along the sides of the coaption element 110 in the closed condition. In some embodiments, the inner paddles 122 are thinner and/or narrower than the outer paddles 120, and the joint, hinge, or flexible portions 126, 128 connected to the inner paddles 122 can be thinner and/or more flexible. For example, this increased flexibility can allow more movement than the joint, hinge, or flexible portion 124 connecting the outer paddle 124 to the cap 114. In some embodiments, the outer paddles 120 are narrower than the inner paddles 122. The joint or flexible portions 126, 128 connected to the inner paddles 122 can be more flexible, for example, to allow more movement than the joint or flexible portion 124 connecting the outer paddle 124 to the cap 114. In some embodiments, the inner paddles 122 can be the same width or substantially the same width as the outer paddles.

Figure 12:
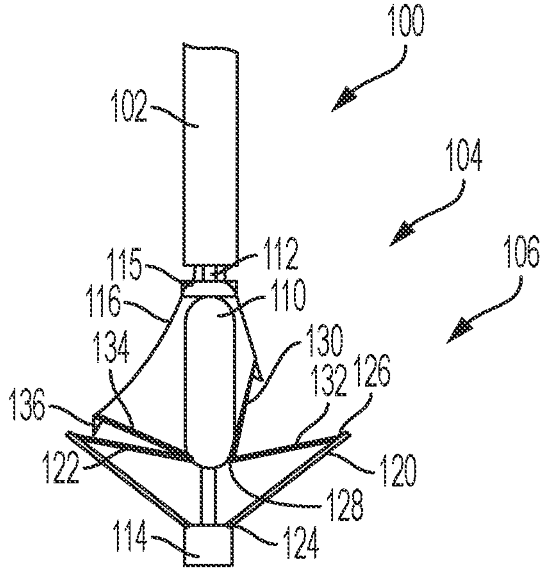
Figures 13, 14:
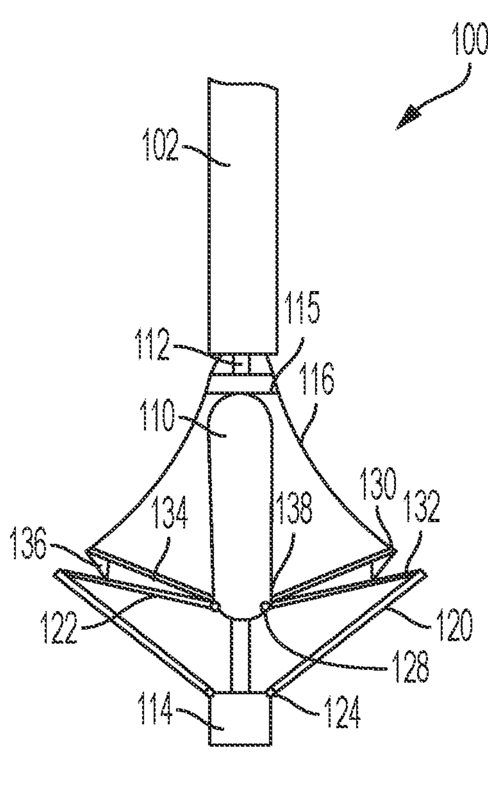

Referring now to FIGS. 11-13, the device 100 is shown in a partially open, capture-ready or grasp-ready condition. To transition from the fully closed to the partially open condition, the actuation element 112 (e.g., and actuation wire, actuation shaft, etc.) is extended to push the cap 114 away from the coaption element 110, thereby pulling on the outer paddles 120, which in turn pull on the inner paddles 122, causing the anchor portion 106 to partially unfold. The actuation lines 116 are also retracted to open the clasps 130 so that the leaflets can be captured or grasped. In some embodiments, like the example illustrated by FIG. 11, the pair of inner and outer paddles 122, 120 are moved in unison, rather than independently, by a single actuation element 112. Also, the positions of the clasps 130 may be dependent on the positions of the paddles 122, 120. For example, referring to FIG. 10 closing the paddles 122, 120 can also close the clasps. In some embodiments, the paddles 120, 122 can be independently controllable. For example, the device 100 can have two actuation elements and two independent caps, such that one independent wire and cap are used to control one paddle, and the other independent wire and cap are used to control the other paddle.

Referring now to FIG. 12, one of the actuation lines 116 is extended to allow one of the clasps 130 to close. Referring now to FIG. 13, the other actuation line 116 is extended to allow the other clasp 130 to close. Either or both of the actuation lines 116 may be repeatedly actuated to repeatedly open and close the barbed clasps 130.

Referring now to FIG. 14, the device 100 is shown in a fully closed and deployed condition. The delivery sheath 102 and actuation element 112 are retracted, and the paddles 120, 122 and clasps 130 remain in a fully closed position. Once deployed, the device 100 can be maintained in the fully closed position with a mechanical latch or can be biased to remain closed through the use of spring materials, such as steel, other metals, plastics, composites, etc. or shape-memory alloys such as Nitinol. For example, the jointed, hinged, or flexible portions 124, 126, 128, 138, and/or the inner and outer paddles 122, and/or an additional biasing component can be formed of metals such as steel or shape-memory alloy, such as Nitinol—produced in a wire, sheet, tubing, or laser sintered powder—and can biased to hold the outer paddles 120 closed around the coaption element or spacer 110 and the barbed clasps 130 pinched around native leaflets. In some embodiments, the paddles 120, 122 can be configured to open and close with the beating of the heart and corresponding opening and closing of the native valve.

Figure 15:
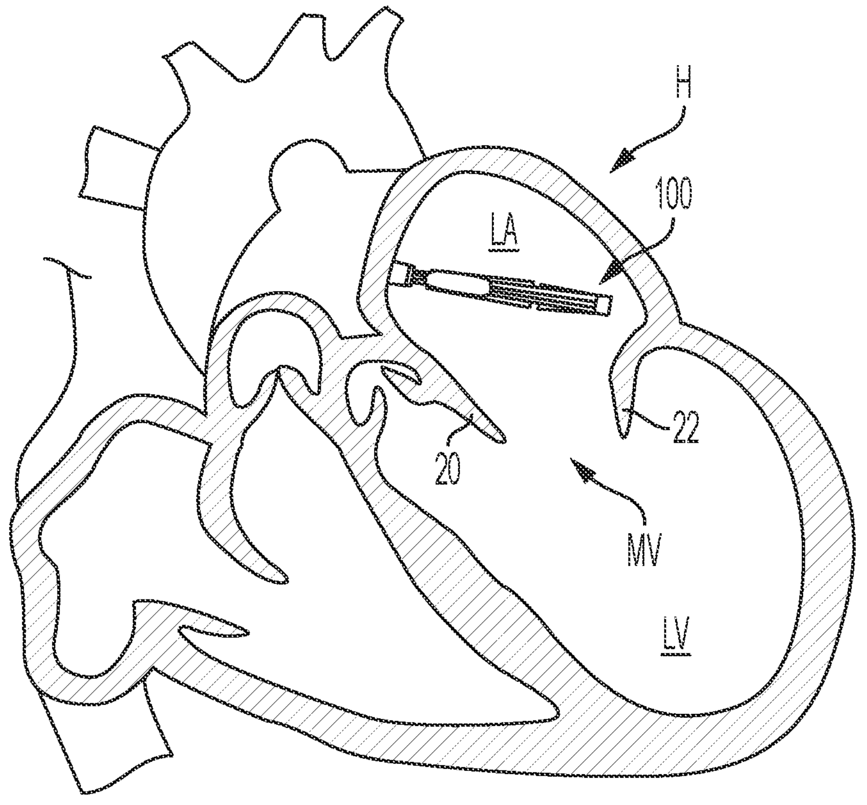
FIGS. 15-20 show the implantable prosthetic device of FIGS. 8-14 being delivered and implanted within a native valve.
Figure 16:
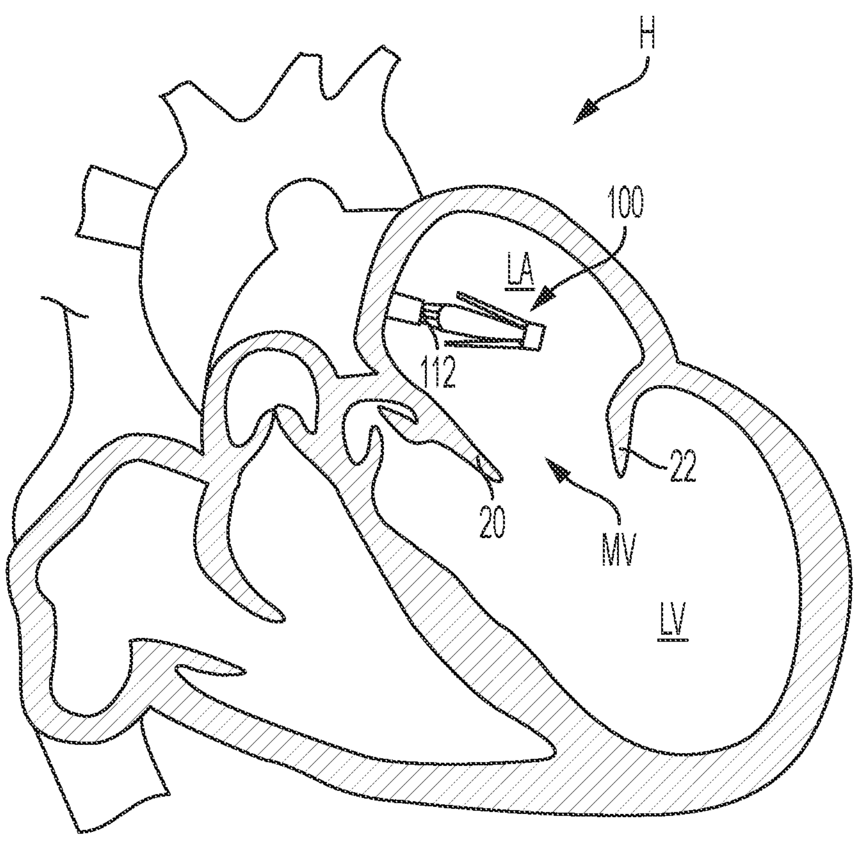
Figure 17:
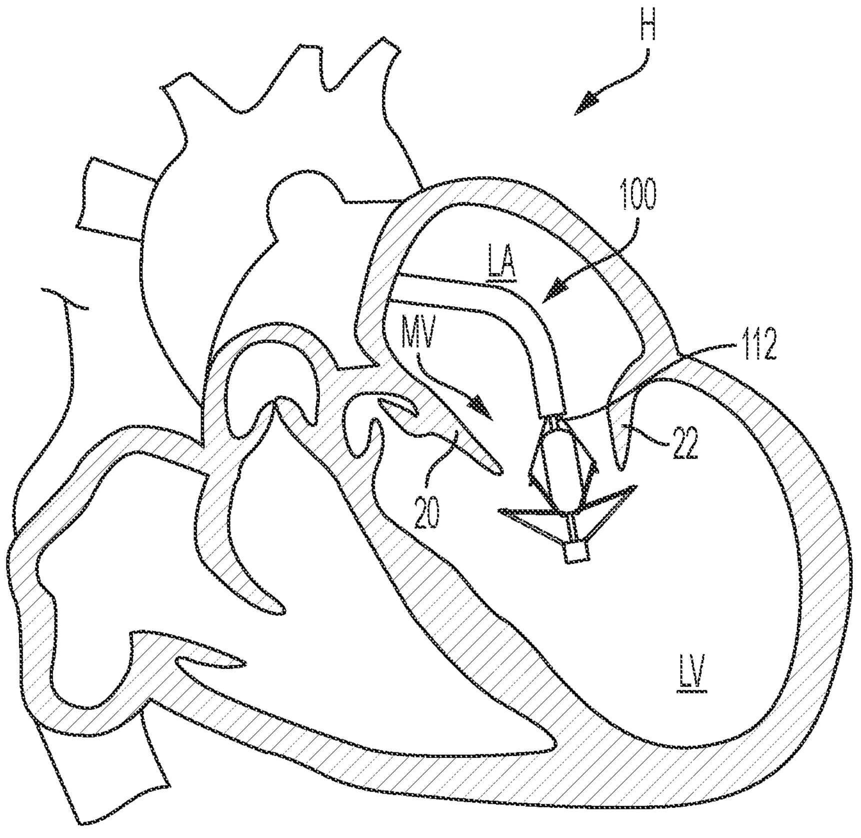
Figure 18:
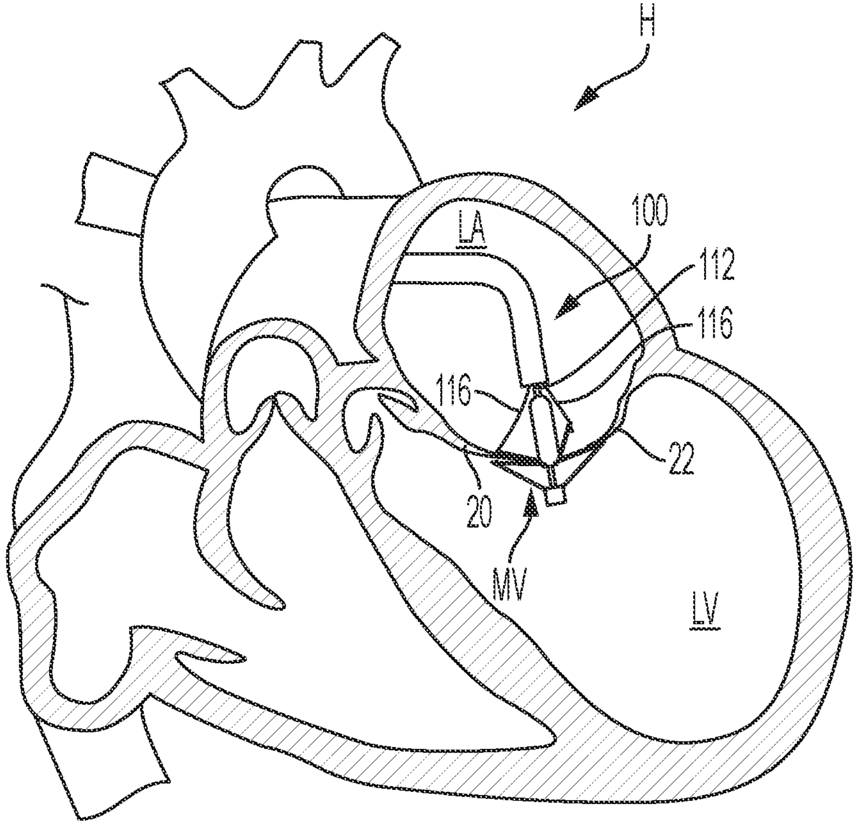
Figure 19:
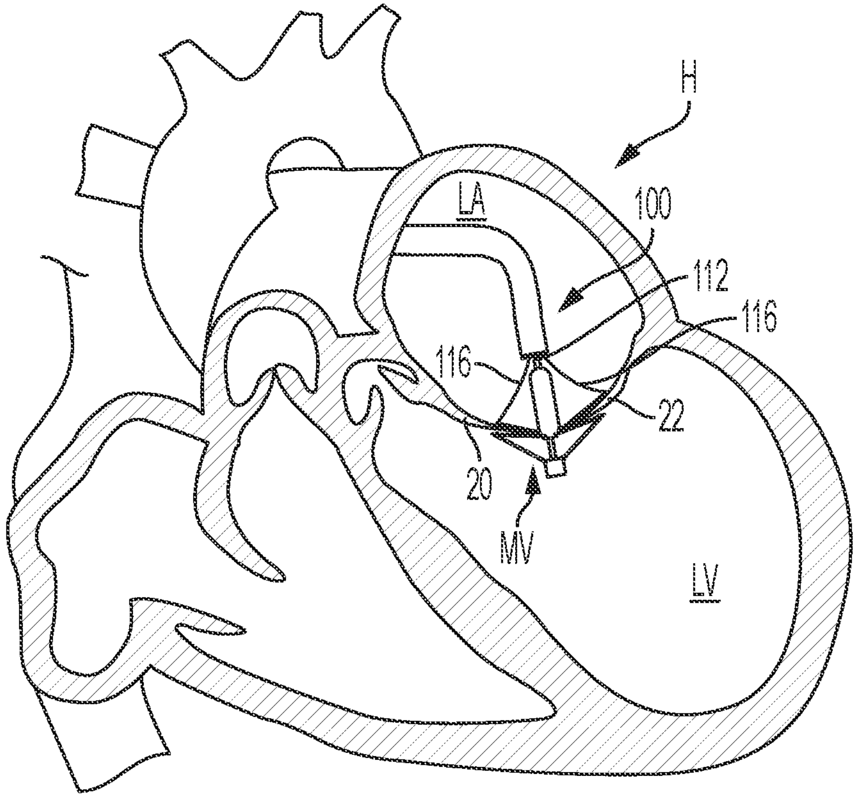
Figure 20:
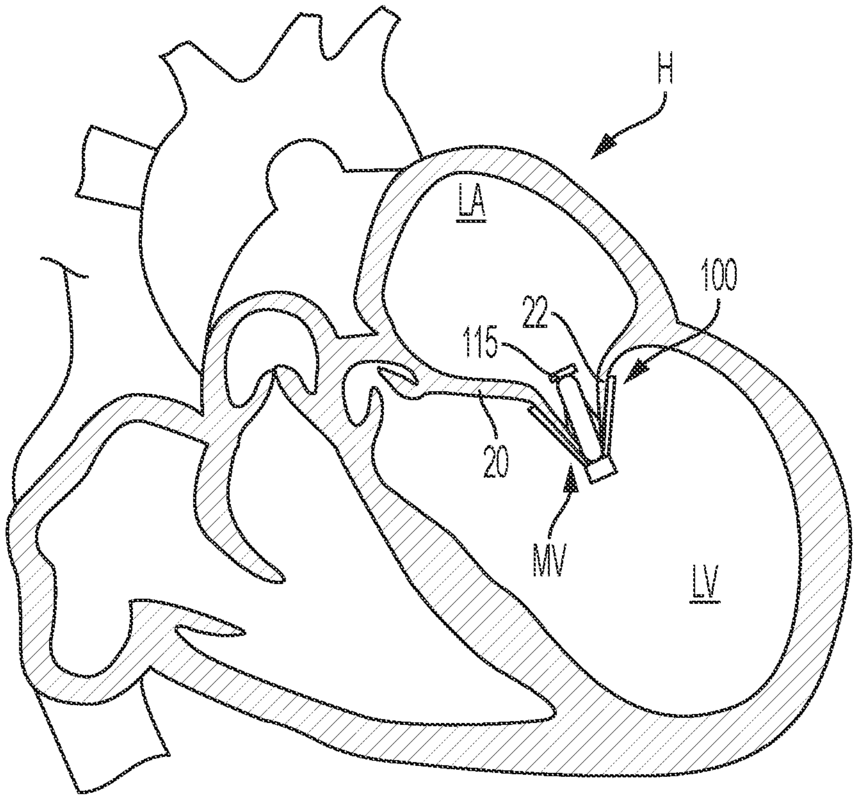

Referring now to FIGS. 15-20, the implantable device 100 of FIGS. 8-14 is shown being delivered and implanted within the native mitral valve MV of the heart H. Referring now to FIG. 15, the delivery sheath is inserted into the left atrium LA through the septum and the device 100 is deployed from the delivery sheath in the fully open condition. The actuation element 112 is then retracted to move the device 100 into the fully closed condition shown in FIG. 16. As can be seen in FIG. 17, the device 100 is moved into position within the mitral valve MV into the ventricle LV and partially opened so that the leaflets 20, 22 can be captured or grasped. Referring now to FIG. 18, an actuation line 116 is extended to close one of the clasps 130, capturing a leaflet 20. FIG. 19 shows the other actuation line 116 being then extended to close the other clasp 130, capturing the remaining leaflet 22. Lastly, as can be seen in FIG. 20, the delivery sheath 102 and actuation element 112 and actuation lines 116 are then retracted and the device 100 is fully closed and deployed in the native mitral valve MV.

Figure 21:
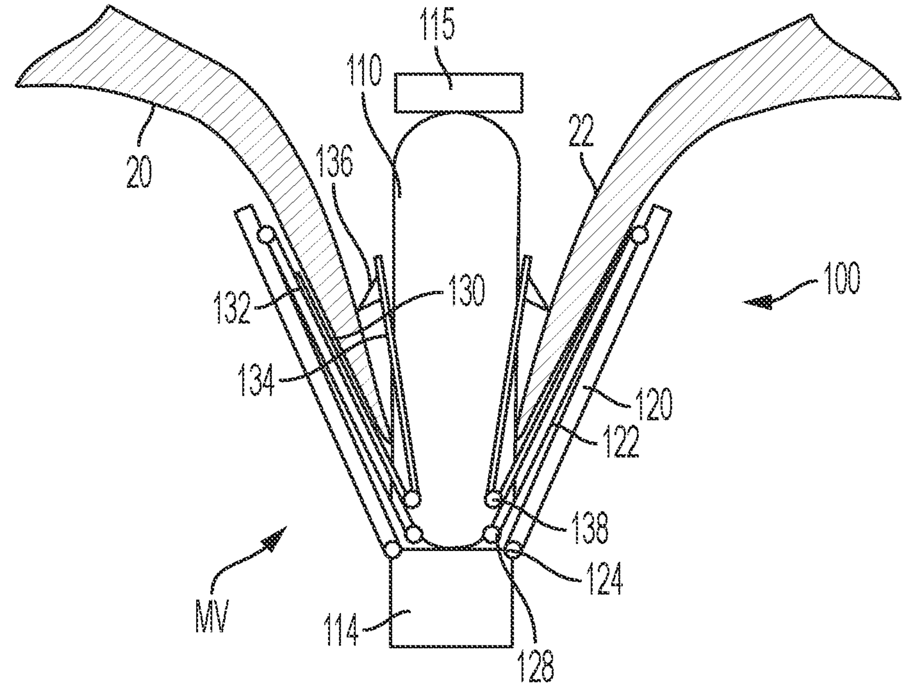
FIG. 21 shows the implantable prosthetic device of FIGS. 8-14 implanted within a native valve.
Figure 22:
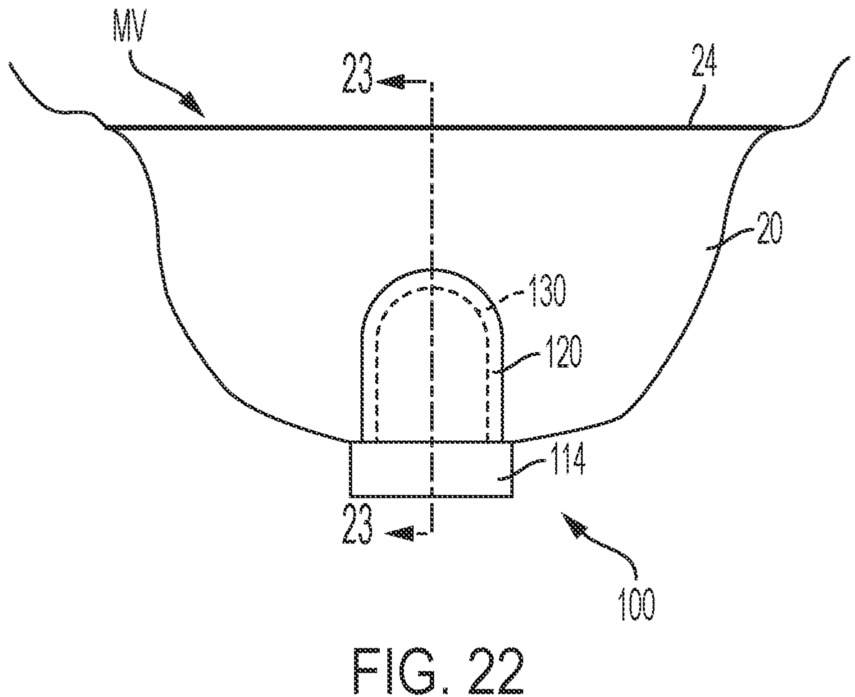
FIG. 22 shows an implantable prosthetic device implanted in a first example position within a native valve.
Figure 23:
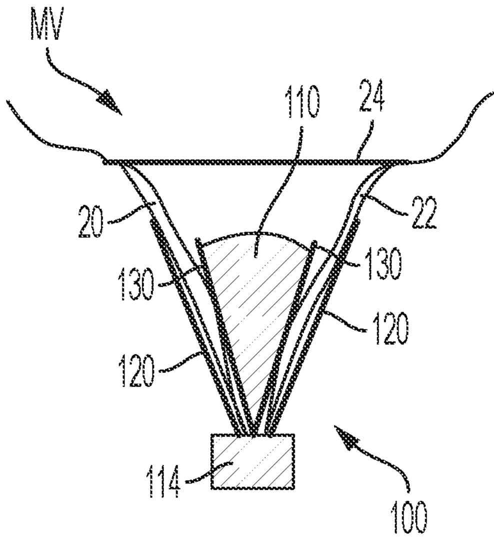
FIG. 23 is a cross-sectional view of the implantable prosthetic device implanted in the first position within the native valve shown in FIG. 22, with the section taken along the plane indicated by line 23-23 in FIG. 22.

Referring now to FIG. 21, the device 100 of FIGS. 8-14 is shown implanted within a native valve, e.g., native mitral valve MV, in the fully closed position. The implanted device 100 has outer paddles 120, inner paddles 122, clasps 130, a coaption element 110 (e.g., a spacer, etc.), and a cap 114. The outer paddles 120 and the inner paddles 122 are connected between the cap 114 and the coaption element 110 by portions 124, 126, 128 (which can be jointed and/or flexible to move between various positions). The coaption element 110 is adapted to be implanted between the leaflets 20, 22 of the native valve. The clasps 130 are configured to connect device 100 to the leaflets 20, 22. In some embodiments, the clasps 130 include a fixed arm that is attached to the inner paddle 122 and a movable arm 134 that has a friction-enhancing element (e.g., barb, ridges, rough surface, adhesive, etc.) for engaging the leaflets 20, 22 of the native valve. In some implementations, the device 100 has only one outer paddle 120, only one inner paddle 122, and only one clasp (e.g., a barbed clasp, etc.), and these can be configured in different ways.

Referring to FIGS. 22-27, an implantable prosthetic device 100 is attached to the leaflets 20, 22 of a native valve (illustrated, for example, as mitral valve MV, but could be similarly used on another valve such as the tricuspid valve) in the fully closed position. In the embodiment shown in FIGS. 22-25, the implantable prosthetic device 100 is attached to the native valve at a substantially central location within the annulus 24. It should be understood, however, that the implantable prosthetic device 100 can be attached to the leaflets 20, 22 at any location within the native valve (e.g., the location shown in FIGS. 26-27). The device 100 is shown as having a pair of paddles 120, a pair of clasps 130, a coaption element 110, and a cap 114. However, the implantable prosthetic device 100 can take any suitable form, such as, for example, any formed described in the present application.

Figure 24:
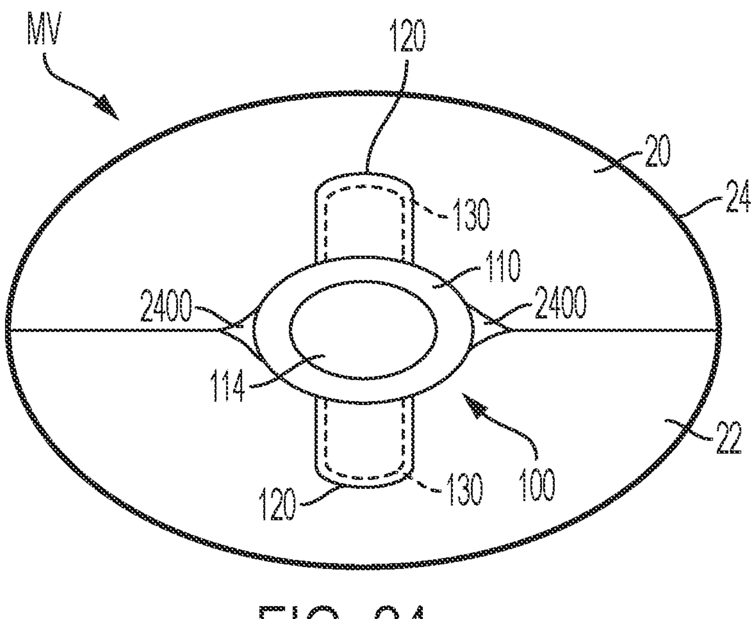
FIG. 24 shows the implantable prosthetic device implanted in the first position within the native valve shown in FIG. 22, viewed from the ventricle side of the native valve.
Figure 25:
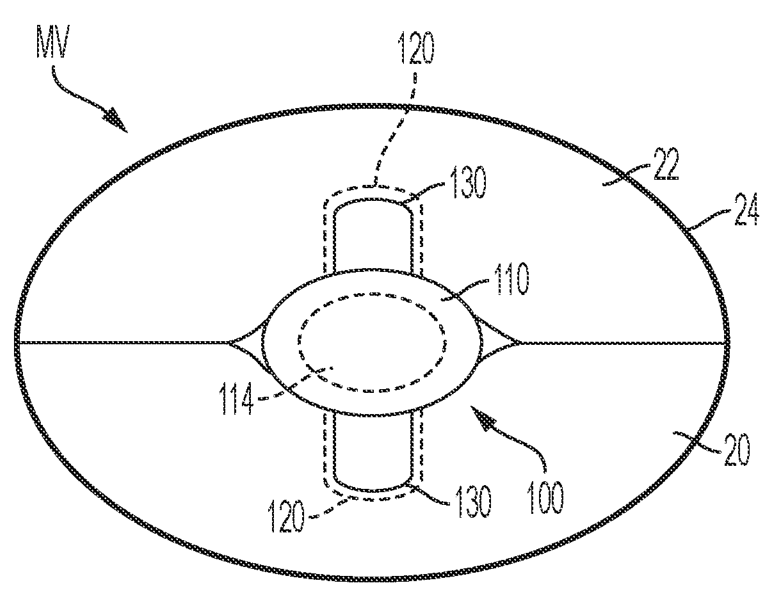
FIG. 25 shows the implantable prosthetic device implanted in the first position within the native valve shown in FIG. 22, viewed from the atrial side of the native valve.

Referring to FIGS. 24 and 25, during the systolic phase, the leaflets 20, 22 coapt around the implantable prosthetic device 100 to prevent regurgitation of blood from the left ventricle to the left atrium. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. These openings 2400 allow for blood to regurgitate into the left atrium during the systolic phase.

Figures 26, 27:
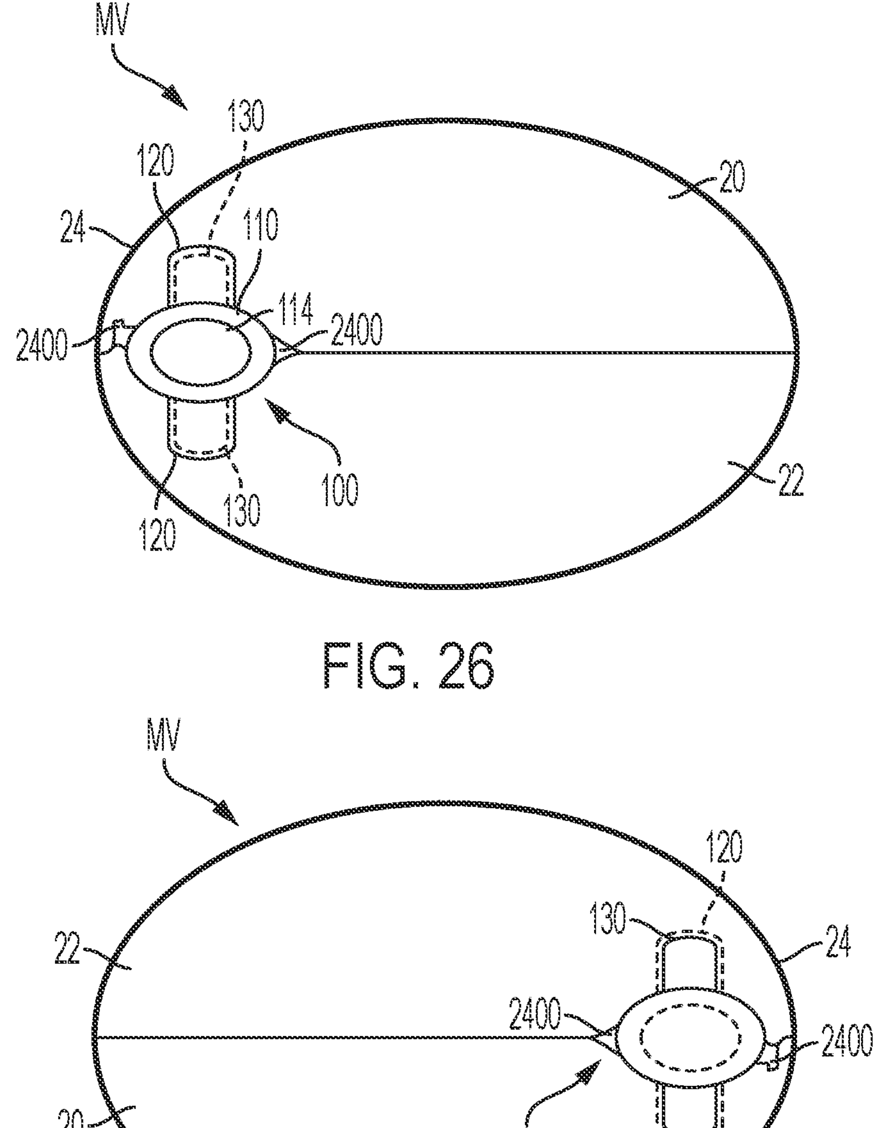
FIG. 26 shows the implantable prosthetic device of FIG. 22 implanted in a second example position within the native valve, viewed from the ventricle side of the native valve.
FIG. 27 shows the implantable prosthetic device of FIG. 22 implanted in the second example position within the native valve shown in FIG. 26, viewed from the atrial side of the native valve.

Referring to FIGS. 26 and 27, the device 100 can be placed within the native valve or mitral valve MV in a location near the annulus 24. Similar to the device 100 being located in a more central location within the mitral valve MV (as shown in FIGS. 24 and 25), openings 2400 may form where both leaflets 20, 22 and the device 100 meet. As shown in the illustrated embodiment, when the device 100 is placed near the annulus 24 the force on the mitral valve MV by the device 100 may cause the portions of the leaflets adjacent to the annulus 24 to bunch up or pucker and may cause an opening 2400 have a deformed shape. For example, when the device 100 is placed near the annulus, it is more difficult to align the leaflets in the device. When the leaflets are offset from one another in the device 100, the portions of the leaflets adjacent to the annulus 24 may bunch up or pucker and may cause an opening 2400 with a deformed shape on one or both sides of the device.

Figure 28:
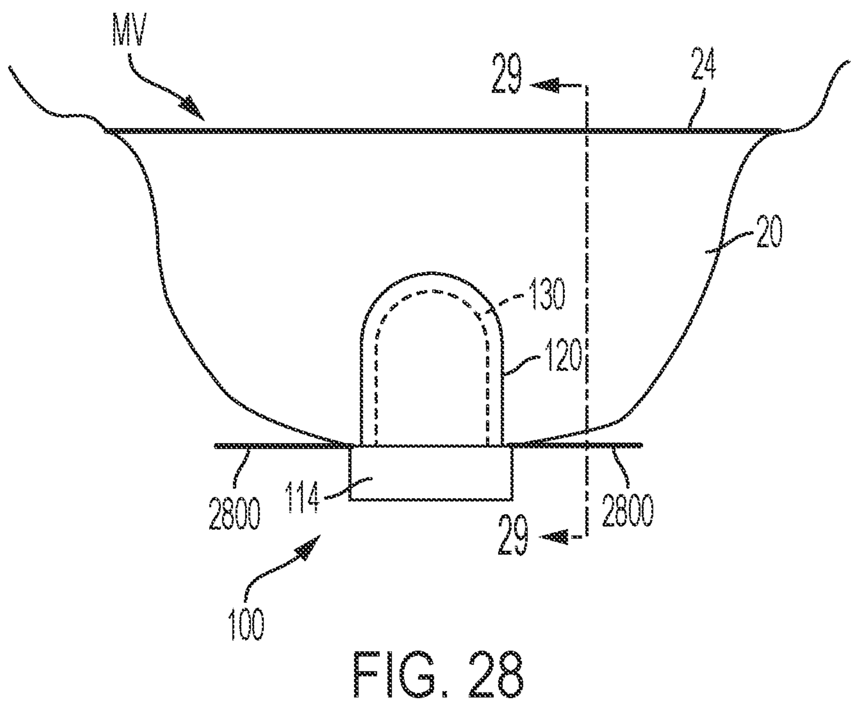
FIG. 28 shows an example of an implantable prosthetic device implanted in a first example position within the native valve.
Figures 90, 91:
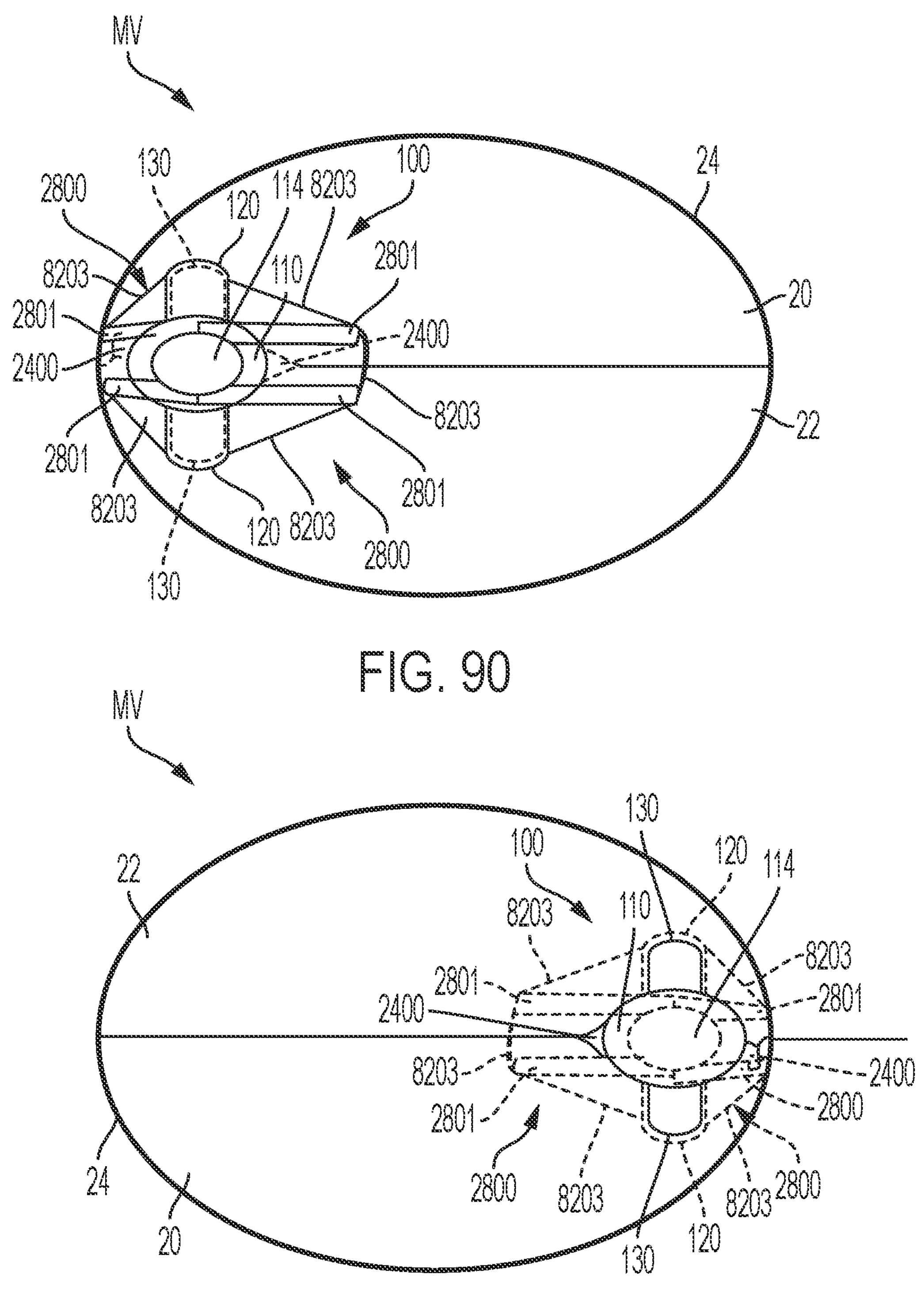
FIG. 90 shows the implantable prosthetic device of FIG. 82 implanted in a second example position within the native valve, viewed from the ventricle side of the native valve.
FIG. 91 shows the implantable prosthetic device of FIG. 82 implanted in the second example position within the native valve shown in FIG. 90, viewed from the atrial side of the native valve.

FIGS. 28-91 show various embodiments of an implantable prosthetic device 100 that includes one or more leak control mechanisms or leak control extensions 2800, where the leak control extensions 2800 allow blood to flow past or over the leak control extensions 2800 when the heart is in the diastolic phase (i.e. blood flow from the atrium to the ventricle) and that blocks or deflects at least a portion of blood flow that would otherwise regurgitate through the openings 2400 when the heart is in the systolic phase (i.e. blood flow from the ventricle to the atrium). The leak control extension 2800 can take a wide variety of different forms. For example, the leak control extension 2800 can have the configuration of a substantially flat deflecting paddle, a curved deflecting paddle, a bag or sack that opens toward the cap, a deflecting paddle and cloth assembly, and the like. The leak control extensions 2800 can be made from a wide variety of different materials. For example, the leak control extensions can be made from thin plastic, a wire frame with a cloth covering, cloth without a frame, cloth with a plastic frame, any combination thereof, etc. The leak control extensions 2800 can be positioned in a wide variety of different ways. For example, the leak control extensions can be positioned at the bottom of the native valve leaflets, below the bottom of the native valve leaflets, between the bottom of the native valve leaflets and the native valve annulus, or such that a portion of the leak control extension is below the native valve leaflets and a portion of the leak control extension is between the bottom of the native valve leaflets and the native valve annulus.

FIGS. 28-37 show an example of an implantable prosthetic device 100 attached to the leaflets 20, 22 of a native valve (illustrated, for example, as mitral valve MV, but could be similarly used on another valve such as the tricuspid valve) in the fully closed position, where the device 100 includes one or more leak control extensions 2800. In the embodiment shown in FIGS. 28-35, the implantable prosthetic device 100 is attached to the native valve at a substantially central location relative to the annulus 24. It should be understood, however, that the implantable prosthetic device 100 can be attached to the leaflets 20, 22 at any location within the native valve (e.g., the location shown in FIGS. 36-37). The device 100 has a pair of paddles 120, a pair of clasps 130, a coaption element 110 (e.g., a spacer, etc.), a cap 114, and leak control extensions 2800. However, the implantable prosthetic device 100 can take any suitable form, such as, for example, any form described in the present application, any of the implantable prosthetic devices disclosed in U.S. Provisional Patent Application Ser. No. 62/744,031, Patent Cooperation Treaty Application No. PCT/US2019/012707, and/or Patent Cooperation Treaty No. PCT/US2018/028189 in combination with the leak control extensions 2800.

Figure 29:
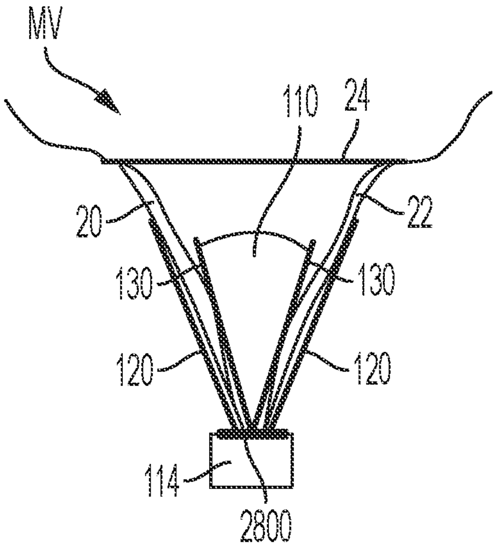
FIG. 29 is a cross-sectional view of the implantable prosthetic device implanted in the first position within the native valve shown in FIG. 28, with the section taken along the plane indicated by line 29-29 in FIG. 28.

In the example illustrated by FIGS. 28 and 29, the leak control extensions 2800 include deflecting paddles 2801 connected to the top surface of the cap 14 and positioned below the native valve leaflets. The leak control extension(s) 2800 are configured to block blood from the ventricle from reaching the opening 2400 during the systolic phase. That is, the leak control extension(s) 2800 extend from the device (e.g., from the cap 114 of the device 100) such that the leak control extensions are positioned to prevent blood from moving through any jets or openings between the leaflets 20, 22 of the native valve during the systolic phase. In the illustrated embodiment, the leak control extensions 2800 are positioned in the left ventricle LV when the device 100 is attached to the leaflets 20, 22. In the illustrated embodiment, the device 100 has two leak control extensions 2800 that are attached to a top surface of the cap 14. While the illustrated embodiment is shown as having two leak control extensions 2800, it should be understood that the device 100 can have any suitable number of leak control extensions.

Figure 30:
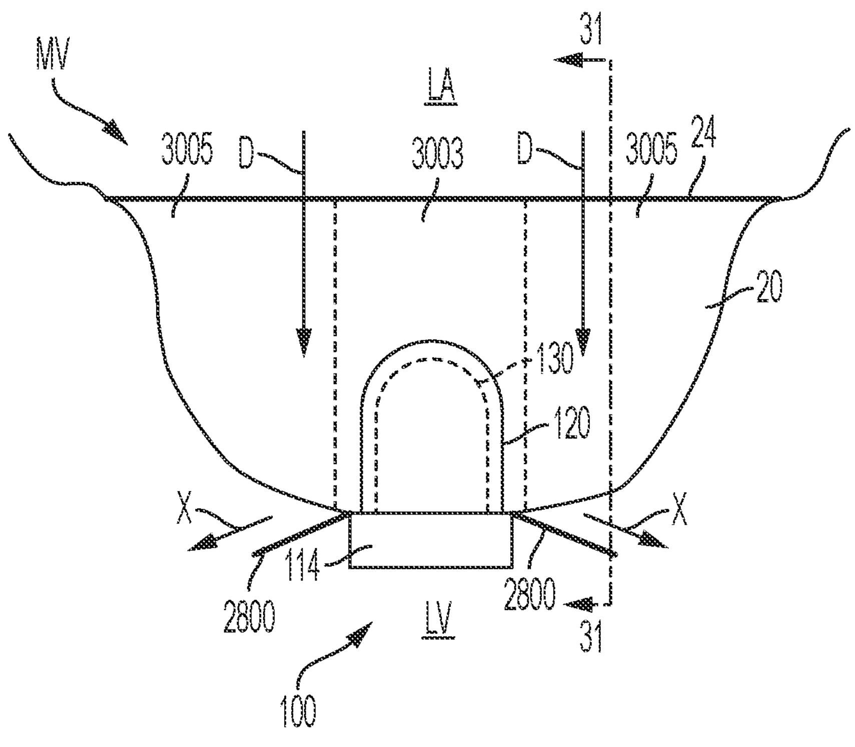
FIG. 30 shows the implantable prosthetic device implanted in the first position within the valve shown in FIG. 28, viewed when the heart is in a diastolic phase.
Figure 31:
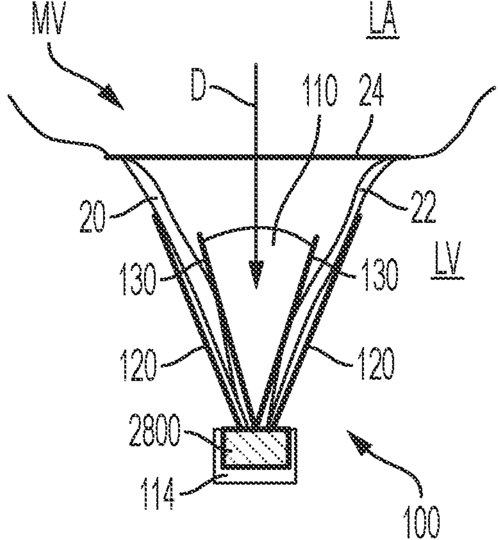
FIG. 31 is a cross-sectional view of the implantable prosthetic device implanted in the first position within the native valve shown in FIG. 30, with the section taken along the plane indicated by line 31-31 shown in FIG. 30.

Referring to FIGS. 30 and 31, during the diastolic phase, the leaflets 20, 22 of the mitral valve MV open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the deflecting paddles 2801 of the leak control extensions 2800. In some embodiments, the blood provides a force on the deflecting paddles 2801 that causes the deflecting paddles 2801 to pivot about the cap 114 or flex with respect to the cap 114 such that the blood moves around the leak control extensions 2800 in the direction X.

Referring to FIGS. 32-35, during the systolic phase, the leaflets 20, 22 of the mitral valve MV coapt to prevent blood from regurgitating into the left atrium LA as blood is pushed from the left ventricle and into the aorta, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 are positioned to prevent blood from regurgitating into the left atrium through the one or more openings 2400.

Figure 32:
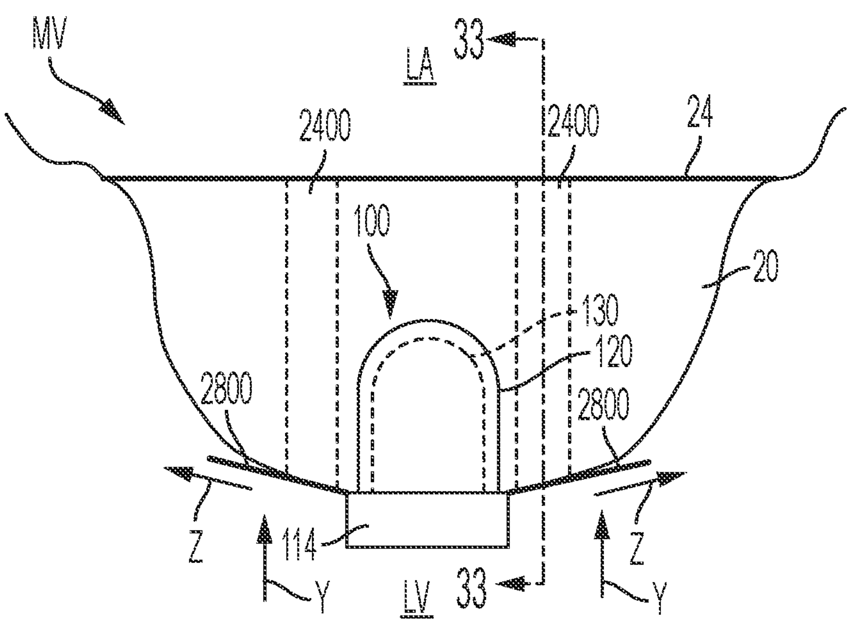
FIG. 32 shows the implantable prosthetic device implanted in the first position within the valve shown in FIG. 28, viewed when the heart is in a systolic phase.
Figure 33:
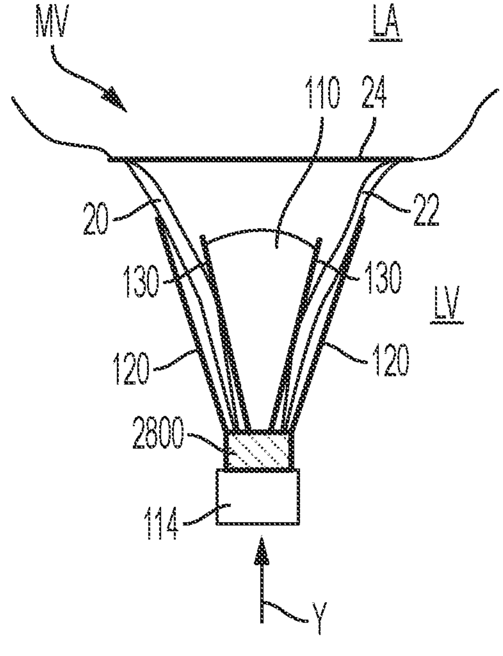
FIG. 33 is a cross-sectional view of the implantable prosthetic device implanted in the first position within the native valve shown in FIG. 32, with the section taken along the plane indicated by line 33-33 shown in FIG. 32.
Figures 34, 35:
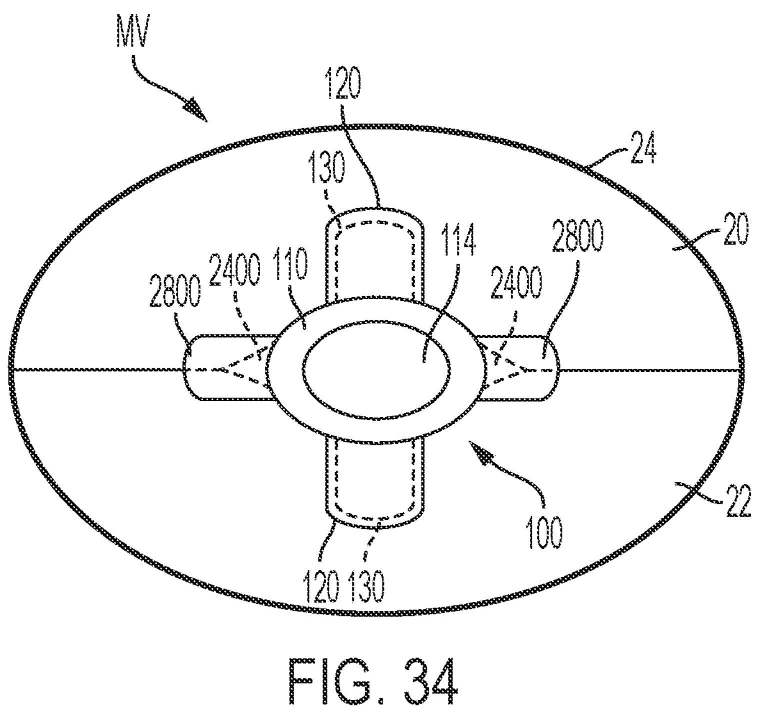
FIG. 34 shows the implantable prosthetic device implanted in the first position within the native valve shown in FIG. 28, viewed from a ventricle side of the native valve.
FIG. 35 shows the implantable prosthetic device implanted in the first position within the native valve shown in FIG. 28, viewed from an atrial side of the native valve.

Referring to FIGS. 32 and 33, contraction of the left ventricle LV pushes blood toward the mitral valve MV in the direction Y and engages the deflecting paddles 2801 of the leak control extensions 2800, which prevents blood from moving through the openings 2400 and into the left atrium LA. In some embodiments, the blood provides a force on the deflecting paddles 2801 that causes the deflecting paddles 2801 to pivot about the cap 114 or flex relative to the cap, such that the blood is directed away from the openings 2400 around the leak control extensions 2800 in the direction Z.

Figures 36, 37:
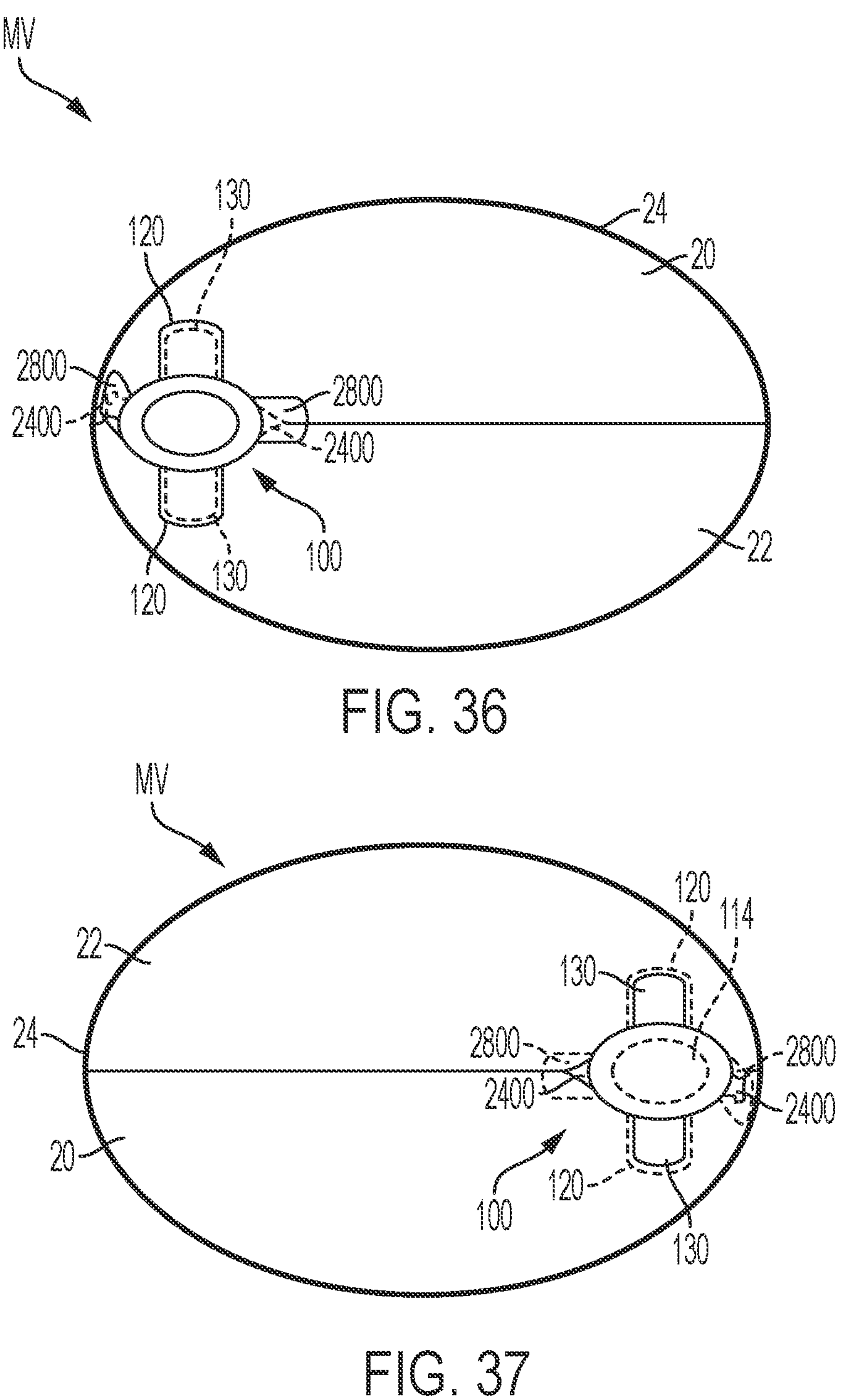
FIG. 36 shows the implantable prosthetic device of FIG. 28 implanted in a second example position within the native valve, viewed from the ventricle side of the native valve.
FIG. 37 shows the implantable prosthetic device of FIG. 28 implanted in the second example position within the native valve shown in FIG. 36, viewed from the atrial side of the native valve.
Figure 38A:
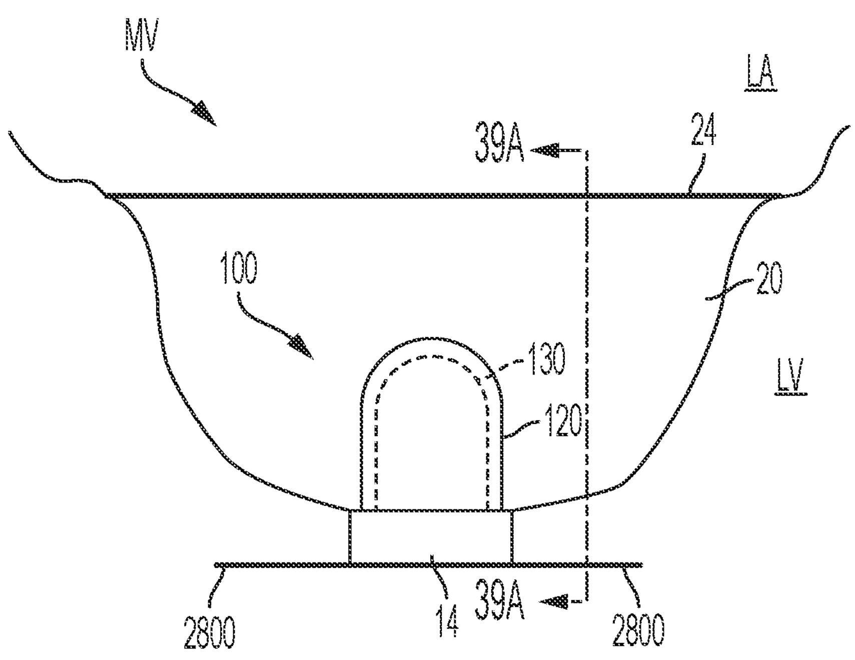
FIG. 38A shows an example of an implantable prosthetic device implanted in a first example position within the native valve.
Figure 38B:
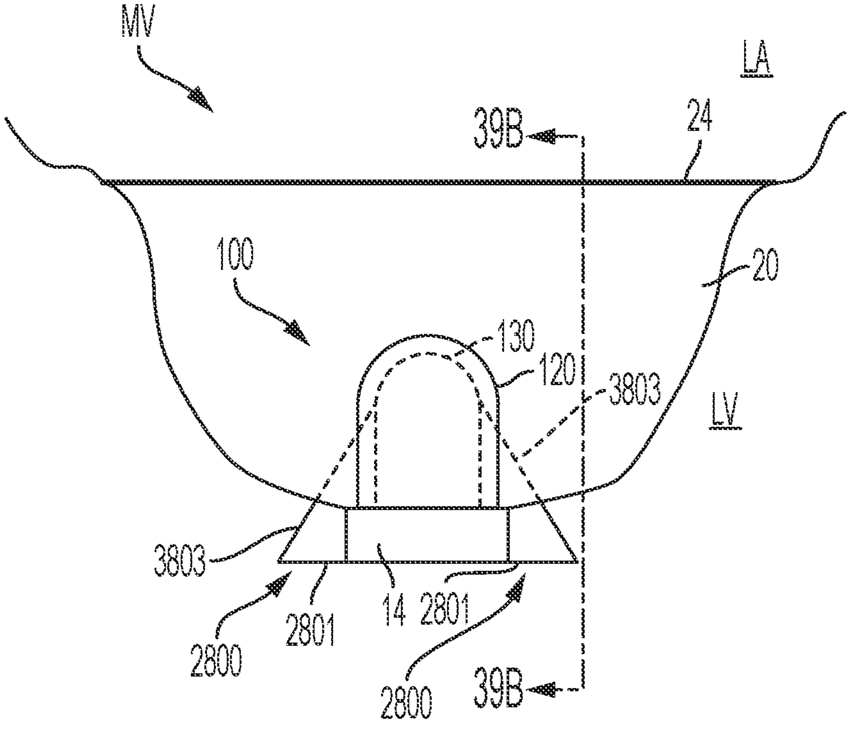
FIG. 38B shows an example of an implantable prosthetic device implanted in a first example position within the native valve.
Figure 39A:
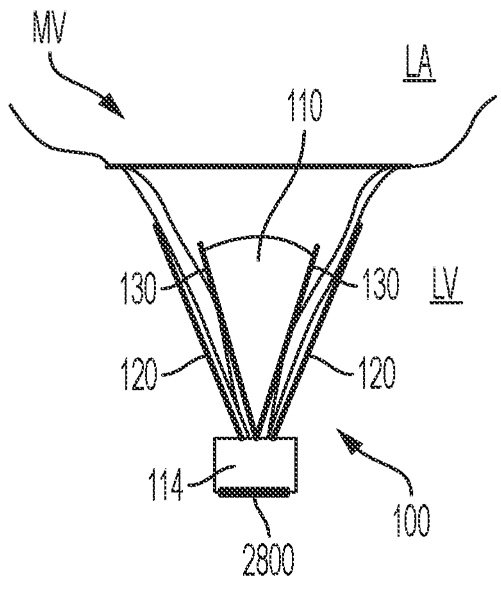
FIG. 39A is a cross-sectional view of the implantable prosthetic device implanted in the first position within the native valve shown in FIG. 38A, with the section taken along the plane indicated by line 39A-39A in FIG. 38A.
Figure 39B:
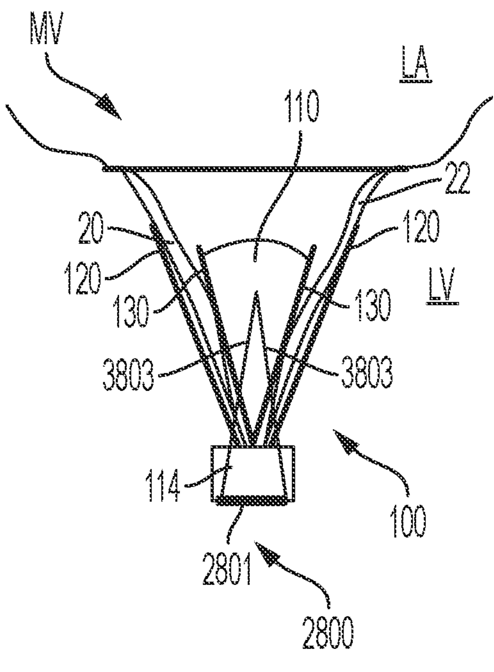
FIG. 39B is a cross-sectional view of the implantable prosthetic device implanted in the first position within the native valve shown in FIG. 38B, with the section taken along the plane indicated by line 39B-39B in FIG. 38B.

Referring to FIGS. 36 and 37, the device 100 shown in FIGS. 28-35 can be placed within the native valve in a location near the annulus 24. Similar to the device 100 being located in a more central location within the native valve (as shown in FIGS. 28-35), openings 2400 may form where both leaflets 20, 22 and the device 100 meet. As shown in the illustrated embodiment, when the device 100 is placed near the annulus 24, the force on the native valve by the device 100 may cause the opening 2400 adjacent to the annulus 24 to have a deformed shape. In some embodiments, the leak control extensions 2800 are flexible such that forces applied to the leak control extensions cause the leak control extensions to compress. For example, as shown in FIGS. 36 and 37, the leak control extension 2800 adjacent to the annulus 24 is pressed against the annulus 24 (or the side wall of the ventricle), which causes the leak control extension 2800 to compress into a deformed shape. This compression of the leak control extensions 2800 allows the leak control extensions to cover the deformed opening 2400 that is adjacent to the annulus 24. The flexible leak control extensions 2800 are advantageous because it allows the device 100 to be positioned within the native valve at various locations without causing irritation to the annulus 24 or the side walls of the ventricle or the atrium. In addition, the flexible leak control extensions 2800 are advantageous because they are capable of taking the form of any deformed openings caused by the connection between the device 100 and the leaflets 20, 22.

FIGS. 38A-47A show an example of an implantable prosthetic device 100 attached to leaflets 20, 22 of a native valve (illustrated, for example, as mitral valve MV, but could be similarly used on another valve such as the tricuspid valve) in the fully closed position, where the device 100 includes one or more leak control extensions 2800. In the embodiment shown in FIGS. 38A-45A, the implantable prosthetic device 100 is attached to the native valve at a substantially central location within the annulus 24. It should be understood, however, that the implantable prosthetic device 100 can be attached to the leaflets 20, 22 at any location within the native valve (e.g., the location shown in FIGS. 46A-47A). The device 100 has a pair of paddles 120, a pair of clasps 130, a coaption element 110 (e.g., a spacer etc.), a cap 114, and at least one leak control extension 2800. However, the implantable prosthetic device 100 can take any suitable form, such as, for example, any formed described in the present application in combination with at least one leak control extension 2800.

The leak control extension(s) 2800 are configured to prevent blood from regurgitating from the ventricle and into the atrium during the systolic phase. That is, the leak control extension(s) 2800 extend from the device (e.g., from the end of the cap 114 of the device 100) such that the leak control extensions are positioned to prevent blood from moving through any jets or openings between the leaflets 20, 22 of the mitral valve MV during the systolic phase. In the illustrated embodiment, the leak control extensions 2800 include deflecting paddles 2801 that are positioned in the left ventricle LV when the device 100 is attached to the leaflets 20, 22. In the illustrated embodiment, the device 100 has two leak control extensions 2800 that are attached to a bottom surface of the cap 114. The leak control extensions 2800 can be connected to each other (as shown in the illustrated embodiment), or the leak control extensions 2800 can be separate extensions. While the illustrated embodiment is shown as having two leak control extensions 2800, it should be understood that the device 100 can have any suitable number of leak control extensions.

Figure 40A:
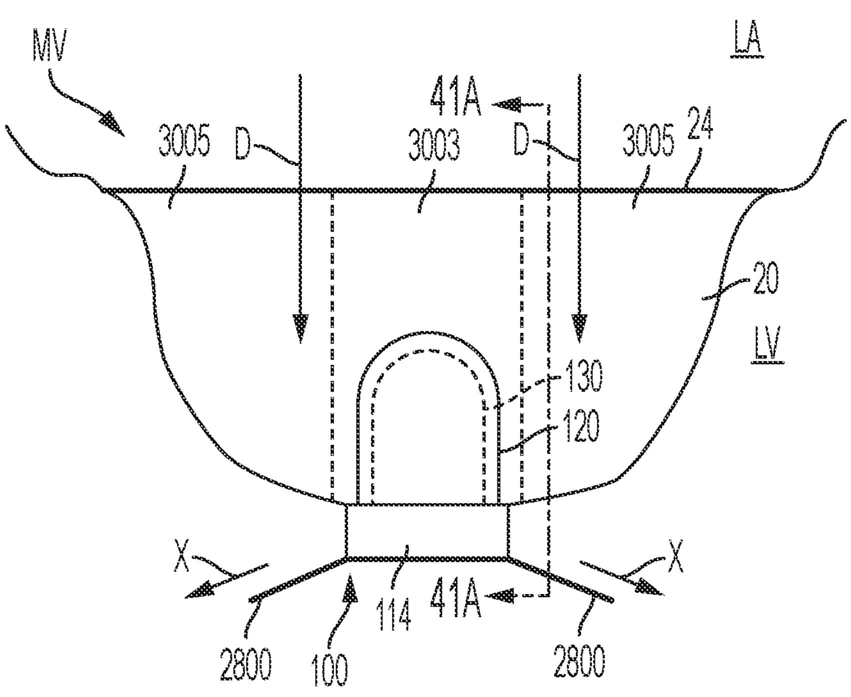
FIG. 40A shows the implantable prosthetic device implanted in the first position within the native valve shown in FIG. 38A, viewed when the heart is in a diastolic phase.
Figure 41A:
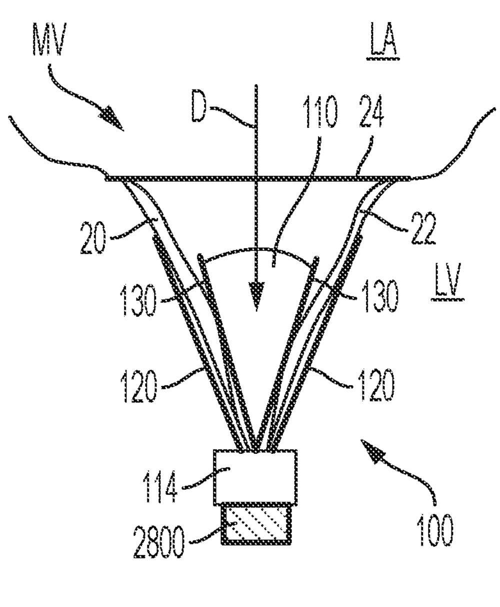
FIG. 41A is a cross-sectional view of the implantable prosthetic device implanted in the first position within the native valve shown in FIG. 40A, with the section taken along the plane indicated by line 41A-41A shown in FIG. 40A.

Referring to FIGS. 40A and 41A, during the diastolic phase, the leaflets 20, 22 of the mitral valve MV open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the leak control extensions 2800. In some embodiments, the blood provides a force on the leak control extensions 2800 that causes the leak control extensions 2800 to pivot about the cap 114 or flex relative to the cap such that the blood moves around the leak control extensions 2800 in the direction X.

Referring to FIGS. 42A-45A, during the systolic phase, the leaflets 20, 22 of the mitral valve MV coapt to prevent blood from regurgitating into the left atrium LA as blood is pushed from the left ventricle and into the pulmonary artery PA, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 can be positioned to prevent blood from regurgitating into the left atrium through the one or more openings 2400.

Figure 42A:
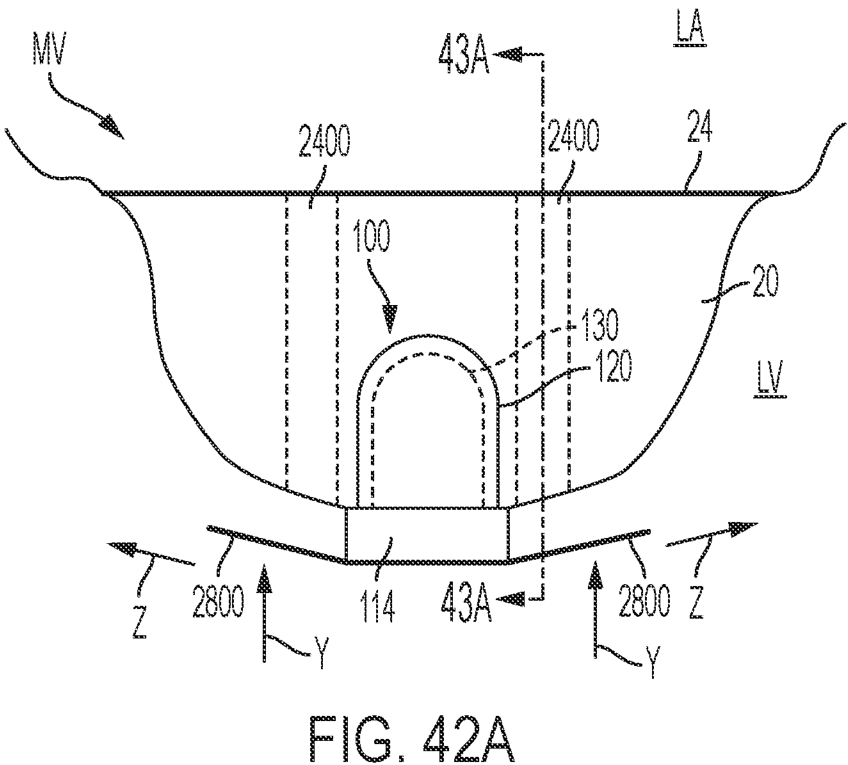
FIG. 42A shows the implantable prosthetic device implanted in the first position within the native valve shown in FIG. 38A, viewed when the heart is in a systolic phase.
Figures 43A, 43B:
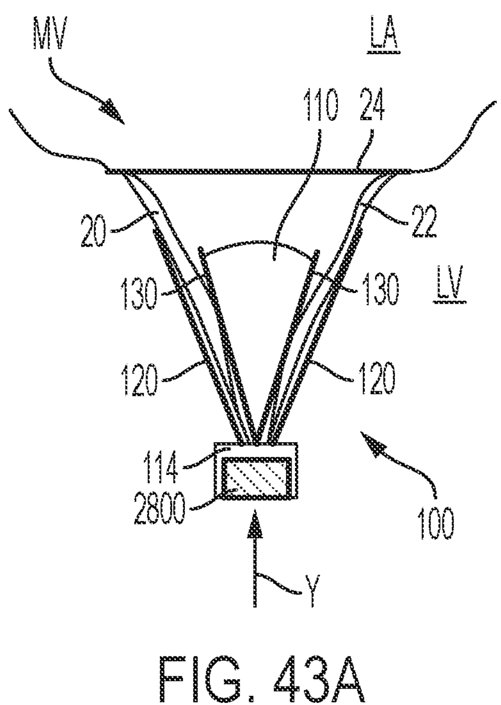
FIG. 43A is a cross-sectional view of the implantable prosthetic device implanted in the first position within the native valve shown in FIG. 42A, with the section taken along the plane indicated by line 43A-43A shown in FIG. 42A.
FIG. 43B is a cross-sectional view of the implantable prosthetic device implanted in the first position within the native valve shown in FIG. 42B, with the section taken along the plane indicated by line 43B-43B shown in FIG. 42B.
Figures 44A, 44B:
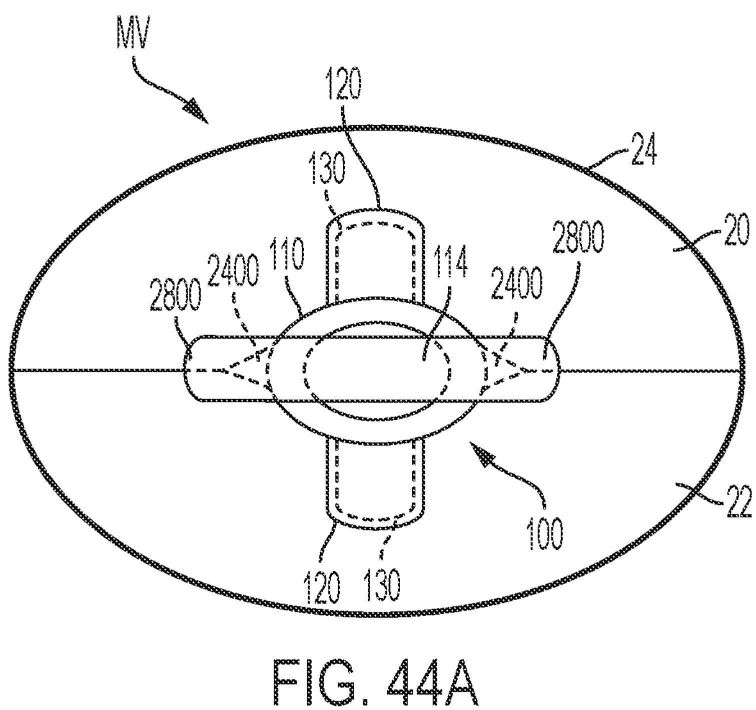
FIG. 44A shows the implantable prosthetic device implanted in the first position within the native valve shown in FIG. 38A, viewed from a ventricle side of the native valve.
FIG. 44B shows the implantable prosthetic device implanted in the first position within the native valve shown in FIG. 38B, viewed from a ventricle side of the native valve.
Figure 45A:
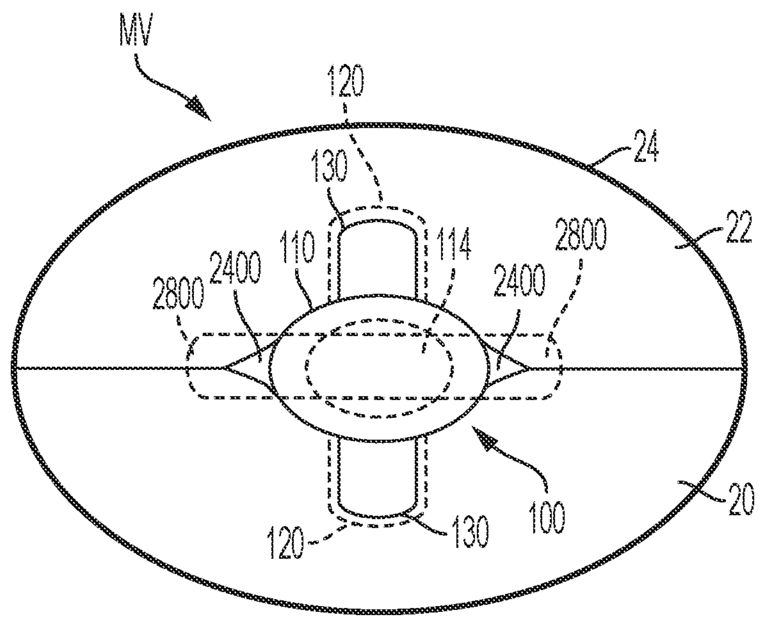
FIG. 45A shows the implantable prosthetic device implanted in the first position within the native valve shown in FIG. 38A, viewed from an atrial side of the native valve.
Figure 45B:
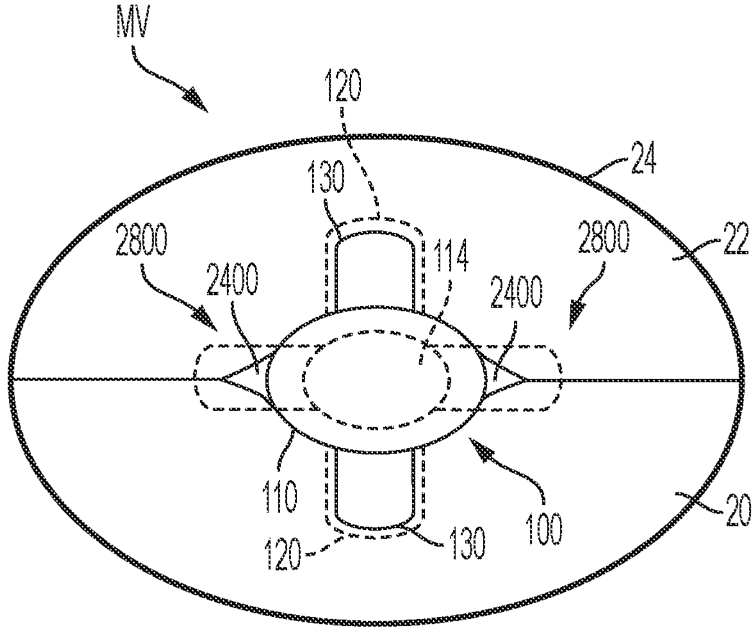
FIG. 45B shows the implantable prosthetic device implanted in the first position within the native valve shown in FIG. 38B, viewed from an atrial side of the native valve.

Referring to FIGS. 42A and 43A, contraction of the left ventricle LV pushes blood toward the mitral valve MV in the direction Y and engages the deflecting paddles 2801 of the leak control extensions 2800, which prevents blood from moving through the openings 2400 and into the left atrium LA. In some embodiments, the blood provides a force on the deflecting paddles 2801 that causes the deflecting paddles 2801 to pivot about the cap 114 or flex relative to the cap such that the blood moves around the leak control extensions 2800 in the direction Z.

Figure 46A:
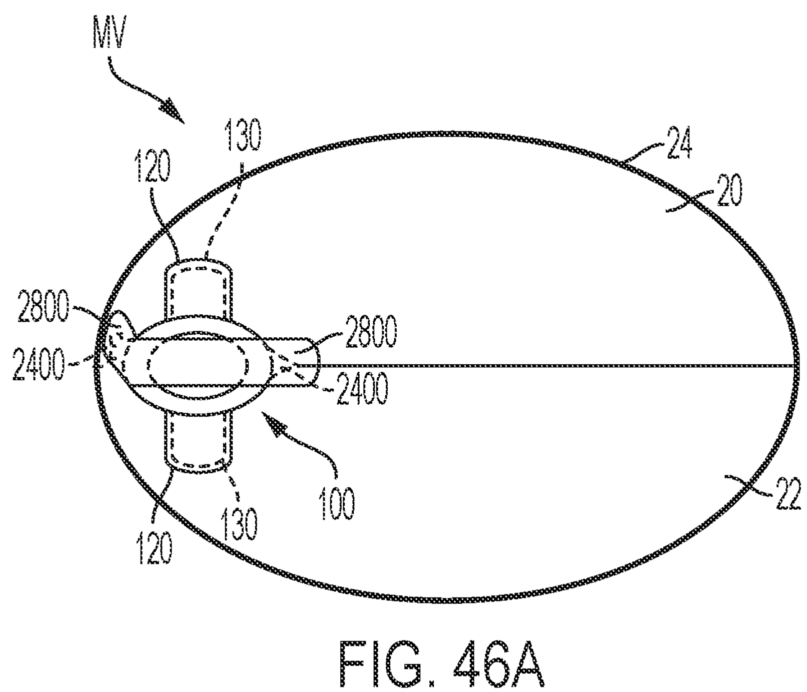
FIG. 46A shows the implantable prosthetic device of FIG. 38A implanted in a second example position within the native valve, viewed from the ventricle side of the native valve.
Figures 47A, 47B:
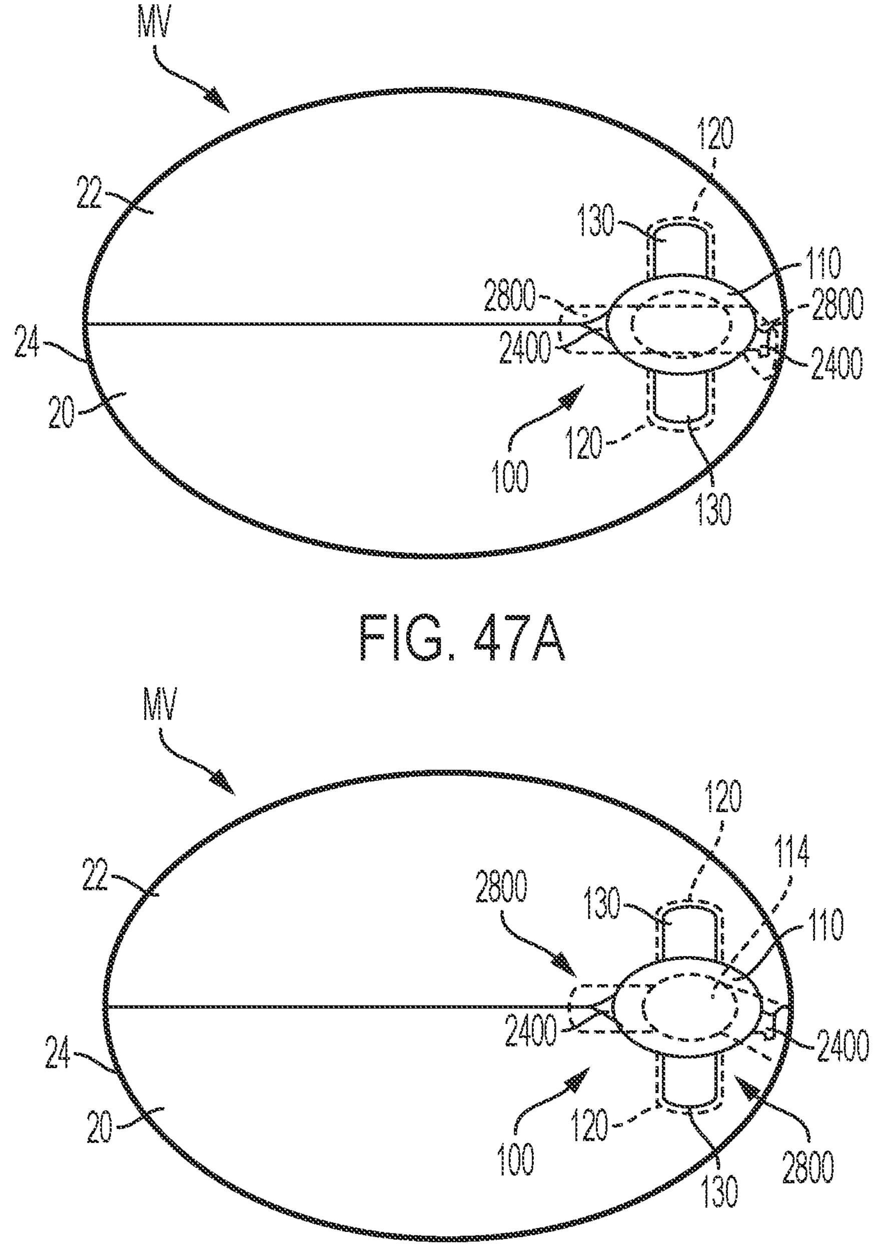
FIG. 47A shows the implantable prosthetic device of FIG. 38A implanted in the second example position within the mitral valve shown in FIG. 46A, viewed from the atrial side of the native valve.
FIG. 47B shows the implantable prosthetic device of FIG. 38B implanted in the second example position within the mitral valve shown in FIG. 46B, viewed from the atrial side of the native valve.
Figure 48A:
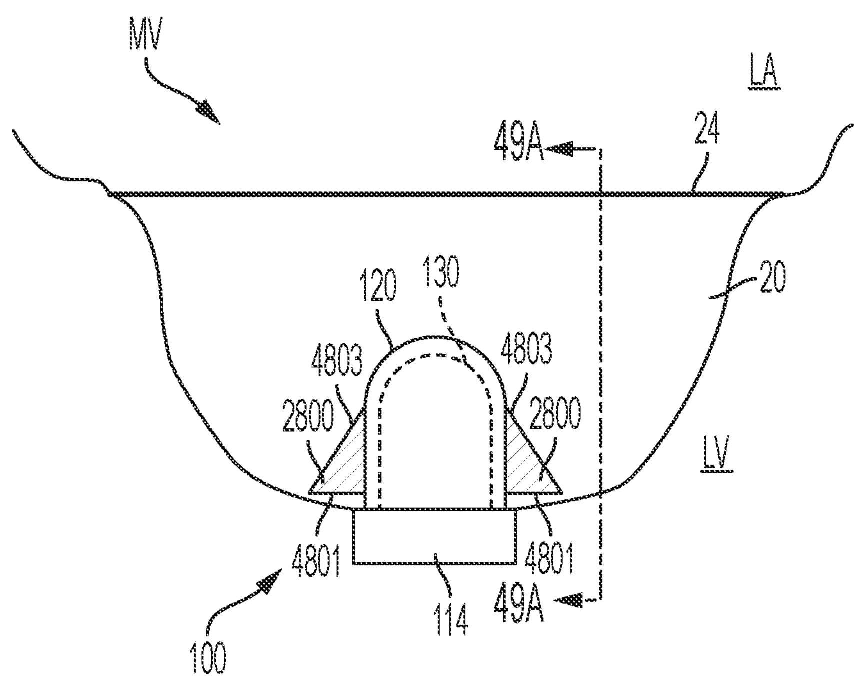
FIG. 48A shows an example of an implantable prosthetic device implanted in a first example position within the native valve.
Figure 48B:
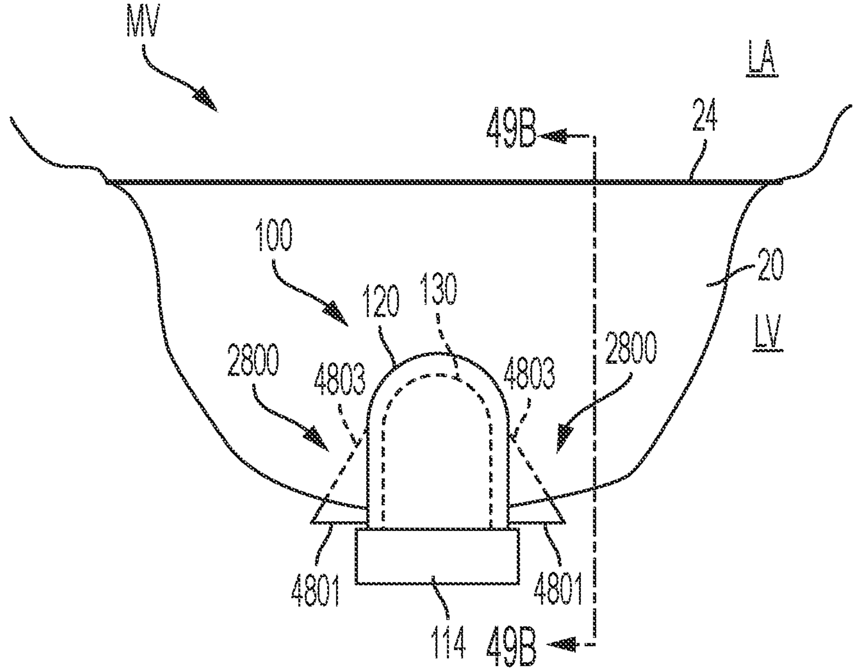
FIG. 48B shows an example of an implantable prosthetic device implanted in a first example position within the native valve.
Figure 49A:
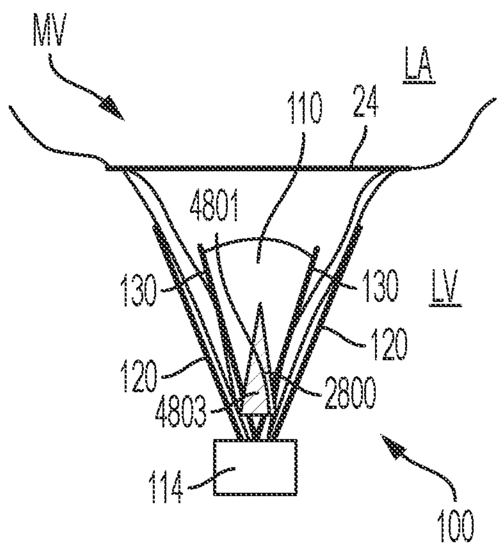
FIG. 49A is a cross-sectional view of the implantable prosthetic device implanted in the first position within the native valve shown in FIG. 48A, with the section taken along the plane indicated by line 49A-49A in FIG. 48A.
Figure 49B:
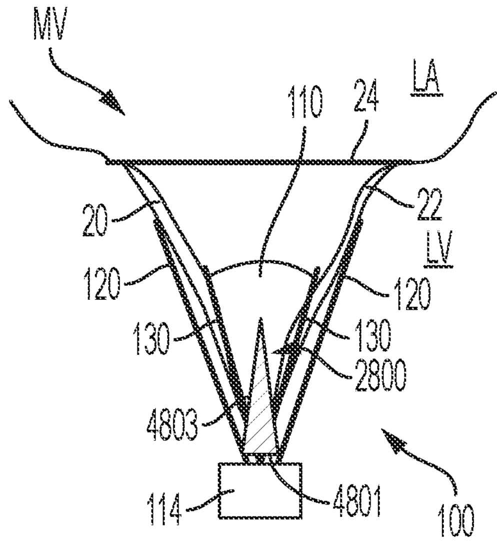
FIG. 49B is a cross-sectional view of the implantable prosthetic device implanted in the first position within the native valve shown in FIG. 48B, with the section taken along the plane indicated by line 49B-49B in FIG. 48B.

Referring to FIGS. 46A and 47A, the device 100 shown in FIGS. 38A-45A can be placed within the mitral valve MV in a location near the annulus 24. Similar to the device 100 being located in a more central location within the mitral valve MV (as shown in FIGS. 38A-45A), openings 2400 may form where both leaflets 20, 22 and the device 100 meet. As shown in the illustrated embodiment, when the device 100 is placed near the annulus 24, the force on the mitral valve MV by the device 100 may cause the opening 2400 adjacent to the annulus 24 to have a deformed shape. In some embodiments, the leak control extensions 2800 are flexible such that forces applied to the leak control extensions cause the leak control extensions to compress. For example, as shown in FIGS. 46A and 47A, the leak control extension 2800 adjacent to the annulus 24 is pressed against the annulus 24 (or the side wall of the left ventricle LV), which causes the leak control extension 2800 to compress into a deformed shape. This compression of the leak control extensions 2800 allows the leak control extensions to cover the deformed opening 2400 that is adjacent to the annulus 24. The flexible leak control extensions 2800 are advantageous because they allow the device 100 to be positioned within the mitral valve MV at various positions. In addition, the flexible leak control extensions 2800 are advantageous because they are capable of taking a form needed to block blood-flow through any deformed openings caused by the connection between the device 100 and the leaflets 20, 22.

Figure 78:
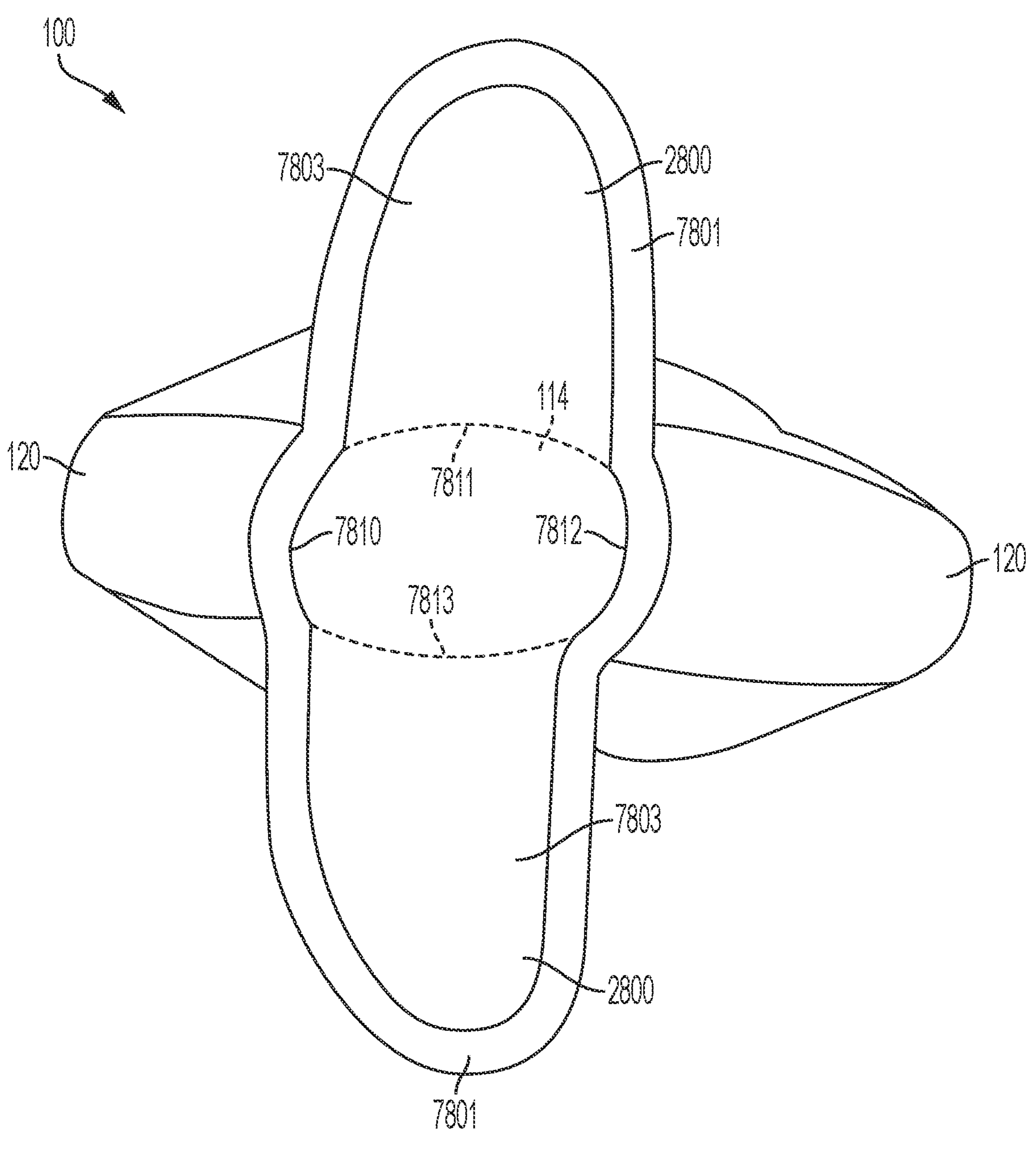
FIG. 78 is a bottom view of a more specific example of the implantable prosthetic device shown in FIGS. 38A-47A.

FIG. 78 illustrates a more specific example of the implantable prosthetic device 100 shown in FIGS. 38A-47A. The device 100 includes a pair of paddles 120, a pair of clasps (not shown), a coaption element (e.g., a spacer, etc.), a cap 114, and a pair of leak control extensions 2800. The leak control extensions 2800 have deflecting paddles 2801 that include a flexible frame 7801 and a barrier material 7803. The flexible frame 7801 can be made of, for example, a metal wire, such as a steel or nitinol wire, plastic, etc. The barrier material 7803 can take a wide variety of different forms. For example, the barrier material can be a cloth material, a biocompatible material, bovine or porcine heart tissue, a plastic membrane, etc. In the illustrated embodiment, the flexible frame 7801 of each leak control extension 2800 is attached to the front and rear edges 7810, 7812 of the cap 114, and the barrier material 7803 is optionally attached to the side edges 7811, 7813 of the cap 114. This connection between the leak control extensions 2800 and the cap 114 allows for the leak control extensions 2800 to pivot or flex about the side edges 7811, 7813 of the cap.

Figure 79:
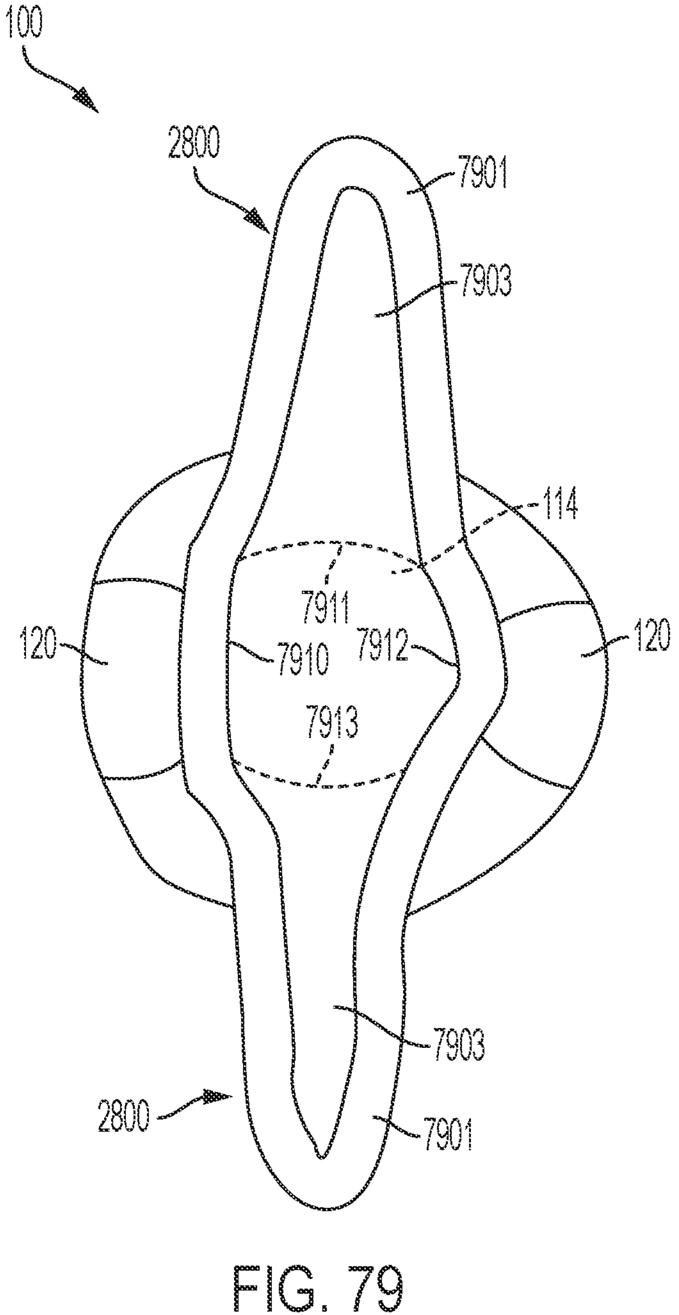
FIG. 79 is a bottom view of a more specific example of the implantable prosthetic device shown in FIGS. 38A-47A.

FIG. 79 illustrates a more specific example of the implantable prosthetic device 100 shown in FIGS. 38A-47A where the leak control extensions 2800 have a different shape than the FIG. 78 example. For example, the leak control extensions have a narrower shape. Though various example shapes are shown a variety of different shapes are possible, e.g., triangular, circular, rectangular, ovoid, oval, etc. In one example implementation, the shape of the leak control extensions 2800 can be modified by bending before the device 100 is implanted. The device 100 includes a pair of paddles 120, a pair of clasps (not shown), a coaption element (e.g., a spacer, etc.), a cap 114, and a pair of leak control extensions 2800. The leak control extensions 2800 have deflecting paddles 2801 that include a flexible frame 7901 and a barrier material 7903. The flexible frame 7901 can be made of, for example, a metal wire, such as a steel or nitinol wire, plastic, etc. In one example implementation, the flexible frame is made from a plastically deformable material to allow the shape of the flexible frame 7901 to be modified before implantation. The barrier material 7903 can take a wide variety of different forms. For example, the barrier material can be a cloth material, a biocompatible material, bovine or porcine heart tissue, a plastic membrane, etc. In the illustrated embodiment, the flexible frame 7901 of each leak control extension 2800 is attached to the front and rear edges 7910, 7912 of the cap 114, and the barrier material 7803 is optionally attached to the side edges 7911, 7913 of the cap 114. This connection between the leak control extensions 2800 and the cap 114 allows for the leak control extensions 2800 to pivot or flex about the side edges 7911, 7913 of the cap.

FIGS. 38B-47B show an example of an implantable prosthetic device 100 attached to leaflets 20, 22 of a native valve (illustrated, for example, as a mitral valve MV, but could be similarly used on another valve such as the tricuspid valve) in the fully closed position, where the device 100 includes one or more leak control extensions 2800. In the embodiment shown in FIGS. 38B-45B, the implantable prosthetic device 100 is attached to the native valve at a substantially central location within the annulus 24. It should be understood, however, that the implantable prosthetic device 100 can be attached to the leaflets 20, 22 at any location within the native valve (e.g., the location shown in FIGS. 46B-47B).

In some implementations, the device 100 has a pair of paddles 120, a pair of clasps 130, a coaption element 110 (e.g., a spacer etc.), a cap 114, and at least one leak control extension 2800. However, the implantable prosthetic device 100 can take any suitable form, such as, for example, any formed described in the present application in combination with at least one leak control extension 2800.

In some implementations, the leak control extension(s) 2800 are configured to prevent or inhibit blood from regurgitating from the ventricle and into the atrium during the systolic phase. That is, the leak control extension(s) 2800 extend from the device (e.g., from the end of the cap 114 of the device 100) such that the leak control extensions are positioned to prevent blood from moving through any jets or openings between the leaflets 20, 22 of the native valve during the systolic phase. In the illustrated embodiment, the leak control extensions 2800 include deflecting paddles 2801 that are positioned in the ventricle when the device 100 is attached to the leaflets 20, 22, where the deflecting paddles 2801 are attached to the spacer 110 by one or more arms 3803.

In some implementations, the arms 3803 secure the deflecting paddles 2801 to the spacer 110 to prevent the deflecting paddles 2801 from moving to a position that does not allow the deflecting paddles 2801 to prevent regurgitation of blood during the systolic phase. The arms 3803 can be made of, for example, a cloth material, a suture, a wire, any combination thereof, or any other suitable material or component that is capable of securing the deflecting paddles to the spacer 110. While the illustrated embodiment shows the arms 3803 connecting the deflecting paddles 2801 to the spacer 110, it should be understood that the arms 3803 can connect the deflecting paddles 2801 to any other portion of the device 100 that prevents unwanted movement of the deflecting paddles.

In the illustrated example, the device 100 has two leak control extensions 2800, where each leak control extension 2800 includes a deflecting paddle 2801 that is attached to a bottom surface of the cap 14. The deflecting paddles 2801 can be connected to each other (as shown in the illustrated embodiment), or the deflecting paddles 2801 can be separate extensions. While the illustrated embodiment is shown as having two leak control extensions 2800, it should be understood that the device 100 can have any suitable number of leak control extensions.

Figure 40B:
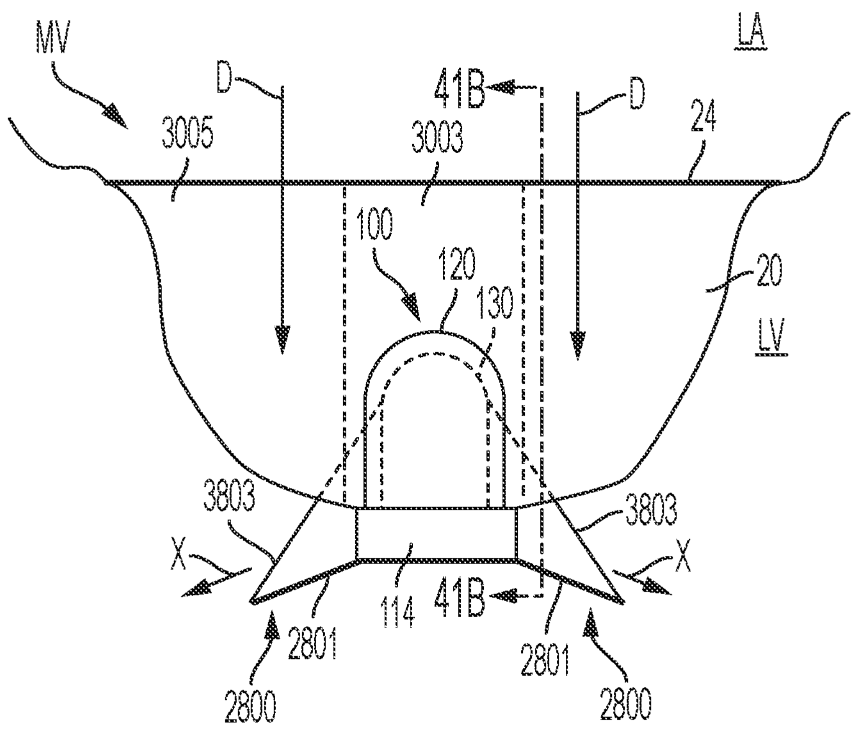
FIG. 40B shows the implantable prosthetic device implanted in the first position within the native valve shown in FIG. 38B, viewed when the heart is in a diastolic phase.
Figure 41B:
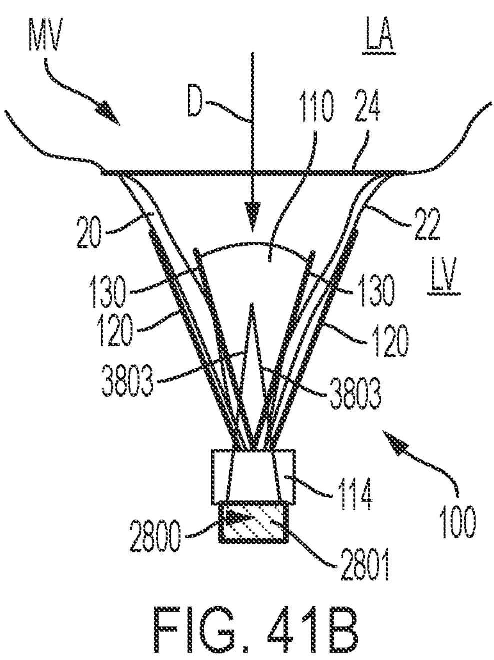
FIG. 41B is a cross-sectional view of the implantable prosthetic device implanted in the first position within the native valve shown in FIG. 40B, with the section taken along the plane indicated by line 41B-41B shown in FIG. 40B.

Referring to the example shown in FIGS. 40B and 41B, during the diastolic phase, the leaflets 20, 22 of the mitral valve MV open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the leak control extensions 2800. In some implementations, the blood provides a force on the leak control extensions 2800 that causes the deflecting paddles 2801 to pivot about the cap 114 or flex relative to the cap such that the blood moves around the leak control extensions 2800 in the direction X.

Referring to FIGS. 42B-45B, during the systolic phase, the leaflets 20, 22 of the mitral valve MV coapt to prevent blood from regurgitating into the left atrium LA as blood is pushed from the left ventricle and into the pulmonary artery PA, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 can be positioned to prevent blood from regurgitating into the left atrium through the one or more openings 2400.

Figure 42B:
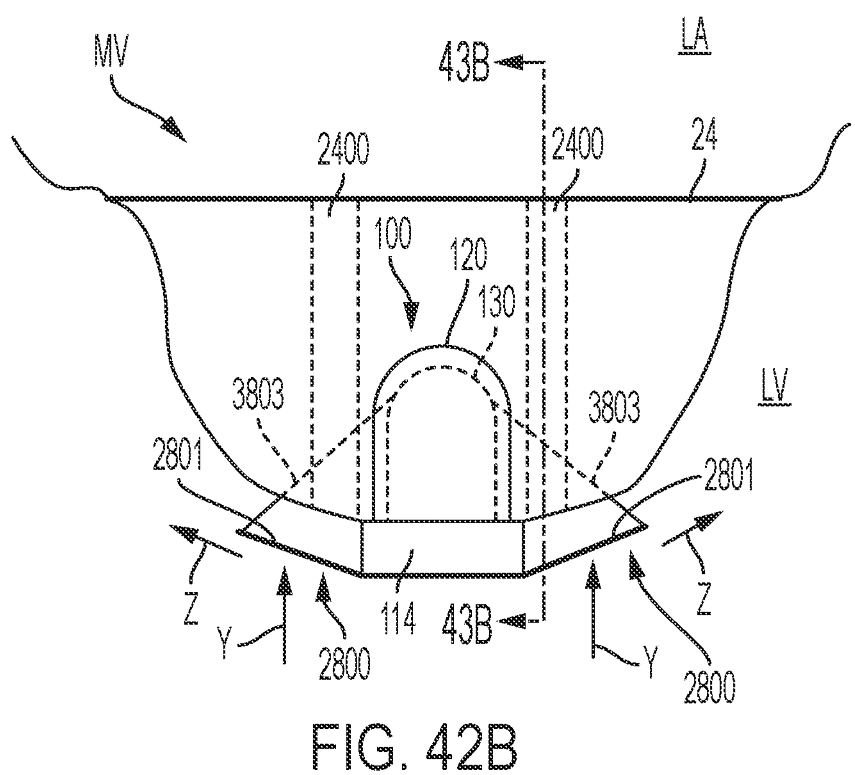
FIG. 42B shows the implantable prosthetic device implanted in the first position within the native valve shown in FIG. 38B, viewed when the heart is in a systolic phase.

Referring to FIGS. 42B and 43B, contraction of the left ventricle LV pushes blood toward the mitral valve MV in the direction Y and engages the deflecting paddles 2801 of the leak control extensions 2800, which prevents blood from moving through the openings 2400 and into the left atrium LA. In some implementations, the blood provides a force on the deflecting paddles 2801 that causes the deflecting paddles 2801 to pivot about the cap 114 or flex relative to the cap such that the blood moves around the leak control extensions 2800 in the direction Z.

Figure 46B:
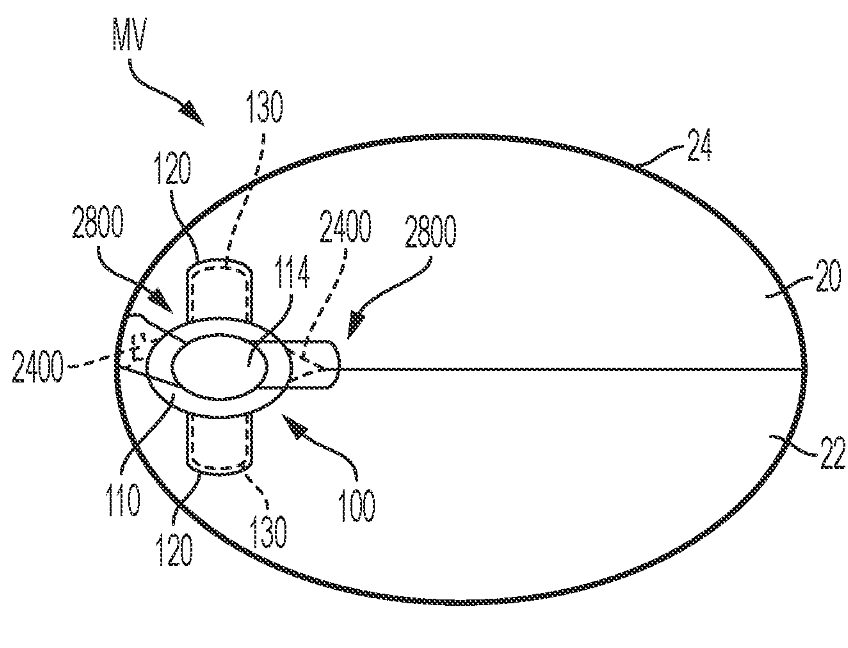
FIG. 46B shows the implantable prosthetic device of FIG. 38B implanted in a second example position within the native valve, viewed from the ventricle side of the native valve.

Referring to FIGS. 46B and 47B, the device 100 shown in FIGS. 38B-45B can be placed within the native valve in a location near the annulus 24. Similar to the device 100 being located in a more central location within the native valve (as shown in FIGS. 38B-45B), openings 2400 may form where both leaflets 20, 22 and the device 100 meet. As shown in the illustrated embodiment, when the device 100 is placed near the annulus 24, the force on the native valve by the device 100 may cause the opening 2400 adjacent to the annulus 24 to have a deformed shape. In some implementations, the leak control extensions 2800 are flexible such that forces applied to the leak control extensions cause the leak control extensions to compress. For example, as shown in FIGS. 46B and 47B, the leak control extension 2800 adjacent to the annulus 24 is pressed against the annulus 24 (or the side wall of the ventricle), which causes the leak control extension 2800 to compress into a deformed shape. This compression of the leak control extensions 2800 allows the leak control extensions to cover the deformed opening 2400 that is adjacent to the annulus 24. The flexible leak control extensions 2800 are advantageous because they allow the device 100 to be positioned within the native valve at various positions. In addition, the flexible leak control extensions 2800 are advantageous because they are capable of taking a form needed to block blood-flow through any deformed openings caused by the connection between the device 100 and the leaflets 20, 22.

FIGS. 48A-57A show an example of an implantable prosthetic device 100 attached to the leaflets 20, 22 of a native valve (illustrated, for example, as mitral valve MV, but could be similarly used on another valve such as the tricuspid valve) in the fully closed position, where the device 100 includes one or more leak control extensions 2800. In the embodiment shown in FIGS. 48A-55A, the implantable prosthetic device 100 is attached to the native valve at a substantially central location, with the leak control extensions 2800 between the bottom of the native valve leaflets and the native valve annulus. It should be understood, however, that the implantable prosthetic device 100 can be attached to the leaflets 20, 22 at any location (e.g., the location shown in FIGS. 56A-57A). The device 100 has a pair of paddles 120, a pair of clasps 130, a coaption element 110 (e.g., a spacer, etc.), a cap 114, and at least one leak control extension 2800. However, the implantable prosthetic device 100 can take any suitable form, such as, for example, any formed described in the present application in combination with at least one leak control extension 2800.

The leak control extension(s) 2800 are configured to prevent blood from regurgitating from the ventricle and into the atrium during the systolic phase. That is, the leak control extension(s) 2800 extend from the device such that the leak control extensions are positioned to block blood moving through openings between the leaflets 20, 22 of the native valve during the systolic phase. In the illustrated embodiment, the leak control extensions 2800 include pockets that are configured for receiving blood to prevent the blood from moving into the atrium. In some embodiments, the leak control extensions 2800 can have a flexible frame or loop 4801 that defines an opening of the pocket and a barrier material 4803 that defines the interior of the pocket. The flexible frame 4801 can have any suitable shape for defining the opening of the pocket, such as, for example, a circular shape (as shown in FIGS. 54A-57A), an oval shape, a triangular shape, a polygonal shape, etc. The flexible frame 4801 can be made of, for example, a metal wire, such as a steel or nitinol wire, plastic, etc. The barrier material 4803 is configured to capture the blood such that the blood does not move through the leak control extension 2800. The barrier material 4803 can be made of, for example, a cloth material, a biocompatible material, bovine or porcine heart tissue, a plastic membrane, etc.

Figure 55A:
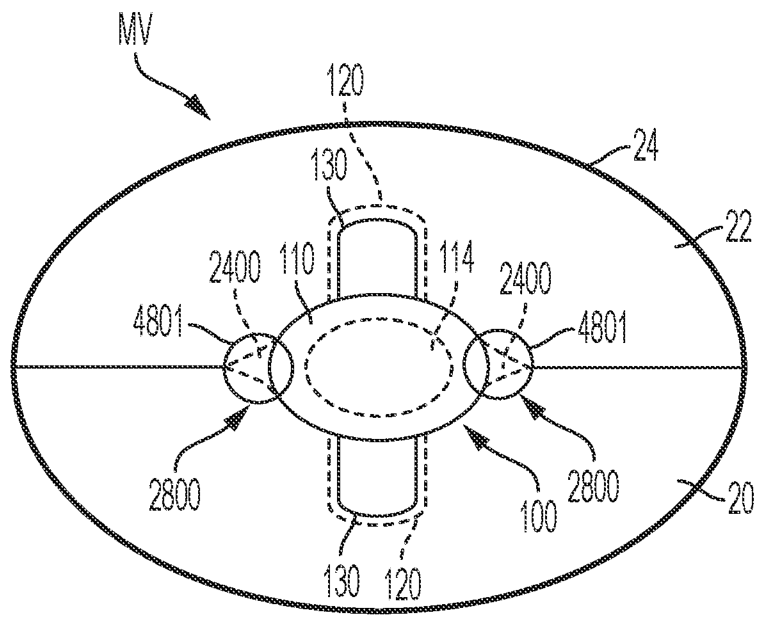
FIG. 55A shows the implantable prosthetic device implanted in the first position within the native valve shown in FIG. 48A, viewed from an atrial side of the native valve.

In the illustrated embodiment, the device 100 has two leak control extensions 2800 that are attached to the coaption element or spacer 110 (See FIG. 55A). In some embodiments, the opening of the leak control extensions 2800 are positioned in the atrium when the device 100 is attached to the leaflets 20, 22. The leak control extensions 2800 can, however, be attached to any other portion of the device 100 that allows the leak control extensions 2800 to be positioned to prevent blood from regurgitating into the atrium, and the opening of the leak control extensions 2800 can be in either the atrium or the ventricle. For example, the leak control extensions 2800 can be attached to the pair of paddles 120, the pair of clasps 130, the coaption element 110, the cap 114, or any combination thereof. While the illustrated embodiment is shown as having two leak control extensions 2800, it should be understood that the device 100 can have any suitable number of leak control extensions.

Figure 50A:
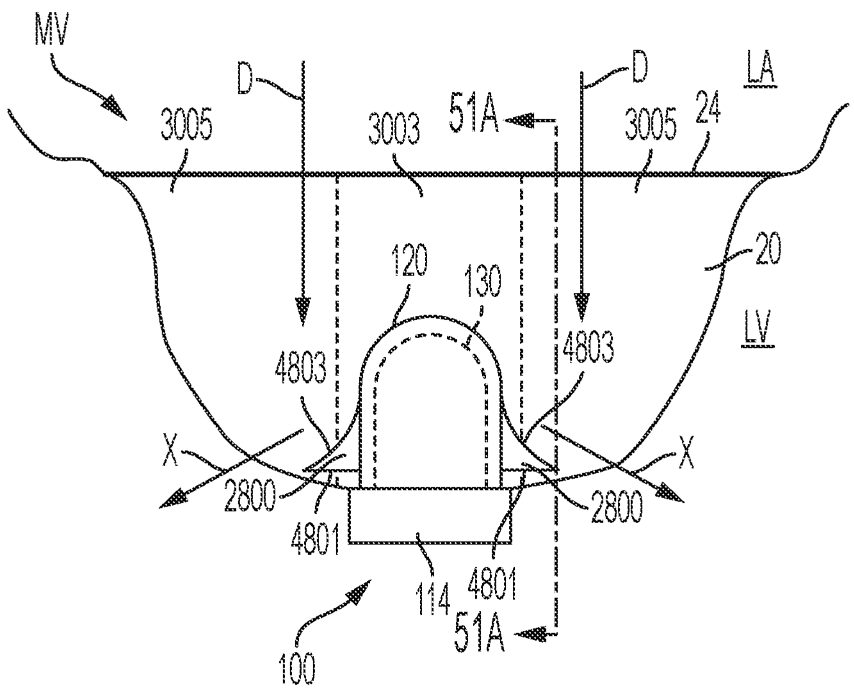
FIG. 50A shows the implantable prosthetic device implanted in the first position within the native valve shown in FIG. 48A, viewed when the heart is in a diastolic phase.
Figure 51A:
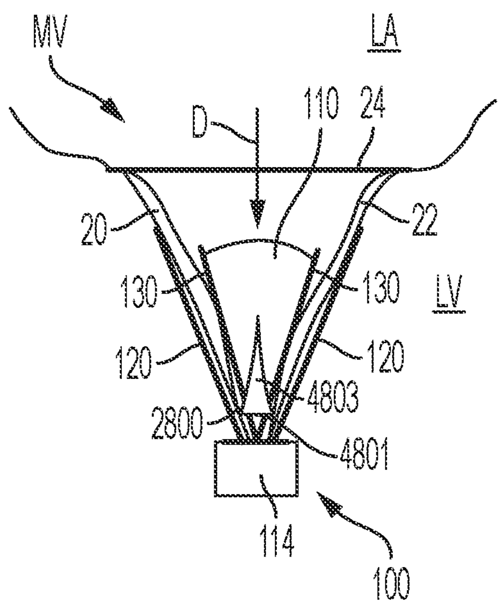
FIG. 51A is a cross-sectional view of the implantable prosthetic device implanted in the first position within the native valve shown in FIG. 50A, with the section taken along the plane indicated by line 51A-51A shown in FIG. 50A.

Referring to FIGS. 50A and 51A, during the diastolic phase, the leaflets 20, 22 of the mitral valve MV open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the leak control extensions 2800. In some embodiments, the blood provides a force on the barrier material 4803 of the leak control extensions 2800 that causes the barrier material 4803 to be compressed, and causes the blood to move around the leak control extensions 2800 in the direction X.

Referring to FIGS. 52A-55A, during the systolic phase, the leaflets 20, 22 of the mitral valve MV coapt to prevent blood from regurgitating into the left atrium LA as blood is pushed from the left ventricle and into the aorta, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 are positioned to prevent blood from regurgitating into the left atrium through the one or more openings 2400.

Figure 52A:
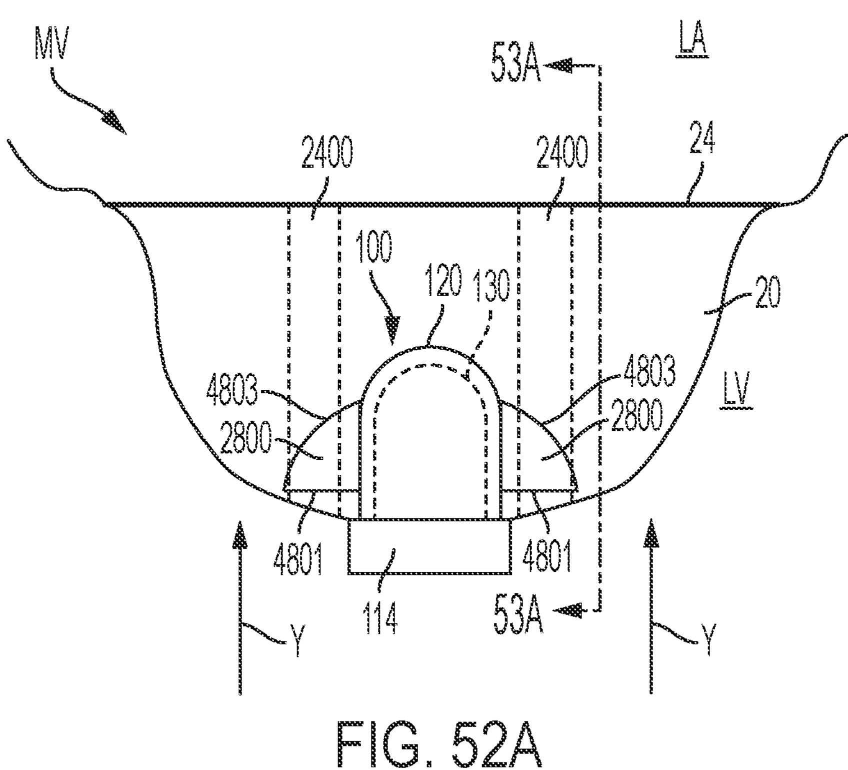
FIG. 52A shows the implantable prosthetic device implanted in the first position within the native valve shown in FIG. 48A, viewed when the heart is in a systolic phase.
Figure 53A:
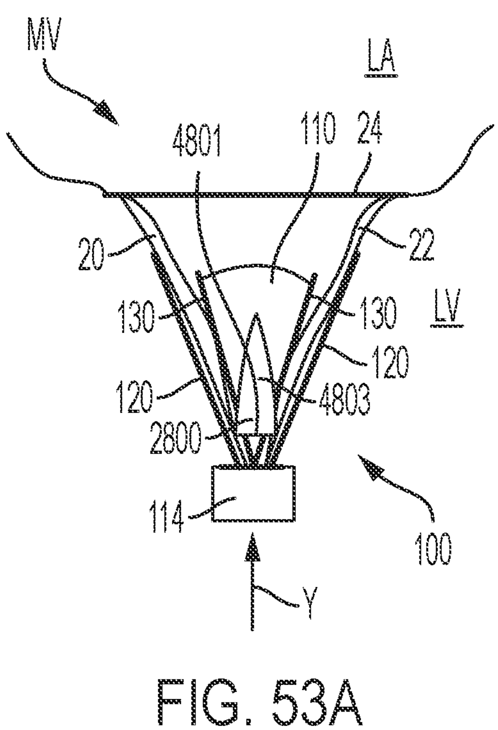
FIG. 53A is a cross-sectional view of the implantable prosthetic device implanted in the first position within the native valve shown in FIG. 52A, with the section taken along the plane indicated by line 53A-53A shown in FIG. 52A.

Referring to FIGS. 52A and 53A, contraction of the left ventricle LV pushes blood toward the mitral valve MV in the direction Y and engages the leak control extensions 2800 in the mitral valve, which prevents additional blood from moving through the openings 2400 and into the left atrium LA. In some embodiments, such as the illustrated embodiment, the blood enters the leak control extensions 2800 and provides a force on the barrier material 4803 that causes the barrier material 4803 to expand.

Figure 55B:
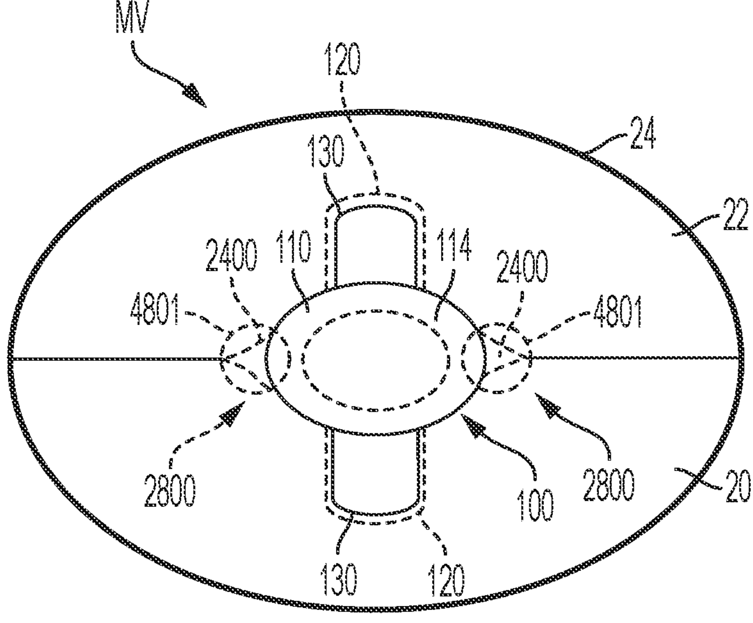
FIG. 55B shows the implantable prosthetic device implanted in the first position within the native valve shown in FIG. 48B, viewed from an atrial side of the native valve.
Figure 56A:
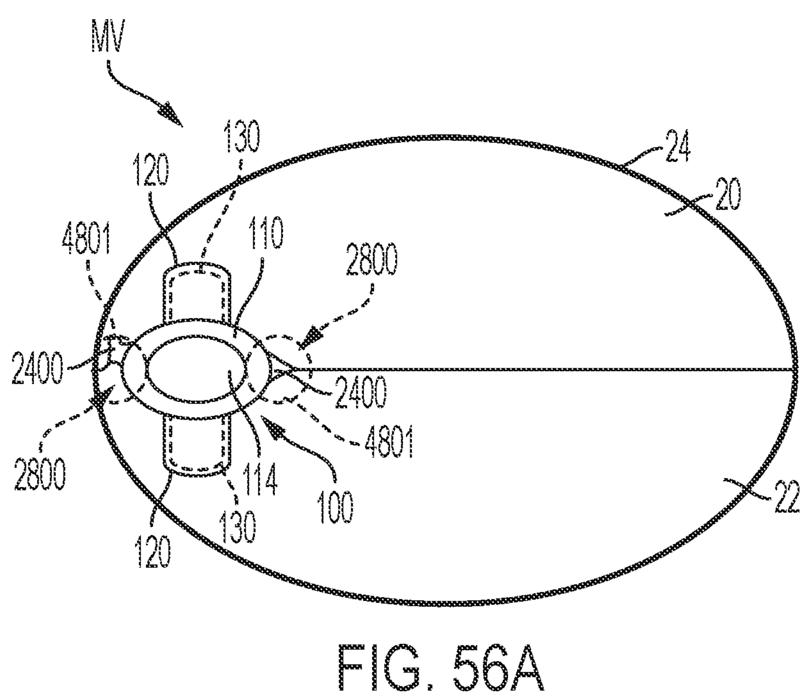
FIG. 56A shows the implantable prosthetic device of FIG. 48A implanted in a second example position within the native valve, viewed from the ventricle side of the native valve.
Figure 57A:
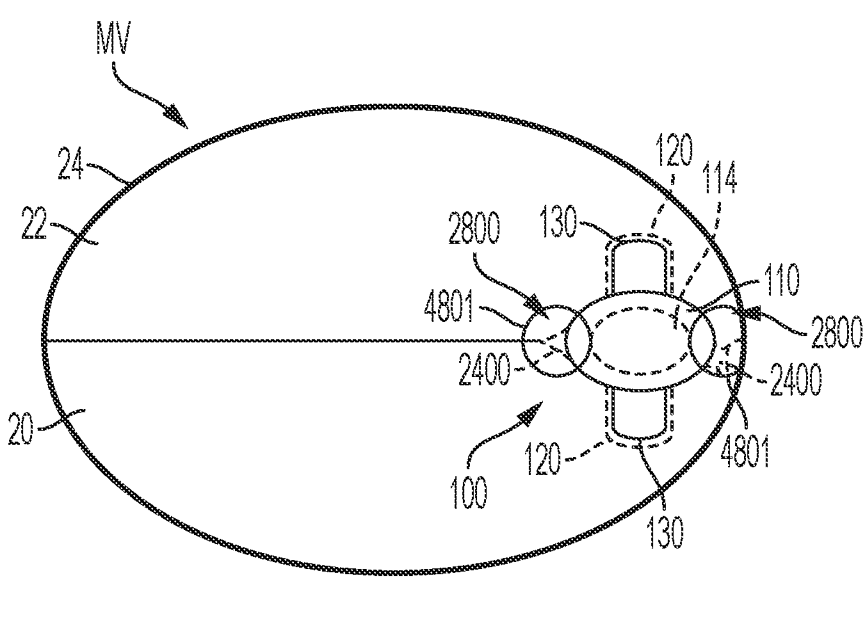
FIG. 57A shows the implantable prosthetic device of FIG. 48A implanted in the second example position within the native valve shown in FIG. 56A, viewed from the atrial side of the native valve.

Referring to FIGS. 56A and 57A, the device 100 shown in FIGS. 48A-55A can be placed within the mitral valve MV in a location near the annulus 24. Similar to the device 100 being located in a more central location within the mitral valve MV (as shown in FIGS. 48A-55A), openings 2400 may form where both leaflets 20, 22 and the device 100 meet. As shown in the illustrated embodiment, when the device 100 is placed near the annulus 24, the force on the mitral valve MV by the device 100 may cause the opening 2400 adjacent to the annulus 24 to have a deformed shape. In some embodiments, the flexible frame 4801 of the leak control extensions 2800 are flexible such that forces applied to the leak control extensions 2800 cause the flexible frame 4801 to compress. For example, as shown in FIGS. 56A and 57A, the leak control extension 2800 adjacent to the annulus 24 is pressed against the annulus 24 (or the side wall of the left ventricle LV), which causes the flexible frame 4801 to compress into a deformed shape. This compression of the flexible frame 4801 allows the leak control extensions to cover the deformed opening 2400 that is adjacent to the annulus 24. The flexible leak control extensions 2800 are advantageous because it allows the device 100 to be positioned within the mitral valve MV at various locations. In addition, the flexible leak control extensions 2800 are advantageous because they are capable of taking the form of any deformed openings caused by the connection between the device 100 and the leaflets 20, 22.

Figure 80:
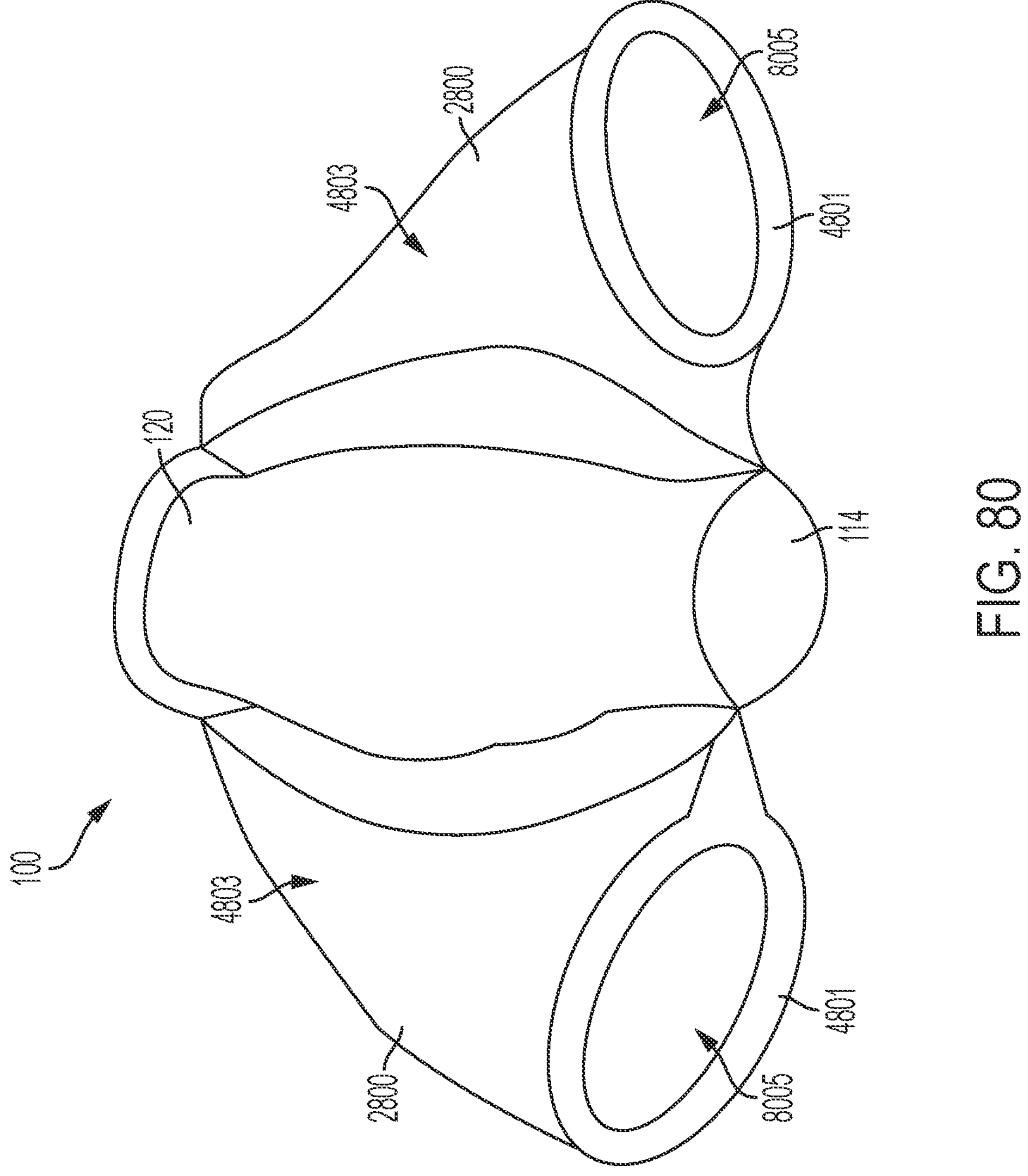
FIG. 80 is a front view of a more specific example of the implantable prosthetic device shown in FIGS. 48A-57A.
Figure 81:
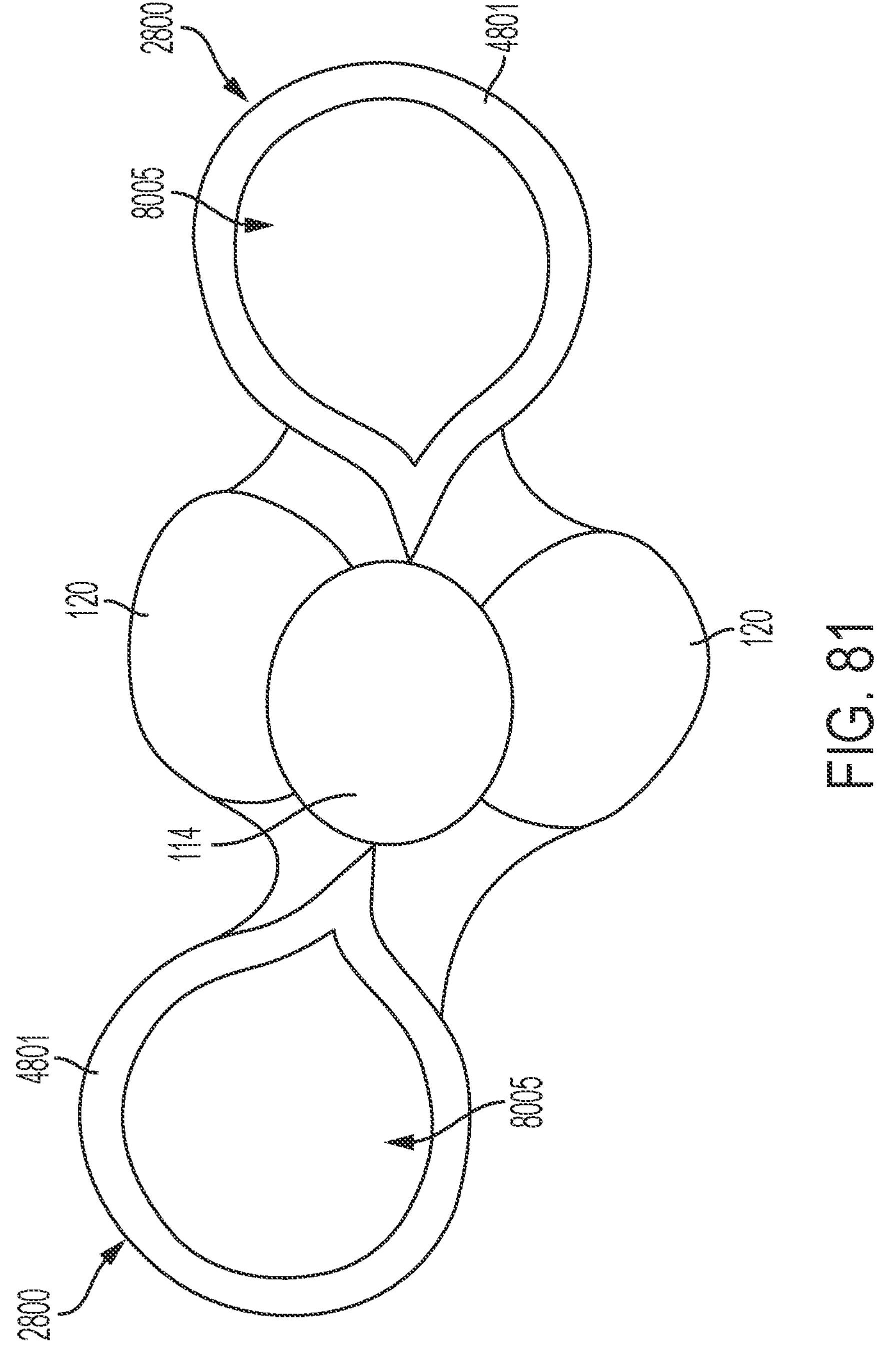
FIG. 81 is a bottom view of the implantable prosthetic device shown in FIG. 80.
Figure 82:
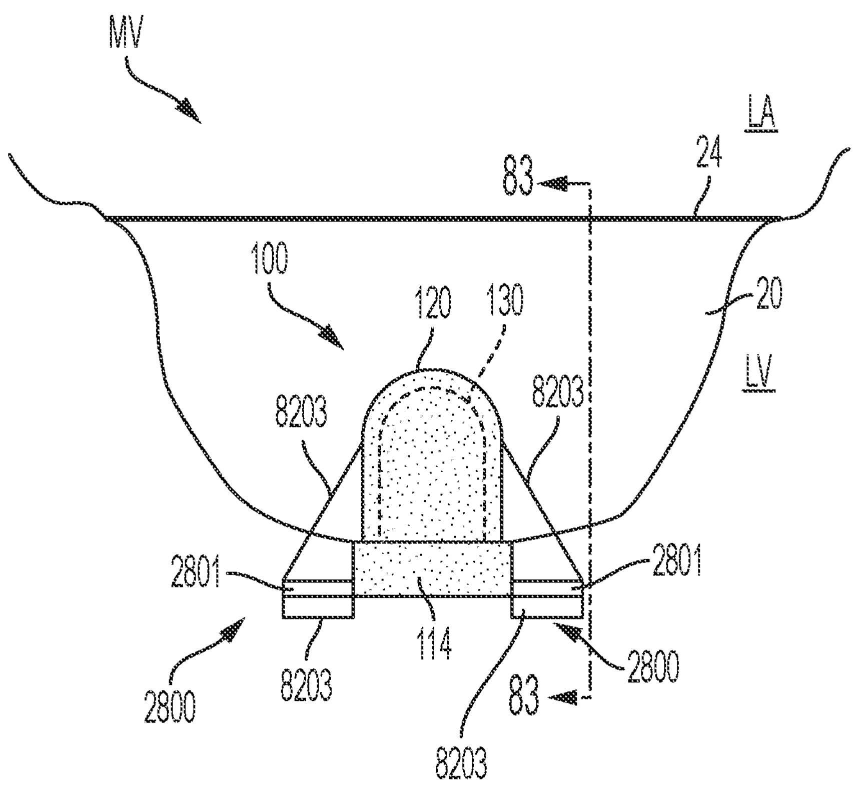
FIG. 82 shows an example of an implantable prosthetic device implanted in a first example position within the native valve.
Figure 83:
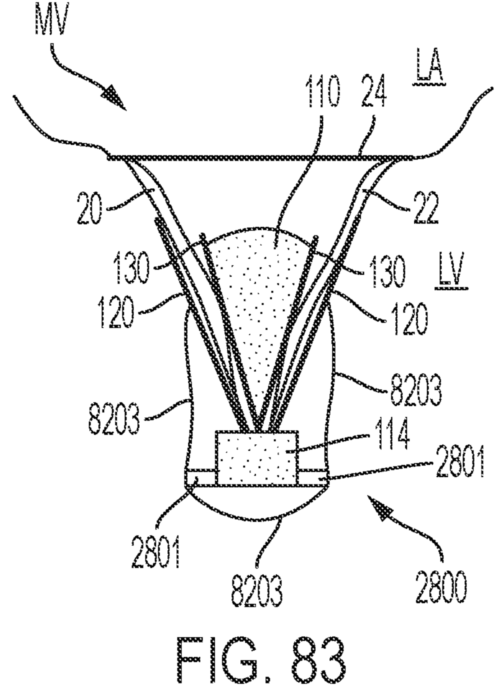
FIG. 83 is a cross-sectional view of the implantable prosthetic device implanted in the first position within the native valve shown in FIG. 82, with the section taken along the plane indicated by line 83-83 in FIG. 82.

FIGS. 80 and 81 illustrate a more specific example of the implantable prosthetic device 100 shown in FIGS. 48A-57A. The device 100 includes a pair of paddles 120, a pair of clasps (not shown), a coaption element (e.g., a spacer, etc.), a cap 114, and a pair of leak control extensions 2800. The leak control extensions 2800 have a flexible frame 4801 that defines an opening 8005 of the pocket and a barrier material 4803 that defines the interior of the pocket. In the illustrated embodiment, the flexible frame 4801 is formed to give the opening 8005 a circular shape. The barrier material 4803 is configured to capture the blood such that the blood does not move through the leak control extension 2800.

FIGS. 48B-57B show an example implantable prosthetic device 100 attached to the leaflets 20, 22 of a native valve (illustrated, for example, as mitral valve MV, but could be similarly used on another valve such as the tricuspid valve) in the fully closed position, where the device 100 includes one or more leak control extensions 2800. In the embodiment shown in FIGS. 48B-55B, the implantable prosthetic device 100 is attached to the native valve at a substantially central location, with the leak control extensions 2800 between the bottom of the native valve leaflets and the native valve annulus. It should be understood, however, that the implantable prosthetic device 100 can be attached to the leaflets 20, 22 at any location (e.g., the location shown in FIGS. 56B-57B). The device 100 has a pair of paddles 120, a pair of clasps 130, a coaption element 110 (e.g., a spacer, etc.), a cap 114, and at least one leak control extension 2800. However, the implantable prosthetic device 100 can take any suitable form, such as, for example, any formed described in the present application in combination with at least one leak control extension 2800.

The leak control extension(s) 2800 are configured to prevent blood from regurgitating from the ventricle and into the atrium during the systolic phase. That is, the leak control extension(s) 2800 extend from the device such that the leak control extensions are positioned to block blood moving through openings between the leaflets 20, 22 of the native valve during the systolic phase. In the illustrated embodiment, the leak control extensions 2800 are pockets that are configured for receiving blood to prevent the blood from moving into the atrium. In some embodiments, the leak control extensions 2800 can have a flexible frame or loop 4801 that defines an opening of the pocket and a barrier material 4803 that defines the interior of the pocket. The flexible frame 4801 can have any suitable shape for defining the opening of the pocket, such as, for example, a circular shape (as shown in FIGS. 54B-57B), an oval shape, a triangular shape, a polygonal shape, etc. The flexible frame 4801 can be made of, for example, a metal wire, such as a steel or nitinol wire, plastic, etc. The barrier material 4803 is configured to capture the blood such that the blood does not move through the leak control extension 2800. The barrier material 4803 can be made of, for example, a cloth material, a biocompatible material, bovine or porcine heart tissue, a plastic membrane, etc.

In the illustrated embodiment, the device 100 has two leak control mechanisms or leak control extensions 2800 that are attached to the coaption element or spacer 110 (See FIG. 55B). In the illustrated embodiment, when the device 100 is attached to the leaflets 20, 22, a portion of the leak control extensions 2800 are in the atrium and another portion of the leak control extensions 2800 are in the ventricle such that the opening of the leak control extensions 2800 are positioned in the ventricle. The leak control extensions 2800 can, however, be attached to any other portion of the device 100 that allows the leak control extensions 2800 to be positioned to prevent blood from regurgitating into the atrium, and the opening of the leak control extensions 2800 can be in either the atrium or the ventricle. For example, the leak control extensions 2800 can be attached to the pair of paddles 120, the pair of clasps 130, the coaption element 110, the cap 114, or any combination thereof. While the illustrated embodiment is shown as having two leak control extensions 2800, it should be understood that the device 100 can have any suitable number of leak control extensions.

Figure 50B:
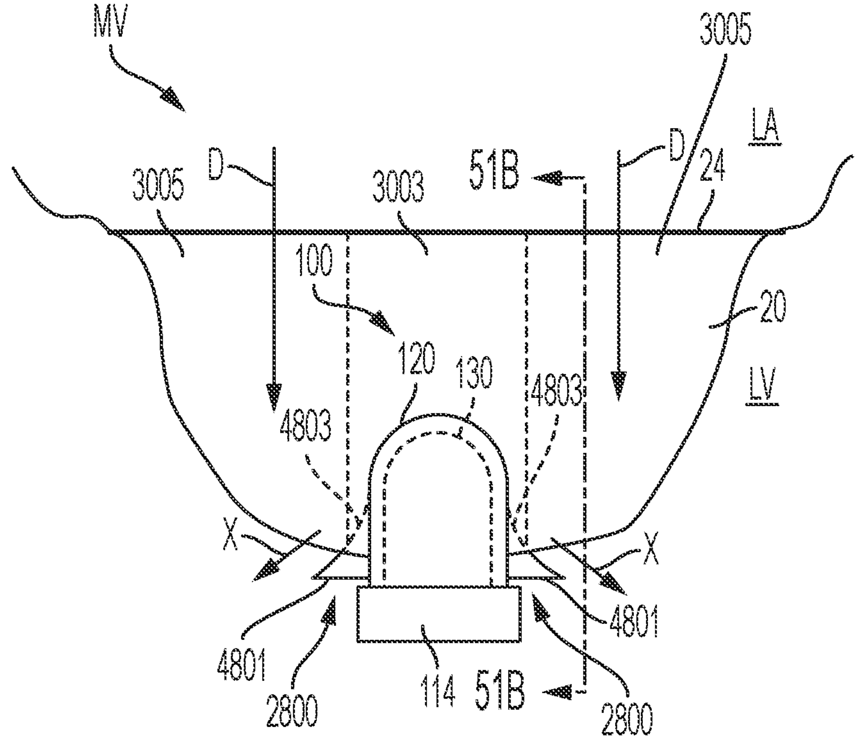
FIG. 50B shows the implantable prosthetic device implanted in the first position within the native valve shown in FIG. 48B, viewed when the heart is in a diastolic phase.
Figure 51B:
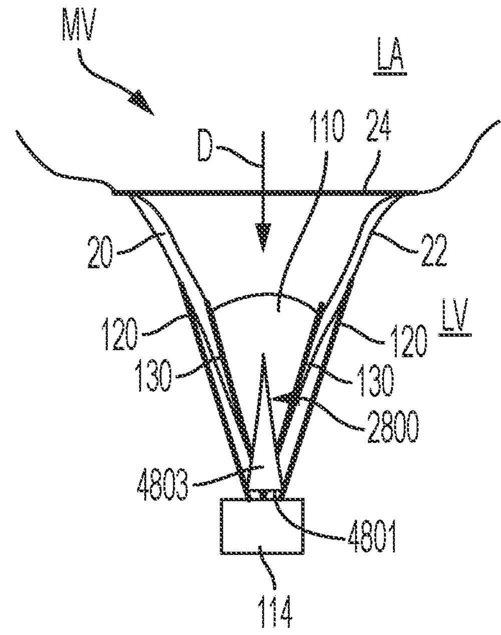
FIG. 51B is a cross-sectional view of the implantable prosthetic device implanted in the first position within the native valve shown in FIG. 50B, with the section taken along the plane indicated by line 51B-51B shown in FIG. 50B.

Referring to FIGS. 50B and 51B, during the diastolic phase, the leaflets 20, 22 of the mitral valve MV open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the leak control extensions 2800. In some embodiments, the blood provides a force on the barrier material 4803 of the leak control extensions 2800 that causes the barrier material 4803 to be compressed, and causes the blood to move around the leak control extensions 2800 in the direction X.

Referring to FIGS. 52B-55B, during the systolic phase, the leaflets 20, 22 of the mitral valve MV coapt to prevent blood from regurgitating into the left atrium LA as blood is pushed from the left ventricle LV and into the aorta, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 are positioned to prevent blood from regurgitating into the left atrium through the one or more openings 2400.

Figure 52B:
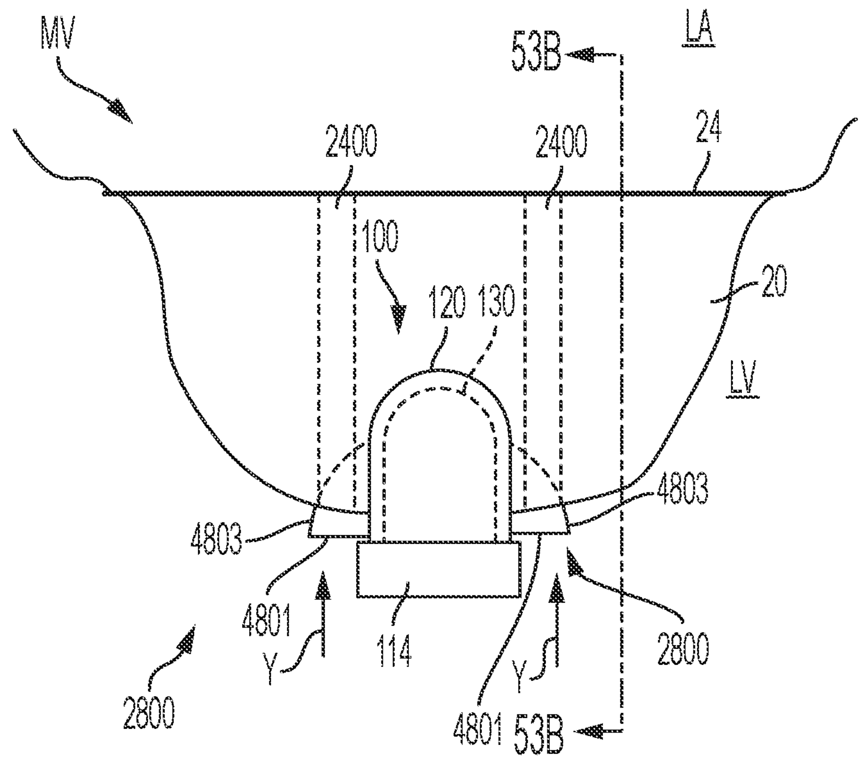
FIG. 52B shows the implantable prosthetic device implanted in the first position within the native valve shown in FIG. 48B, viewed when the heart is in a systolic phase.
Figure 53B:
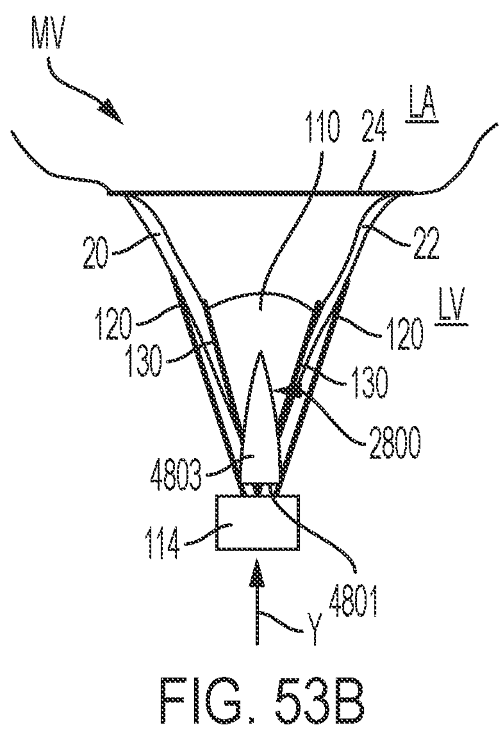
FIG. 53B is a cross-sectional view of the implantable prosthetic device implanted in the first position within the native valve shown in FIG. 52B, with the section taken along the plane indicated by line 53B-53B shown in FIG. 52B.
Figure 54A:
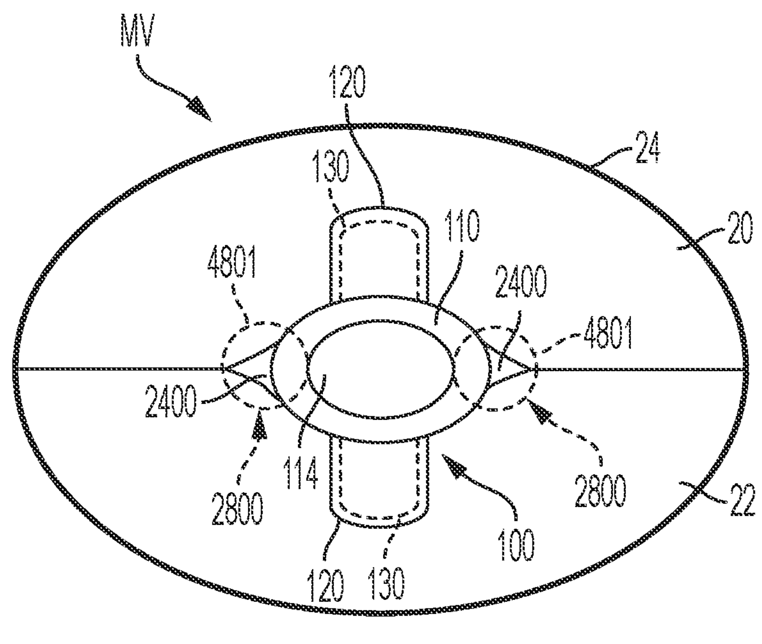
FIG. 54A shows the implantable prosthetic device implanted in the first position within the native valve shown in FIG. 48A, viewed from a ventricle side of the native valve.
Figure 54B:
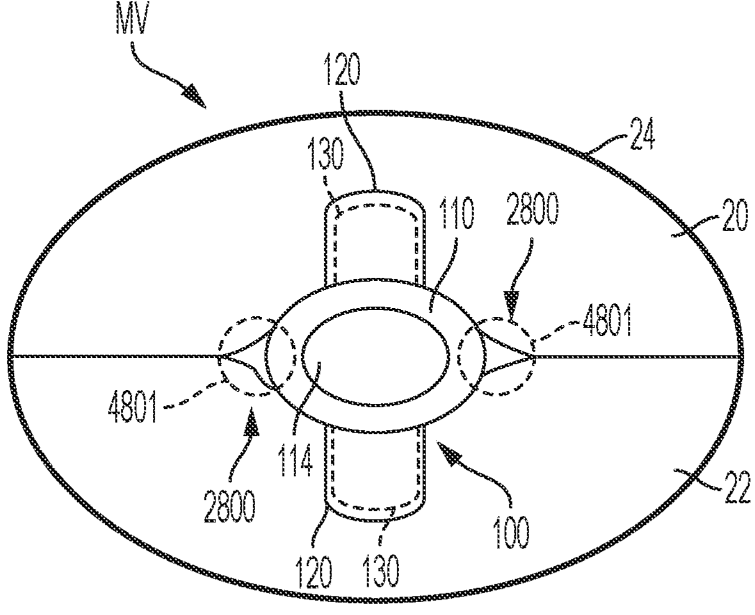
FIG. 54B shows the implantable prosthetic device implanted in the first position within the native valve shown in FIG. 48B, viewed from a ventricle side of the native valve.

Referring to FIGS. 52B and 53B, contraction of the left ventricle LV pushes blood toward the mitral valve MV in the direction Y and engages the leak control extensions 2800 in the mitral valve, which prevents additional blood from moving through the openings 2400 and into the left atrium LA. In some embodiments, such as the illustrated embodiment, the blood enters the leak control extensions 2800 and provides a force on the barrier material 4803 that causes the barrier material 4803 to expand.

Figure 56B:
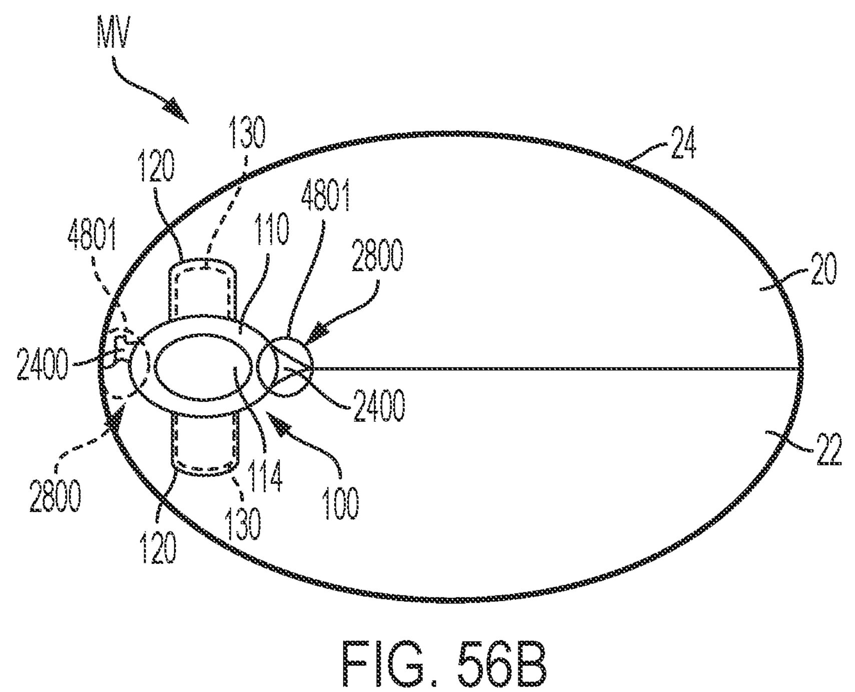
FIG. 56B shows the implantable prosthetic device of FIG. 48B implanted in a second example position within the native valve, viewed from the ventricle side of the native valve.
Figure 57B:
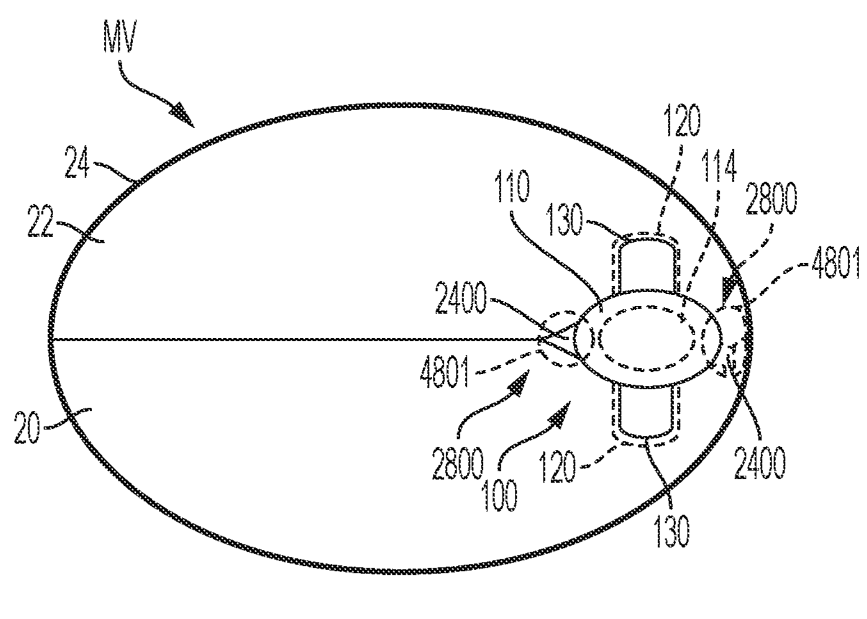
FIG. 57B shows the implantable prosthetic device of FIG. 48B implanted in the second example position within the native valve shown in FIG. 56B, viewed from the atrial side of the native valve.
Figure 58:
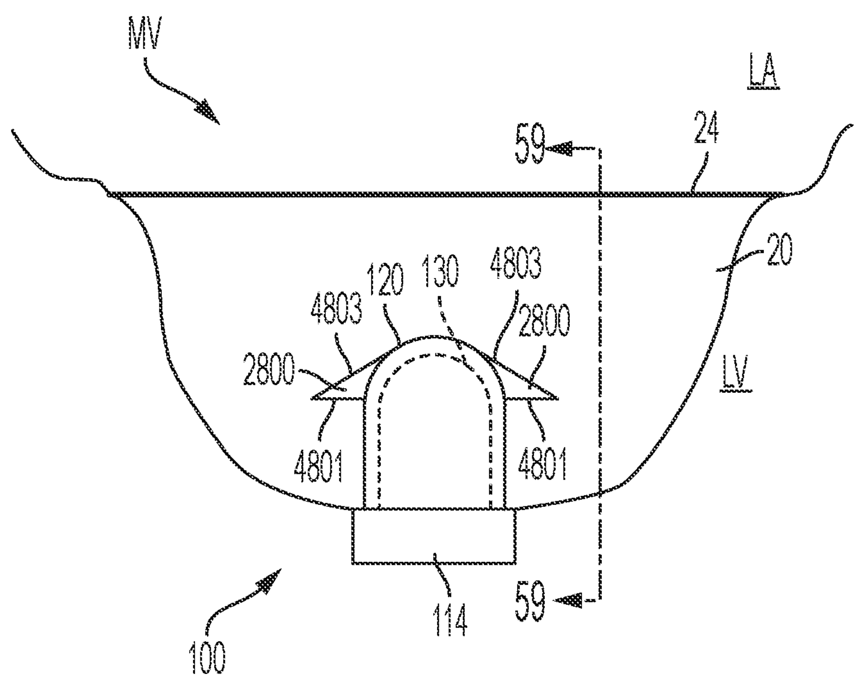
FIG. 58 shows an example of an implantable prosthetic device implanted in a first example position within the native valve.
Figure 59:
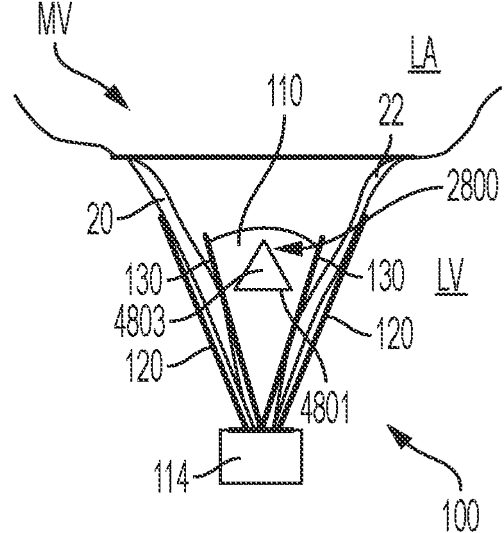
FIG. 59 is a cross-sectional view of the implantable prosthetic device implanted in the first position within the native valve shown in FIG. 58, with the section taken along the plane indicated by line 59-59 in FIG. 58.

Referring to FIGS. 56B and 57B, the device 100 shown in FIGS. 48B-55B can be placed within the native valve in a location near the annulus 24. Similar to the device 100 being located in a more central location within the native valve (as shown in FIGS. 54B-55B), openings 2400 may form where both leaflets 20, 22 and the device 100 meet. As shown in the illustrated embodiment, when the device 100 is placed near the annulus 24, the force on the native valve by the device 100 may cause the opening 2400 adjacent to the annulus 24 to have a deformed shape. In some embodiments, the flexible frame 4801 of the leak control extensions 2800 are flexible such that forces applied to the leak control extensions 2800 cause the flexible frame 4801 to compress. For example, as shown in FIGS. 56B and 57B, the leak control extension 2800 adjacent to the annulus 24 is pressed against the annulus 24 (or the side wall of the ventricle), which causes the flexible frame 4801 to compress into a deformed shape. This compression of the flexible frame 4801 allows the leak control extensions to cover the deformed opening 2400 that is adjacent to the annulus 24. The flexible leak control extensions 2800 are advantageous because it allows the device 100 to be positioned within the native valve at various locations. In addition, the flexible leak control extensions 2800 are advantageous because they are capable of taking the form of any deformed openings caused by the connection between the device 100 and the native leaflets.

FIGS. 58-67 show an example of an implantable prosthetic device 100 attached to leaflets 20, 22 of a native valve (illustrated, for example, as mitral valve MV, but could be similarly used on another valve such as the tricuspid valve). In the embodiment shown in FIGS. 58-65, the implantable prosthetic device 100 is attached to the native valve at a substantially central location of the valve leaflets. It should be understood, however, that the implantable prosthetic device 100 can be attached to the leaflets 20, 22 at any location (e.g., the location shown in FIGS. 56A-57A). In the example illustrated by FIGS. 58-67, the leak control extensions 2800 are positioned between the ends of the native valve leaflets and the native valve annulus. The device 100 has a pair of paddles 120, a pair of clasps 130, a coaption element 110 (e.g., a spacer, etc.), a cap 114, and at least one leak control extension 2800. However, the implantable prosthetic device 100 can take any suitable form, such as, for example, any formed described in the present application in combination with at least one leak control extension 2800.

The leak control extension(s) 2800 are configured to prevent blood from regurgitating from the ventricle and into the atrium during the systolic phase. In the example illustrated by FIGS. 58-67, the leak control extension(s) 2800 extend from the device such that the leak control extensions are positioned to block blood that flows through the openings between the leaflets 20, 22 of the native valve during the systolic phase. In the illustrated embodiment, the leak control extensions 2800 are pockets that are configured for receiving blood to block blood in the native valve that is moving toward the atrium.

In some embodiments, the leak control extensions 2800 can have a flexible frame or loop 4801 that defines an opening of the pocket and a barrier material 4803 that defines the interior of the pocket. The flexible frame 4801 can have any suitable shape for defining the opening of the pocket, such as, for example, a circular shape (as shown in FIGS. 64-67), an oval shape, a triangular shape, a polygonal shape, etc. The flexible frame 4801 can be made of, for example, a metal wire, such as a steel or nitinol wire, plastic, etc. The barrier material 4803 is configured to capture the blood such that the blood does not move through the leak control extension 2800. The barrier material 4803 can be made of, for example, a cloth material, a biocompatible material, bovine or porcine heart tissue, a plastic membrane, etc.

In the illustrated embodiment, the device 100 has two leak control extensions 2800 that are attached to the coaption element or spacer 110 at a top portion of the device 100. In some embodiments, the opening of the leak control extensions 2800 are positioned about midway between the native valve annulus and the ends of the native valve leaflets when the device 100 is attached to the leaflets 20, 22. The leak control extensions 2800 can be attached to any other portion of the device 100 that allows the leak control extensions 2800 to be positioned to block all or a portion of blood from regurgitating into the atrium, and the opening of the leak control extensions 2800 can be in either the atrium or the ventricle. For example, the leak control extensions 2800 can be attached to the pair of paddles 120, the pair of clasps 130, the coaption element 110, the cap 114, or any combination thereof. In addition, the leak control extensions 2800 can be positioned at any position along the height of the device 100. While the illustrated embodiment is shown as having two leak control extensions 2800, it should be understood that the device 100 can have any suitable number of leak control extensions.

Figure 60:
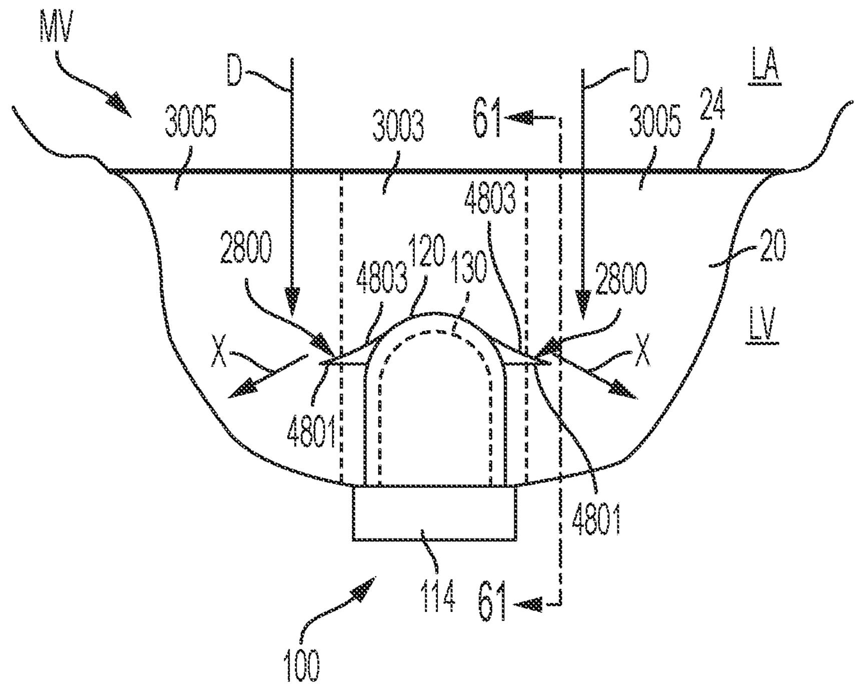
FIG. 60 shows the implantable prosthetic device implanted in the first position within the native valve shown in FIG. 58, viewed when the heart is in a diastolic phase.
Figure 61:
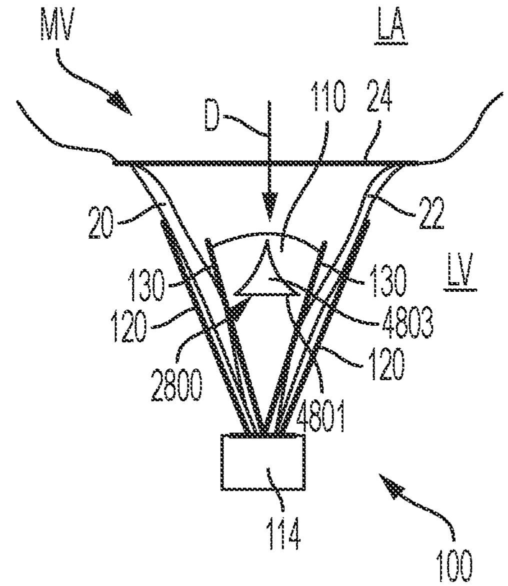
FIG. 61 is a cross-sectional view of the implantable prosthetic device implanted in the first position within the native valve shown in FIG. 60, with the section taken along the plane indicated by line 61-61 shown in FIG. 60.

Referring to FIGS. 60 and 61, during the diastolic phase, the leaflets 20, 22 of the native valve (shown as mitral valve MV) open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the leak control extensions 2800. In some embodiments, the blood provides a force on the barrier material 4803 of the leak control extensions 2800 that causes the barrier material 4803 to be compressed, and causes the blood to move around the leak control extensions 2800 in the direction X.

Referring to FIGS. 62-65, during the systolic phase, the leaflets 20, 22 of the mitral valve MV coapt to prevent blood from regurgitating into the left atrium LA as blood is pushed from the left ventricle and into the pulmonary artery PA, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 are positioned to block blood that regurgitates through the one or more openings 2400 from flowing into the left atrium.

Figure 62:
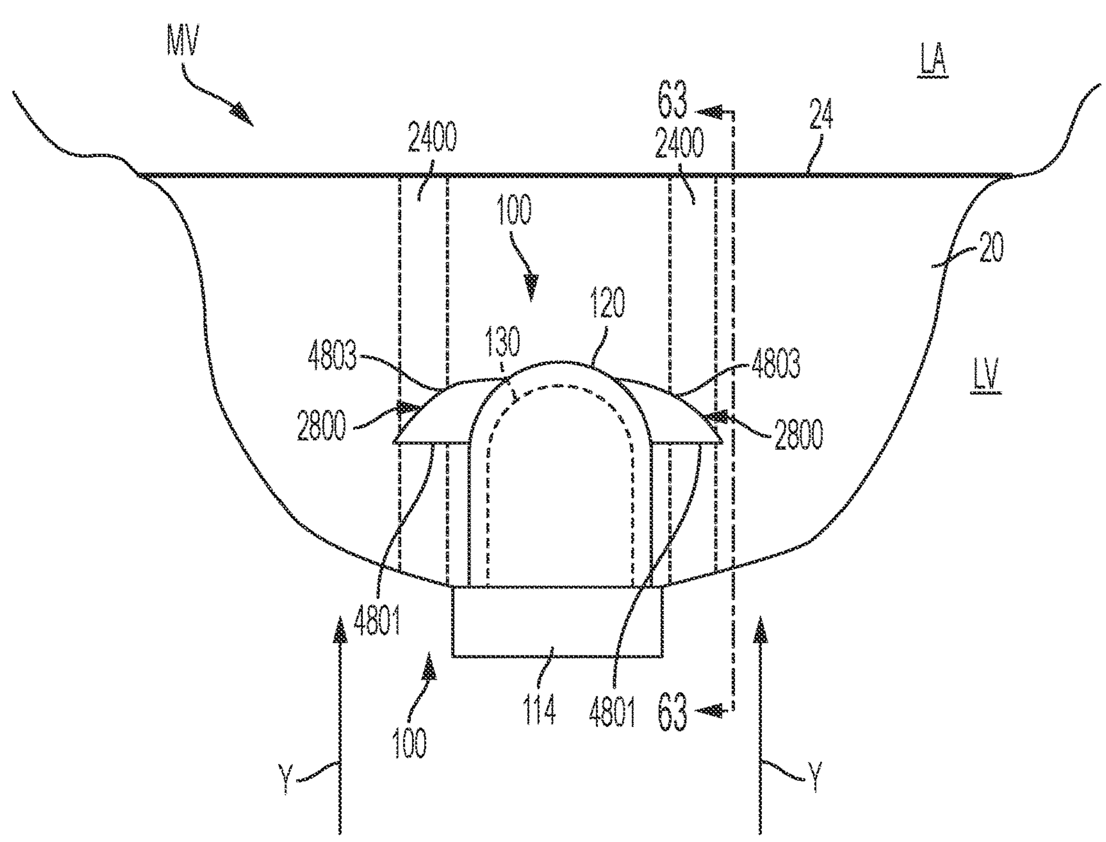
FIG. 62 shows the implantable prosthetic device implanted in the first position within the native valve shown in FIG. 58, viewed when the heart is in a systolic phase.
Figure 63:
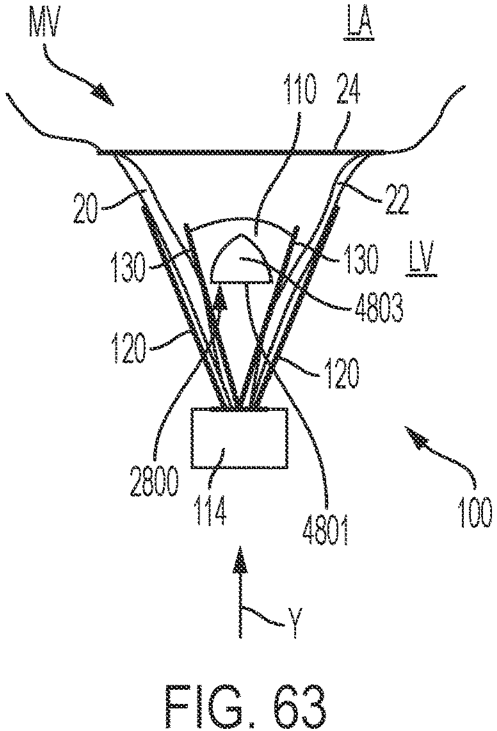
FIG. 63 is a cross-sectional view of the implantable prosthetic device implanted in the first position within the native valve shown in FIG. 62, viewed along the line 63-63 shown in FIG. 62.
Figure 64:
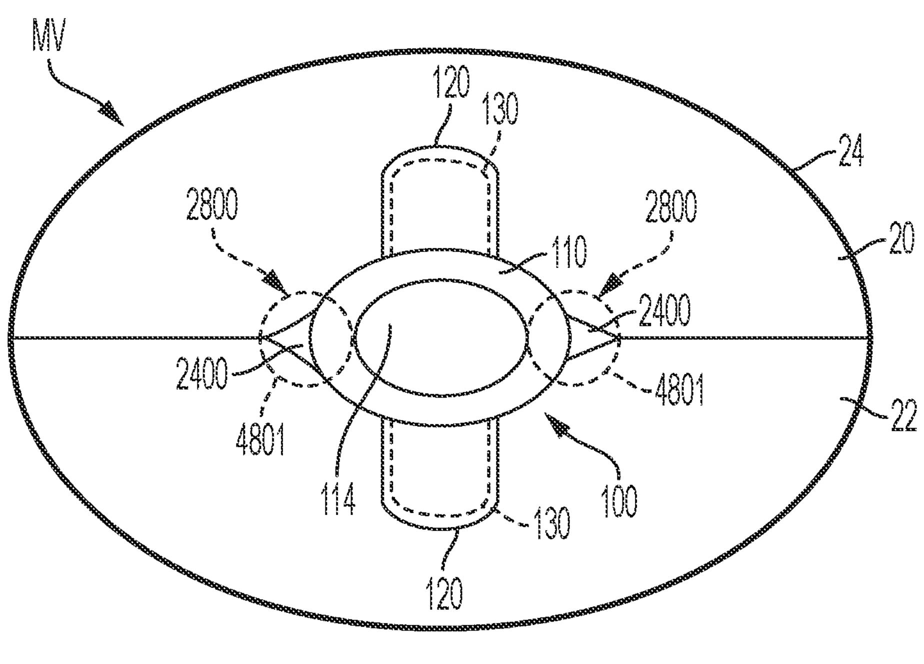
FIG. 64 shows the implantable prosthetic device implanted in the first position within the native valve shown in FIG. 58, viewed from a ventricle side of the native valve.
Figure 65:
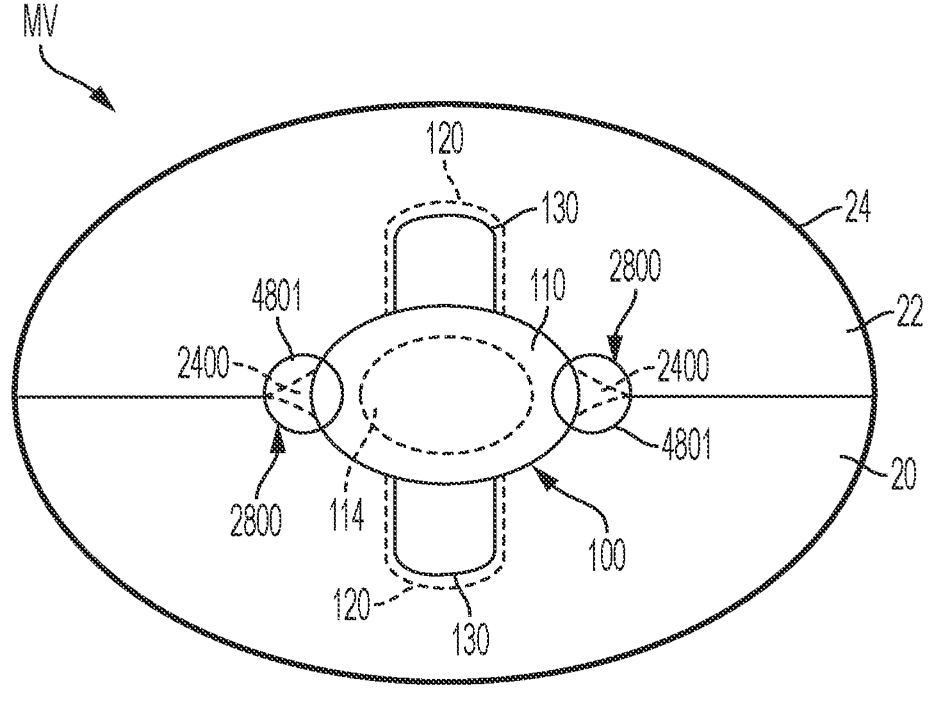
FIG. 65 shows the implantable prosthetic device implanted in the first position within the native valve shown in FIG. 58, viewed from an atrial side of the native valve.

Referring to FIGS. 62 and 63, contraction of the left ventricle LV pushes blood toward the mitral valve MV in the direction Y, through the openings 2400 and into engagement with the leak control extensions 2800. This engagement with the leak control extensions 2800 prevents the blood that flows through the openings 2400 from flowing into the left atrium LA. In some embodiments, such as the illustrated embodiment, the blood enters the leak control extensions 2800 and provides a force on the barrier material 4803 that causes the barrier material 4803 to expand.

Figures 66, 67:
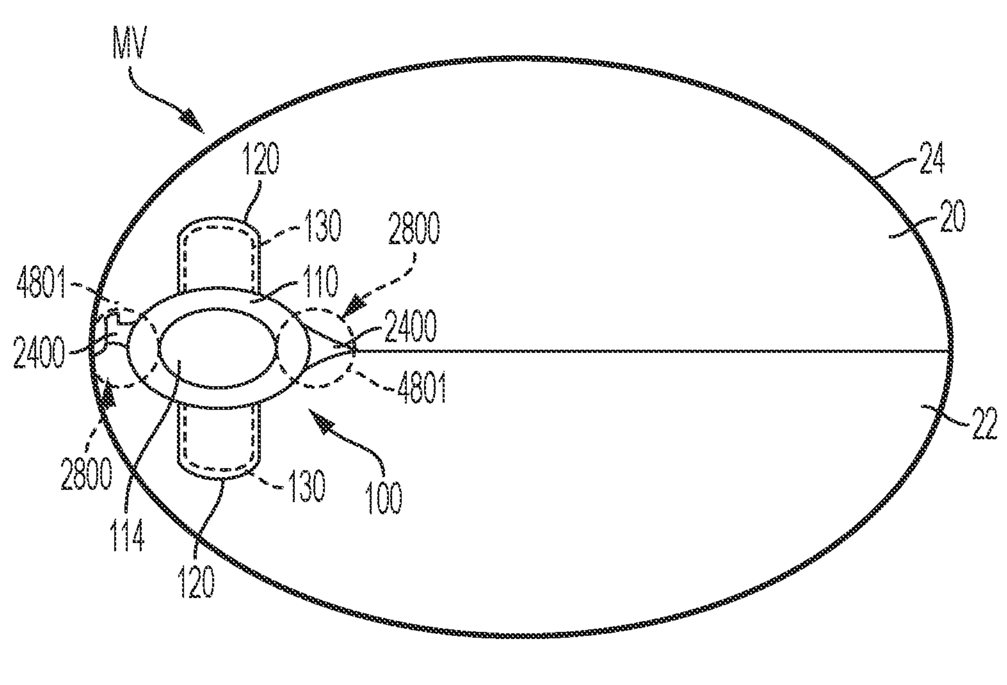
FIG. 66 shows the implantable prosthetic device of FIG. 58 implanted in a second example position within the native valve, viewed from the ventricle side of the native valve.
FIG. 67 shows the implantable prosthetic device of FIG. 58 implanted in the second example position within the native valve shown in FIG. 66, viewed from the atrial side of the native valve.
Figure 68:
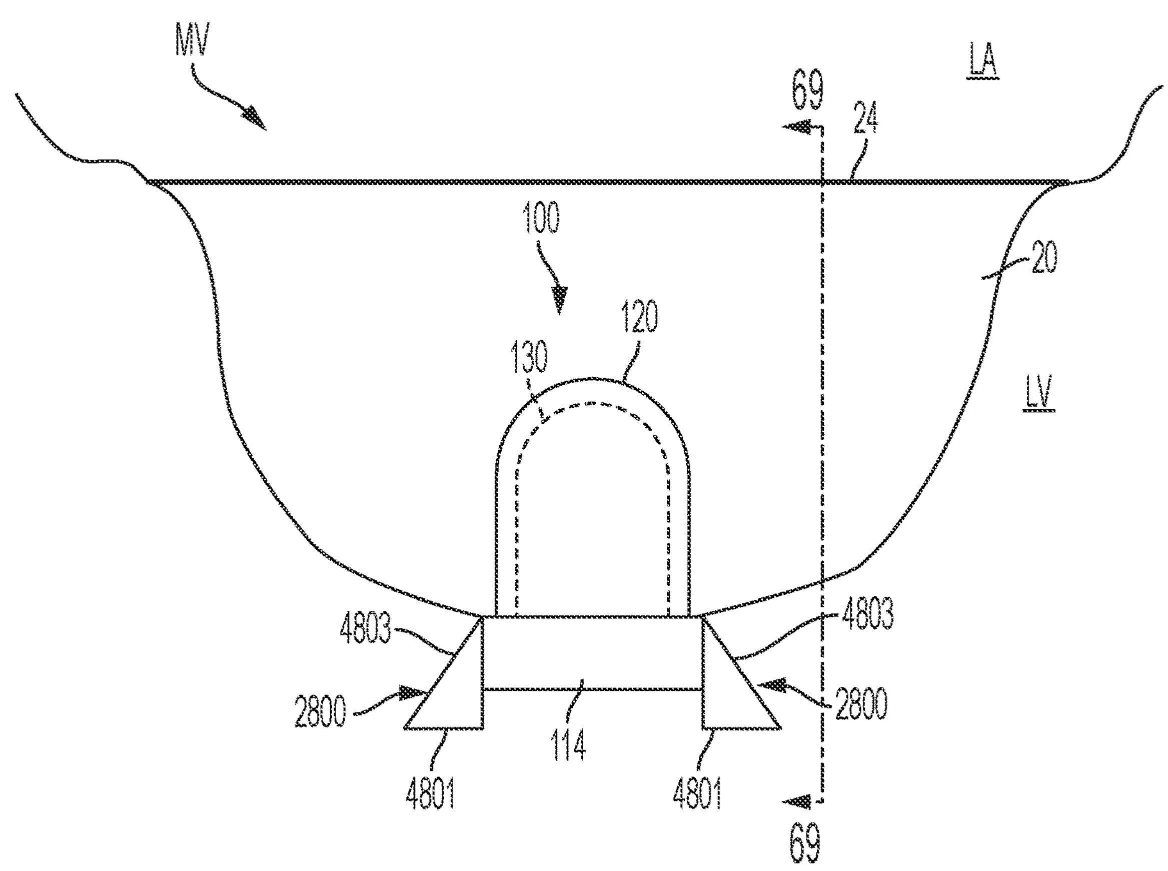
FIG. 68 shows an example of an implantable prosthetic device implanted in a first example position within the native valve.
Figure 69:
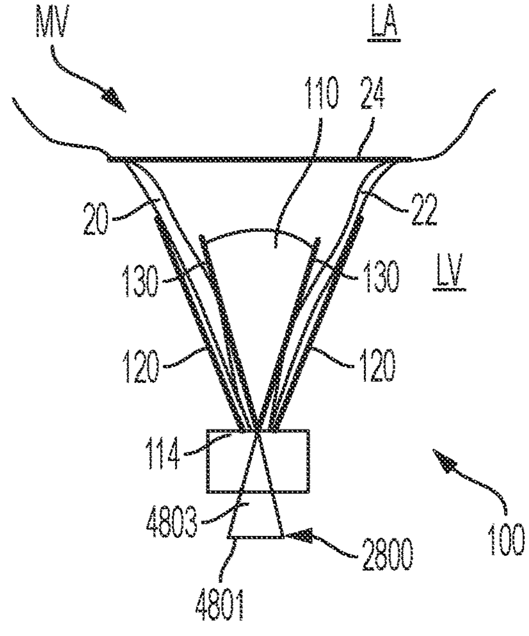
FIG. 69 is a cross-sectional view of the implantable prosthetic device implanted in the first position within the native valve shown in FIG. 68, with the section taken along the plane indicated by line 69-69 in FIG. 68.

Referring to FIGS. 66 and 67, the device 100 shown in FIGS. 58-65 can be placed within the native valve in a location near the annulus 24. Similar to the device 100 being located in a more central location within the native valve (as shown in FIGS. 58-65), openings 2400 may form where both leaflets 20, 22 and the device 100 meet. As shown in the illustrated embodiment, when the device 100 is placed near the annulus 24, the force on the native valve by the device 100 may cause the opening 2400 adjacent to the annulus 24 to have a deformed shape. In some embodiments, the flexible frame 4801 of the leak control extensions 2800 are flexible such that forces applied to the leak control extensions 2800 cause the flexible frame 4801 to compress. For example, as shown in FIGS. 66 and 67, the leak control extension 2800 adjacent to the annulus 24 is pressed against the annulus 24 (or the side wall of the ventricle), which causes the flexible frame 4801 to compress into a deformed shape. This compression of the flexible frame 4801 allows the leak control extensions to cover the deformed opening 2400 that is adjacent to the annulus 24. The flexible leak control extensions 2800 are advantageous because they allow the device 100 to be positioned within the native valve at various locations without causing irritation to the annulus 24 or the side walls of the ventricle or the atrium. In addition, the flexible leak control extensions 2800 are advantageous because they are capable of taking a form that can block flow of any deformed openings caused by the connection between the device 100 and the leaflets 20, 22.

FIGS. 68-77 show an example of an implantable prosthetic device 100 attached to leaflets 20, 22 of a native valve (illustrated, for example, as mitral valve MV, but could be similarly used on another valve such as the tricuspid valve) in the fully closed position. In the embodiment shown in FIGS. 68-75, the implantable prosthetic device 100 is attached to the native valve at a substantially central location within the annulus 24. It should be understood, however, that the implantable prosthetic device 100 can be attached to the leaflets 20, 22 at any location within the native valve (e.g., the location shown in FIGS. 66-67). The device 100 has a pair of paddles 120, a pair of clasps 130, a coaption element 110 (e.g., spacer, etc.), a cap 114, and at least one leak control extension 2800. However, the implantable prosthetic device 100 can take any suitable form, such as, for example, any formed described in the present application in combination with at least one leak control extension 2800.

The leak control extension(s) 2800 are configured to prevent blood from regurgitating from the ventricle and into the atrium during the systolic phase. That is, the leak control extension(s) 2800 extend from the device such that the leak control extensions are positioned to prevent blood from moving through any jets or openings between the leaflets 20, 22 of the native valve during the systolic phase. In the illustrated embodiment, the leak control extensions 2800 are pockets that are configured for receiving blood to prevent the blood from moving into the atrium. In some embodiments, the leak control extensions 2800 have a flexible frame 4801 that defines an opening of the pocket and a barrier material 4803 that defines the interior of the pocket.

The flexible frame 4801 can have any suitable shape for defining the opening of the pocket, such as, for example, a circular shape (as shown in FIGS. 74-77), an oval shape, a triangular shape, a polygonal shape, etc. The flexible frame 4801 can be made of, for example, a metal wire, such as a steel or nitinol wire, plastic, etc. The barrier material 4803 is configured to capture the blood such that the blood does not move through the leak control extension 2800. The barrier material 4803 can be made of, for example, a cloth material, a biocompatible material, bovine or porcine heart tissue, a plastic membrane, etc. In the illustrated embodiment, the device 100 has two leak control extensions 2800 that are attached to the cap 114.

In some embodiments, the opening of the leak control extensions 2800 are positioned in the ventricle when the device 100 is attached to the leaflets 20, 22. The leak control extensions 2800 can be attached to any other portion of the device 100 that allows the leak control extensions 2800 to be positioned to prevent blood from regurgitating into the atrium, and the opening of the leak control extensions 2800 can be in either the atrium or the ventricle. For example, the leak control extensions 2800 can be attached to the pair of paddles 120, the pair of clasps 130, the coaption element 110, the cap 114, or any combination thereof. In addition, the leak control extensions 2800 can be positioned at any position along the height of the device 100. While the illustrated embodiment is shown as having two leak control extensions 2800, it should be understood that the device 100 can have any suitable number of leak control extensions.

Figure 70:
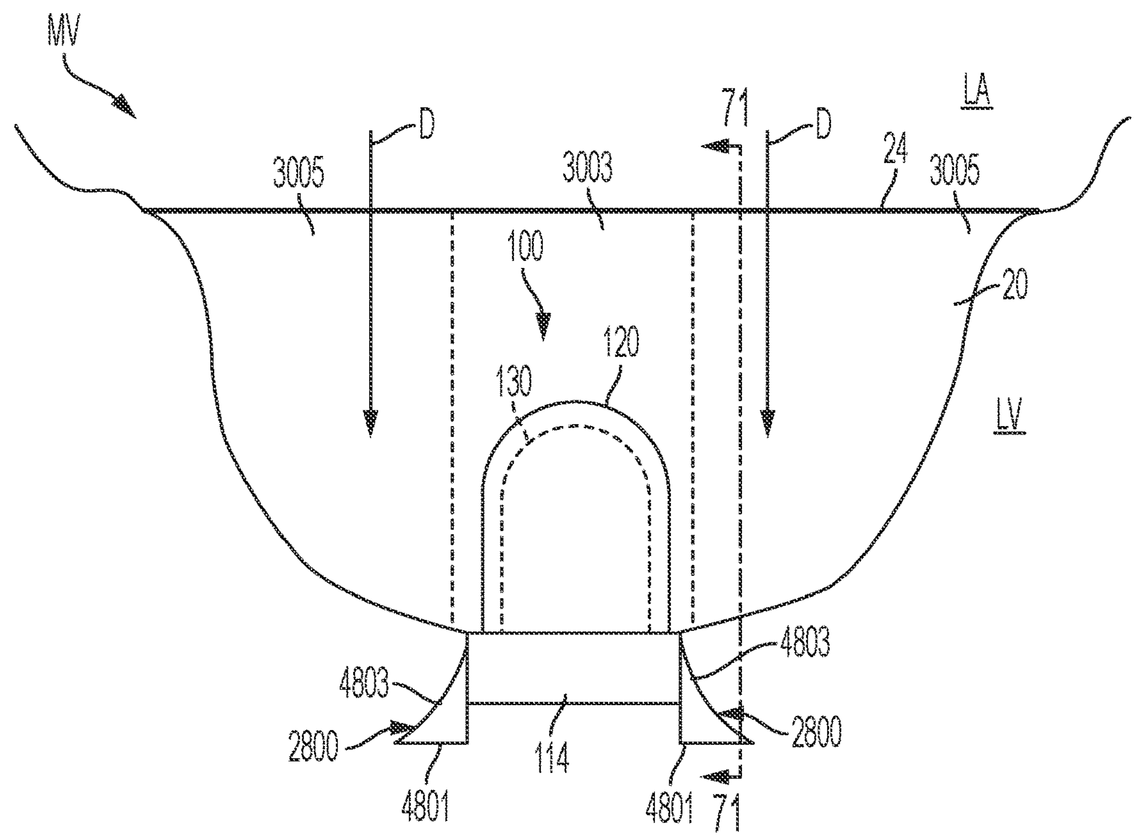
FIG. 70 shows the implantable prosthetic device implanted in the first position within the valve shown in FIG. 68, viewed when the heart is in a diastolic phase.
Figure 71:
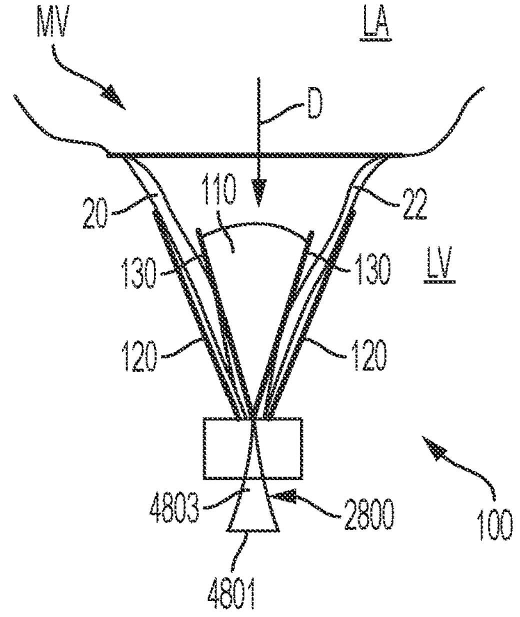
FIG. 71 is a cross-sectional view of the implantable prosthetic device implanted in the first position within the native valve shown in FIG. 70, with the section taken along the plane indicated by line 71-71 shown in FIG. 70.

Referring to FIGS. 70 and 71, during the diastolic phase, the leaflets 20, 22 of the native valve (illustrated as mitral valve MV) open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the leak control extensions 2800. In some embodiments, the blood provides a force on the barrier material 4803 of the leak control extensions 2800 that causes the barrier material 4803 to be compressed, and causes the blood to move around the leak control extensions 2800 in the direction X.

Referring to FIGS. 72-75, during the systolic phase, the leaflets 20, 22 of the mitral valve MV coapt to prevent blood from regurgitating into the left atrium LA as blood is pushed from the left ventricle and into the pulmonary artery PA, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 are positioned to prevent blood from regurgitating into the left atrium through the one or more openings 2400.

Figure 72:
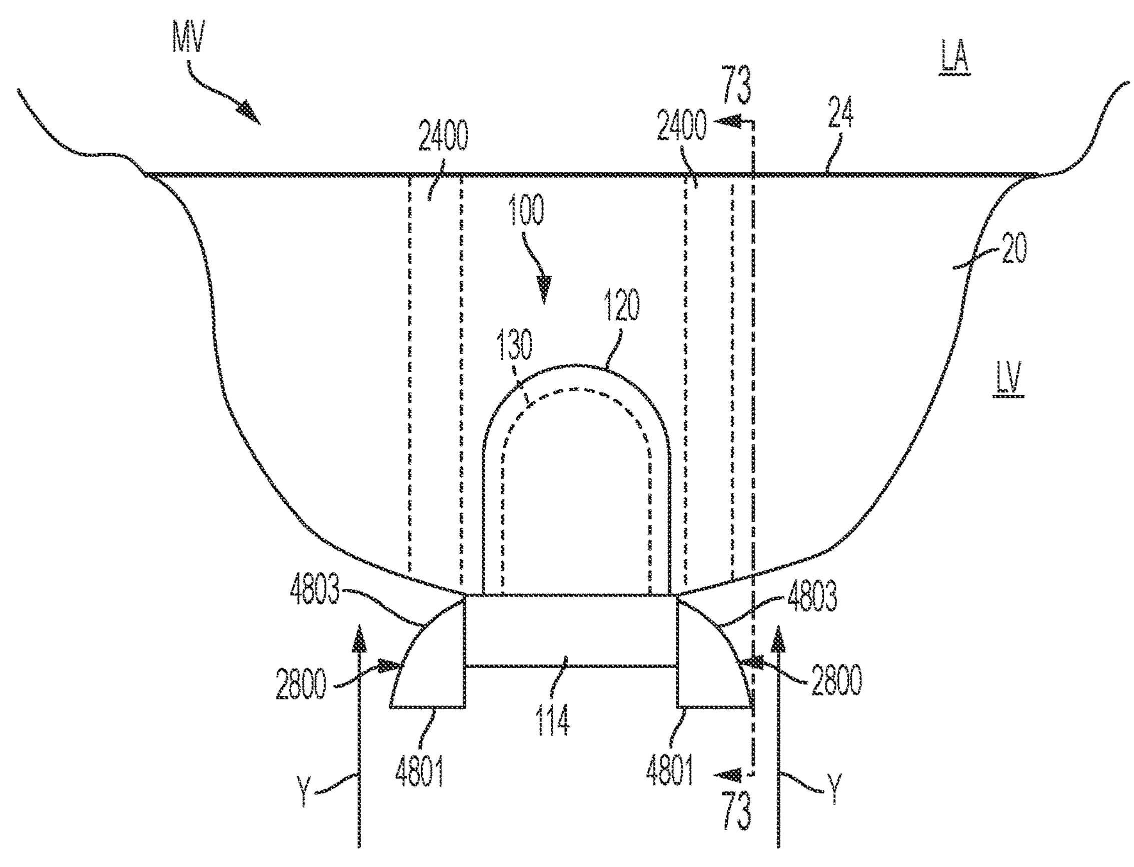
FIG. 72 shows the implantable prosthetic device implanted in the first position within the valve shown in FIG. 68, viewed when the heart is in a systolic phase.
Figure 73:
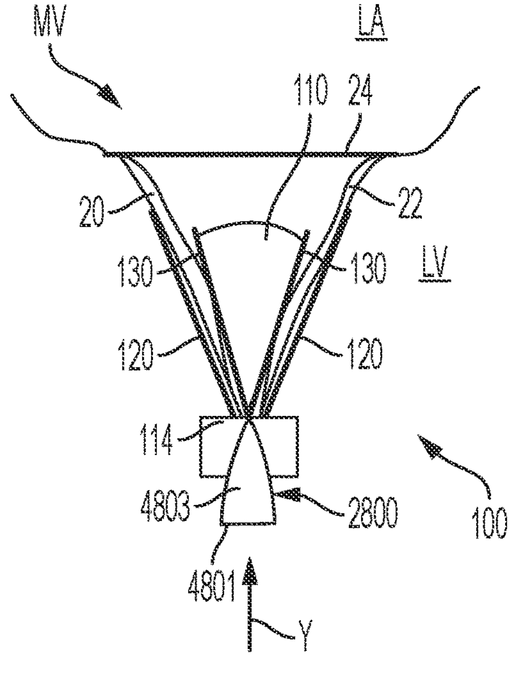
FIG. 73 is a cross-sectional view of the implantable prosthetic device implanted in the first position within the native valve shown in FIG. 72, with the section taken along the plane indicated by line 73-73 shown in FIG. 72.
Figure 74:
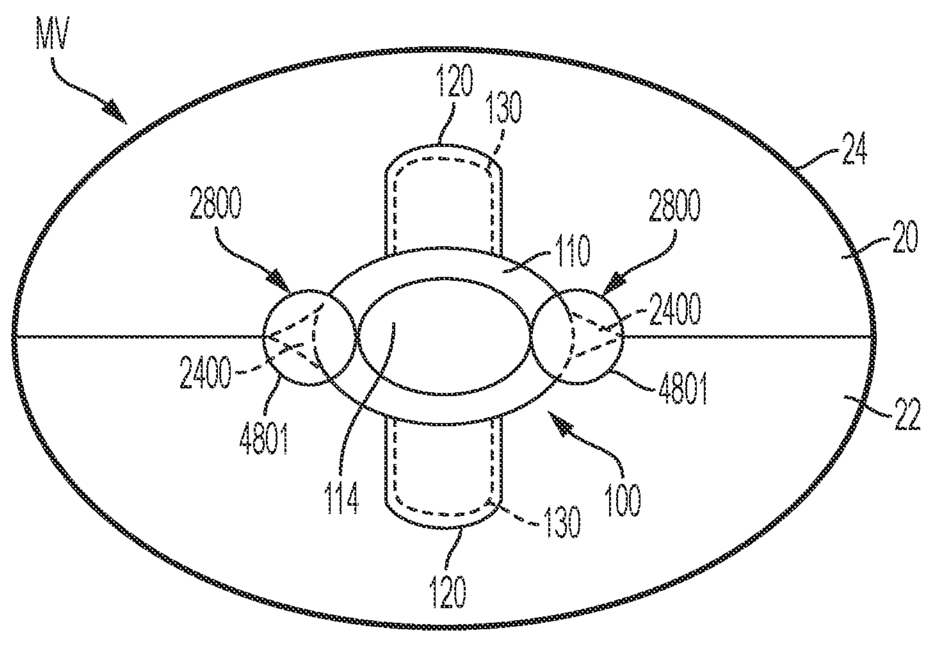
FIG. 74 shows the implantable prosthetic device implanted in the first position within the native valve shown in FIG. 68, viewed from a ventricle side of the native valve.
Figure 75:
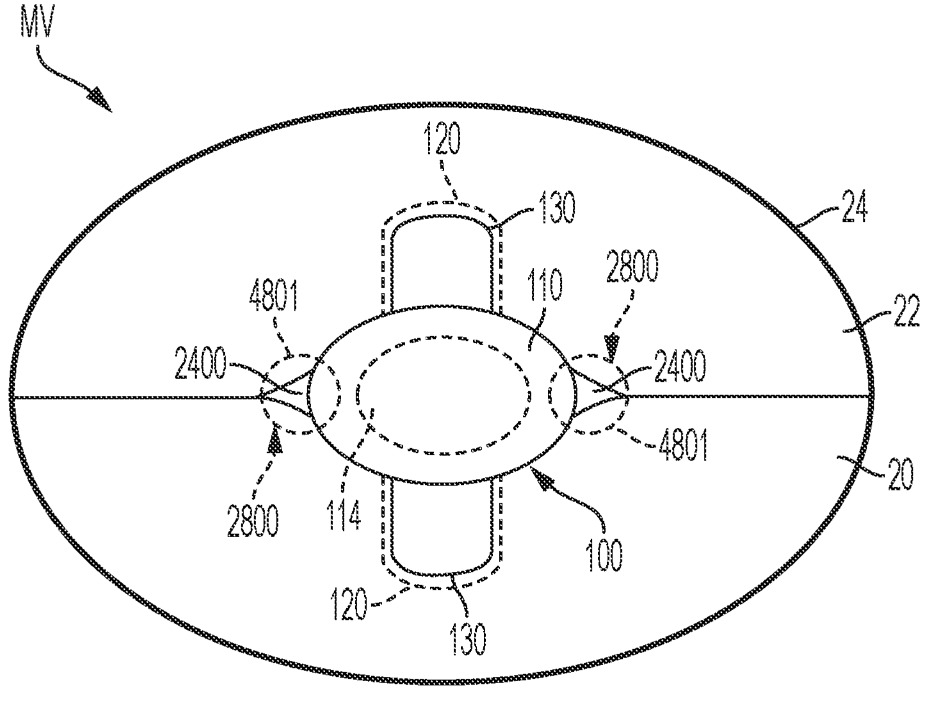
FIG. 75 shows the implantable prosthetic device implanted in the first position within the native valve shown in FIG. 68, viewed from an atrial side of the native valve.

Referring to FIGS. 72 and 73, contraction of the left ventricle LV pushes blood toward the mitral valve MV in the direction Y and engages the leak control extensions 2800, which prevents blood from moving through the openings 2400 and into the left atrium LA. In some embodiments, such as the illustrated embodiment, the blood enters the leak control extensions 2800 and provides a force on the barrier material 4803 that causes the barrier material 4803 to expand.

Figure 76:
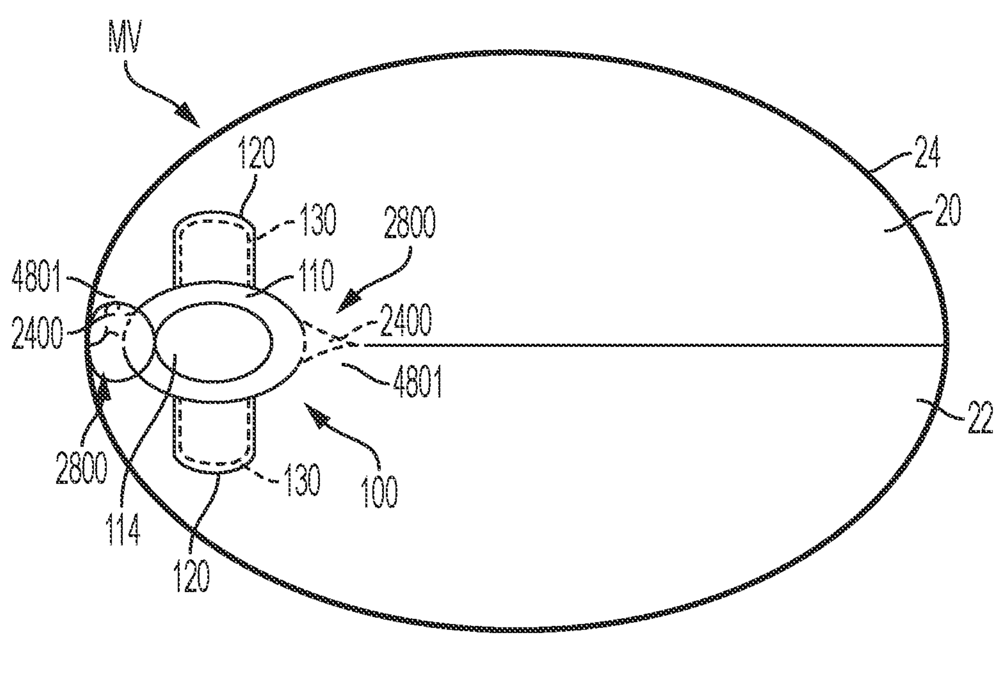
FIG. 76 shows the implantable prosthetic device of FIG. 68 implanted in a second example position within the native valve, viewed from the ventricle side of the native valve.
Figure 77:
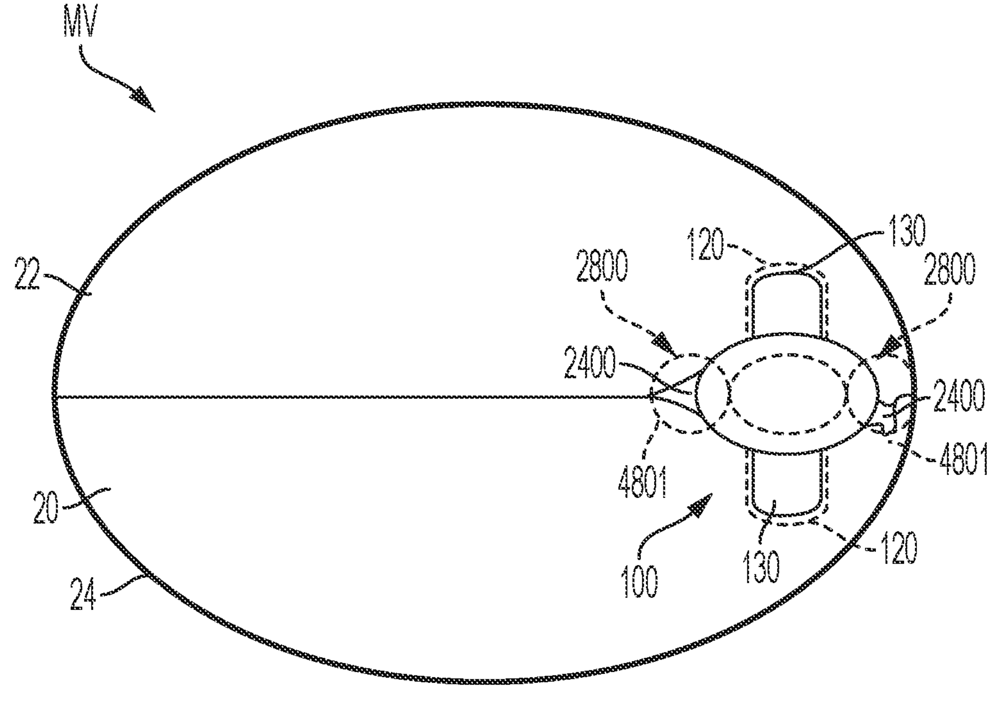
FIG. 77 shows the implantable prosthetic device of FIG. 68 implanted in the second example position within the native valve shown in FIG. 76, viewed from the atrial side of the native valve.

Referring to FIGS. 76 and 77, the device 100 shown in FIGS. 68-75 can be placed within the native valve in a location near the annulus 24. Similar to the device 100 being located in a more central location within the native valve (as shown in FIGS. 68-75), openings 2400 may form where both leaflets 20, 22 and the device 100 meet. As shown in the illustrated embodiment, when the device 100 is placed near the annulus 24, the force on the native valve by the device 100 may cause the opening 2400 adjacent to the annulus 24 to have a deformed shape.

In some embodiments, the flexible frame 4801 of the leak control extensions 2800 are flexible such that forces applied to the leak control extensions 2800 cause the flexible frame 4801 to compress or deform. For example, as shown in FIGS. 76 and 77, the leak control extension 2800 adjacent to the annulus 24 is pressed against the annulus 24 (or the side wall of the ventricle), which causes the flexible frame 4801 to compress into a deformed shape. This compression of the flexible frame 4801 allows the leak control extensions to cover the deformed opening 2400 that is adjacent to the annulus 24. The flexible leak control extensions 2800 are advantageous because it allows the device 100 to be positioned within the native valve at various locations without causing irritation to the annulus 24 or the side walls of the left ventricle or the atrium. In addition, the flexible leak control extensions 2800 are advantageous because they are capable of taking the form of any deformed openings caused by the connection between the device 100 and the leaflets 20, 22.

FIGS. 82-91 show an example of an implantable prosthetic device 100 attached to leaflets 20, 22 of a native valve (illustrated, for example, as mitral valve MV, but could be similarly used on another valve such as the tricuspid valve) in the fully closed position, where the device 100 includes one or more leak control extensions 2800. In the embodiment shown in FIGS. 82-89, the implantable prosthetic device 100 is attached to the native valve at a substantially central location within the annulus 24. It should be understood, however, that the implantable prosthetic device 100 can be attached to the leaflets 20, 22 at any location within the native valve (e.g., the location shown in FIGS. 90-91). The device 100 has a pair of paddles 120, a pair of clasps 130, a coaption element 110 (e.g., a spacer etc.), a cap 114, and at least one leak control extension 2800. However, the implantable prosthetic device 100 can take any suitable form, such as, for example, any formed described in the present application in combination with at least one leak control extension 2800.

The leak control extension(s) 2800 are configured to prevent blood from regurgitating from the ventricle and into the atrium during the systolic phase. That is, the leak control extension(s) 2800 extend from the device (e.g., from the end of the cap 114 of the device 100) such that the leak control extensions are positioned to prevent blood from moving through any jets or openings between the leaflets 20, 22 of the native valve during the systolic phase. Each of the leak control extensions 2800 can include one or more deflecting paddles 2801 (or other extension members) and a barrier element 8203. The one or more deflecting paddles 2801 can attach to the cap 114 of the device 100 (or any other portion of the device), and the barrier element 8203 can attach to the paddles 120 and the deflecting paddles 2801 to create a barrier that extends from a first paddle 120 of the device 100 to a second paddle of the device 100, where the barrier prevents regurgitation of blood during the systolic phase. In the illustrated embodiment, the leak control extensions 2800 each include two deflecting paddles 2801 that are attached to the cap 114 and a barrier element 8203 that connects to and extends from a first paddle 120, the two deflecting paddles 2801, and to the other paddle 120. The barrier element 8203 can include one or more pieces of material, such as, for example, one or more pieces of a cloth material, a biocompatible material, bovine or porcine heart tissue, a plastic membrane, etc. In the illustrated embodiment, the device 100 has two leak control extensions 2800, where each leak control extension 2800 includes one or more deflecting paddles 2801 and a barrier material 8203. While the illustrated embodiment is shown as having two leak control extensions 2800, it should be understood that the device 100 can have any suitable number of leak control extensions.

Figure 84:
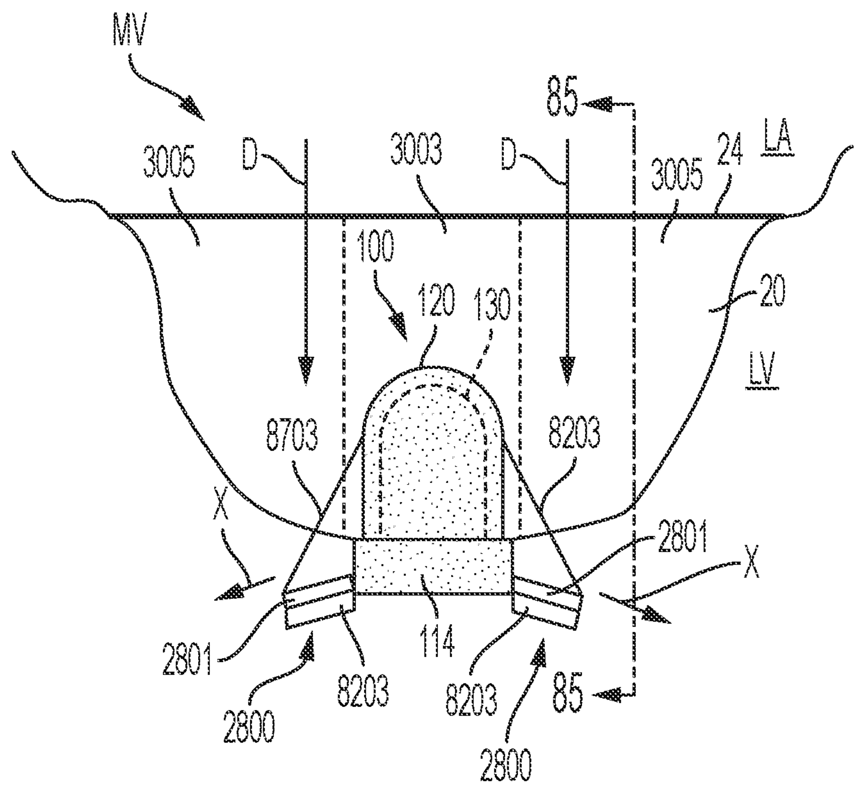
FIG. 84 shows the implantable prosthetic device implanted in the first position within the native valve shown in FIG. 82, viewed when the heart is in a diastolic phase.
Figure 85:
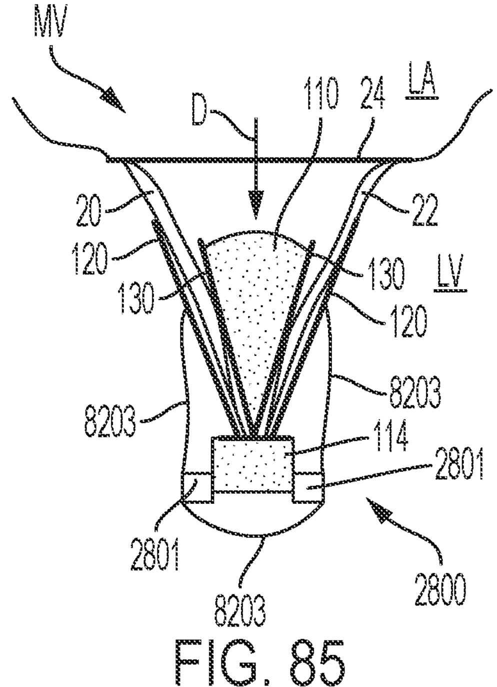
FIG. 85 is a cross-sectional view of the implantable prosthetic device implanted in the first position within the native valve shown in FIG. 84, with the section taken along the plane indicated by line 85-85 shown in FIG. 84.

Referring to FIGS. 84 and 85, during the diastolic phase, the leaflets 20, 22 of the mitral valve MV open and blood moves from the left atrium LA to the left ventricle LV. As the device 100 is connected to the leaflets 20, 22, a portion 3003 of the mitral valve MV is substantially blocked by the device 100 when the leaflets 20, 22 are in the open position, while other portion(s) 3005 of the mitral valve are open such that blood can move into the left ventricle LV. The blood moves through the open portions 3005 in the direction D and engages the leak control extensions 2800. In some embodiments, the blood provides a force on the leak control extensions 2800 that causes the deflecting paddles 2801 to pivot about the cap 114 or flex relative to the cap such that the blood moves around the leak control extensions 2800 in the direction X.

Referring to FIGS. 86-89, during the systolic phase, the leaflets 20, 22 of the mitral valve MV coapt to prevent blood from regurgitating into the left atrium LA as blood is pushed from the left ventricle and into the pulmonary artery PA, and the device 100 is connected to the leaflets 20, 22 to help facilitate the coapting or coaptation of the leaflets. In certain situations, however, the leaflets 20, 22 may not completely coapt around the device 100, which may cause one or more openings or jets 2400 to form between the device 100 and one or more of the leaflets 20, 22. The openings 2400 may form at the location where both leaflets 20, 22 and the device 100 meet. The openings 2400 can also form, however, at any point where the device 100 and a single leaflet 20, 22 meet. The leak control extensions 2800 can be positioned to prevent blood from regurgitating into the left atrium through the one or more openings 2400.

Figure 86:
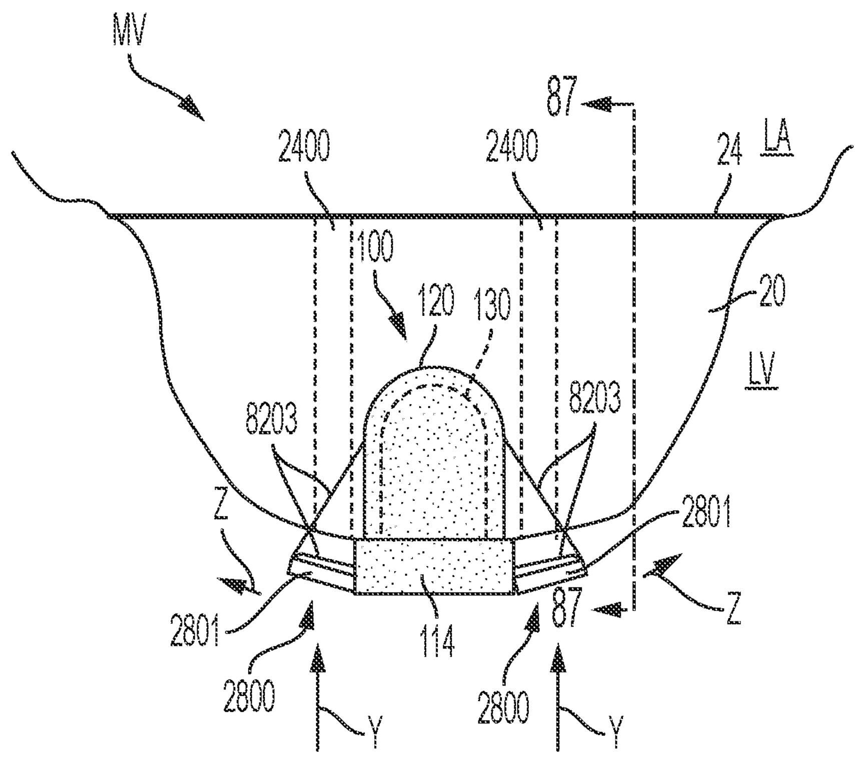
FIG. 86 shows the implantable prosthetic device implanted in the first position within the native valve shown in FIG. 82, viewed when the heart is in a systolic phase.
Figure 87:
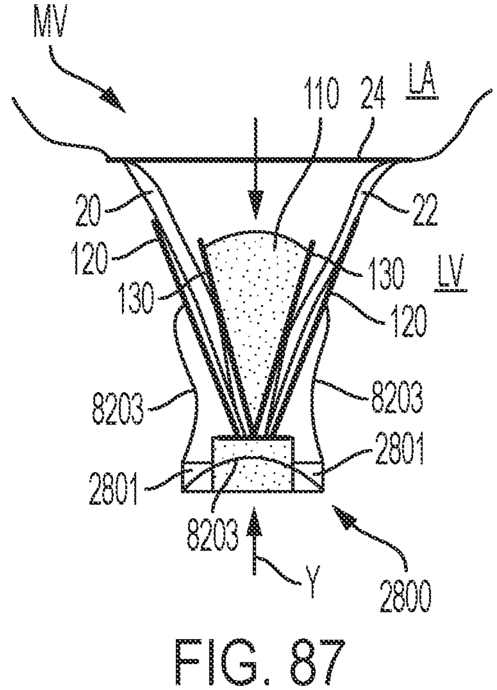
FIG. 87 is a cross-sectional view of the implantable prosthetic device implanted in the first position within the native valve shown in FIG. 86, viewed along the line 87-87 shown in FIG. 86.
Figures 88, 89:
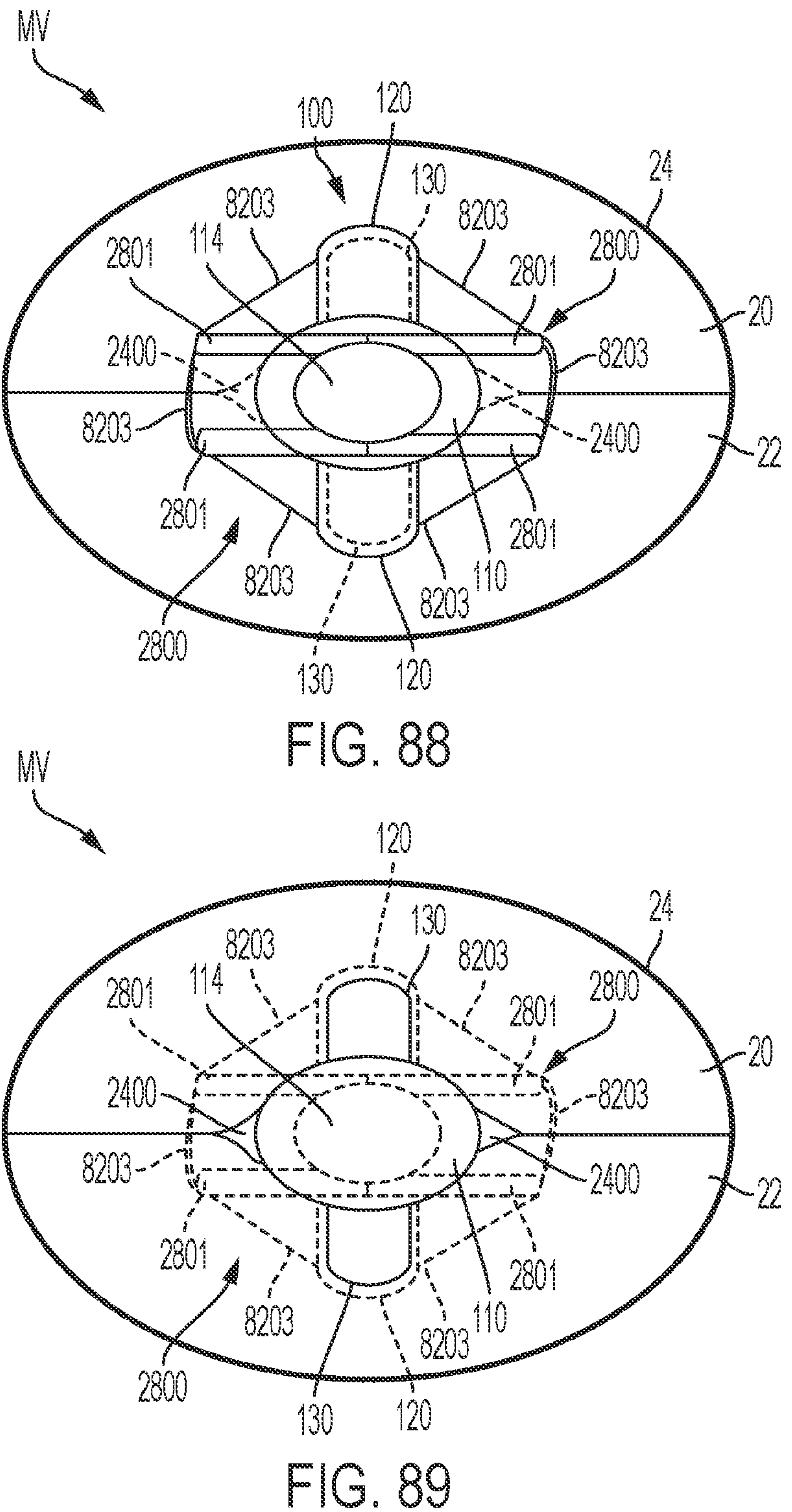
FIG. 88 shows the implantable prosthetic device implanted in the first position within the native valve shown in FIG. 82, viewed from a ventricle side of the native valve.
FIG. 89 shows the implantable prosthetic device implanted in the first position within the native valve shown in FIG. 82, viewed from an atrial side of the native valve.

Referring to FIGS. 86 and 87, contraction of the left ventricle LV pushes blood toward the mitral valve MV in the direction Y and engages the deflecting paddles 2801 and barrier element 8203 of the leak control extensions 2800, which prevents blood from moving through the openings 2400 and into the left atrium LA. In some embodiments, the blood provides a force on the deflecting paddles 2801 that causes the deflecting paddles 2801 to pivot about the cap 114 or flex relative to the cap such that the blood moves around the leak control extensions 2800 in the direction Z. In some embodiments, the blood provides a force on the barrier element 8203 that causes a portion of the barrier element 8203 positioned between the two deflecting paddles 2801 to move in an upward direction.

Referring to FIGS. 90 and 91, the device 100 shown in FIGS. 82-89 can be placed within the native valve in a location near the annulus 24. Similar to the device 100 being located in a more central location within the native valve (as shown in FIGS. 82-89), openings 2400 may form where both leaflets 20, 22 and the device 100 meet. As shown in the illustrated embodiment, when the device 100 is placed near the annulus 24, the force on the native valve by the device 100 may cause the opening 2400 adjacent to the annulus 24 to have a deformed shape. In some embodiments, the leak control extensions 2800 are flexible such that forces applied to the leak control extensions cause the leak control extensions to compress. For example, as shown in FIGS. 90 and 91, the leak control extension 2800 adjacent to the annulus 24 is pressed against the annulus 24 (or the side wall of the ventricle), which causes the leak control extension 2800 to compress into a deformed shape. This compression of the leak control extensions 2800 allows the leak control extensions to cover the deformed opening 2400 that is adjacent to the annulus 24. The flexible leak control extensions 2800 are advantageous because they allow the device 100 to be positioned within the native valve at various positions. In addition, the flexible leak control extensions 2800 are advantageous because they are capable of taking a form needed to block blood-flow through any deformed openings caused by the connection between the device 100 and the leaflets 20, 22.

While various inventive aspects, concepts and features of the disclosures may be described and illustrated herein as embodied in combination in the example embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. Further, the techniques, methods, operations, steps, etc. described or suggested herein can be performed on a living animal or on a non-living simulation, such as on a cadaver, cadaver heart, simulator (e.g. with the body parts, tissue, etc. being simulated), etc. The words used in the claims have their full ordinary meanings and are not limited in any way by the description of the embodiments in the specification.

The invention claimed is:

1. A valve repair device for repairing a native valve of a heart of a patient, the valve repair device comprising:
- an anchor portion comprising a first anchor and a second anchor, wherein the first and second anchors are configured to be moved from an open position to a closed position to secure the implantable device to leaflets of a native valve;
- a barrier element attached to the first anchor and the second anchor such that the barrier element extends between the first anchor and the second anchor to inhibit blood regurgitation through one or more openings between leaflets of the native valve during systole;
- wherein the barrier element is a component of a leak control extension that comprises one or more deflecting paddles;
- wherein the one or more deflecting paddles are configured to flex toward a ventricle of the heart during diastole; and
- wherein the one or more deflecting paddles are configured to flex toward an atrium of the heart during systole.

2. The valve repair device according to claim 1, wherein the barrier element comprises one or more pieces of a cloth material.

3. The valve repair device according to claim 1, wherein the barrier element comprises one or more pieces of a biocompatible material.

4. The valve repair device according to claim 1, wherein the barrier element extends from the first anchor to the second anchor to create a barrier that extends between the first anchor and the second anchor.

5. The valve repair device according to claim 1, wherein each of the first and second anchors comprise a paddle frame, and wherein the barrier element is attached to the paddle frame of both the first and second anchors.

6. The valve repair device according to claim 1, further comprising a spacer disposed between the first anchor and the second anchor.

7. A valve repair device for repairing a native valve of a patient, the valve repair device comprising:
- an anchor portion comprising a first anchor and a second anchor, wherein the first and second anchors are configured to be moved from an open position to a closed position to secure the implantable device to leaflets of a native valve;
- a leak control extension that comprises one or more deflecting paddles;
- wherein the one or more deflecting paddles are positioned in a ventricle of the native valve when the implantable device is secured to the leaflets of the native valve;
- wherein the one or more deflecting paddles are configured to flex toward an atrium of the heart during systole; and
- wherein the one or more deflecting paddles are configured to flex toward a ventricle of the heart during diastole.

8. The valve repair device of claim 7 wherein the leak control extensions are configured to prevent blood from flowing through openings between the device and the leaflets of the native valve.

9. The valve repair device according to claim 7, wherein each of the first and second anchors comprise a paddle frame.

10. The valve repair device of claim 9 further comprising a cap attached to the pair of paddle frames, wherein distal movement of the cap opens the first and second anchors, and wherein the one or more deflecting paddles are attached to the cap.

11. The valve repair device of claim 10 wherein the deflecting paddles are configured to pivot relative to the cap when the native valve is in diastole such that blood moves around the deflecting paddles from the atrium to the ventricle.

12. The valve repair device of claim 7 wherein the deflecting paddles are configured to flex when the native valve is in diastole such that blood moves around the deflecting paddles from the atrium to the ventricle.

13. The valve repair device according to claim 7, further comprising a spacer disposed between the first anchor and the second anchor.

* * * * *